United States Patent [19]
Farooq et al.

[11] Patent Number: 5,935,908
[45] Date of Patent: Aug. 10, 1999

[54] PESTICIDAL INDAZOLE DERIVATIVES

[75] Inventors: Saleem Farooq, Arisdorf; René Zurflüh, Basel; Henry Szczepanski, Wallbach; Roger Graham Hall, Aesch, all of Switzerland

[73] Assignee: Novartis Crop Protection, Inc., Greensboro, N.C.

[21] Appl. No.: 09/011,916

[22] PCT Filed: Aug. 5, 1996

[86] PCT No.: PCT/EP96/03452

§ 371 Date: Feb. 17, 1998

§ 102(e) Date: Feb. 17, 1998

[87] PCT Pub. No.: WO97/07103

PCT Pub. Date: Feb. 27, 1997

[30]   Foreign Application Priority Data

Aug. 15, 1995 [CH] Switzerland ............ 2340/95
Aug. 21, 1995 [CH] Switzerland ............ 2381/95
Feb. 6, 1996  [CH] Switzerland ............ 0305/96

[51] Int. Cl.⁶ ............ A01N 43/56; C07D 231/56
[52] U.S. Cl. ............ 504/281; 514/405; 548/362.5
[58] Field of Search ............ 548/362.5; 514/405; 504/281

[56]   References Cited

U.S. PATENT DOCUMENTS

| 3,253,034 | 5/1966 | McLoughlin et al. | 564/363 |
| 4,159,375 | 6/1979 | Trust et al. | 544/184 |
| 5,646,147 | 7/1997 | Kuhn et al. | 514/252 |
| 5,756,426 | 5/1998 | Ziegler et al. | 504/312 |

FOREIGN PATENT DOCUMENTS

| 2 043 733 | 5/1991 | Canada. |
| 0 256 667 | 2/1988 | European Pat. Off.. |
| 0 370 629 | 5/1990 | European Pat. Off.. |
| 0 389 189 | 9/1990 | European Pat. Off.. |
| 7 403 524 | 5/1974 | Netherlands. |
| 95/18789 | 7/1995 | WIPO. |
| 95/21154 | 8/1995 | WIPO. |
| 95/21156 | 8/1995 | WIPO. |
| 96/14305 | 5/1996 | WIPO. |

OTHER PUBLICATIONS

Borsche, W, et al. (1936) "1–Arylindazoles." (CA30: 5219).
Kazanbieva, MA, et al. (1965) "Synthesis and conversions of 1–methy–3–formylindazole." (CA63: 14847c).
Meisenheimer, J, et al. (1924) "The isomeric aclindazoles of K. v. Auwers." (CA19: 508–509).

*Primary Examiner*—Fiona T. Powers
*Attorney, Agent, or Firm*—Michael P. Morris

[57]   ABSTRACT

Compounds of formula (1), wherein X, Y, Z $R_2$, $R_3$, $R_4$, $R_5$, $R_7$, $R_9$ and n are as defined in claim 1 and, where appropriate, E/Z isomers, mixtures of E/Z isomers and/or tautomers thereof, in each case in free form or in agrochemically suitable salt form, can be used as agrochemical active ingredients and can be prepared in a manner known per se.

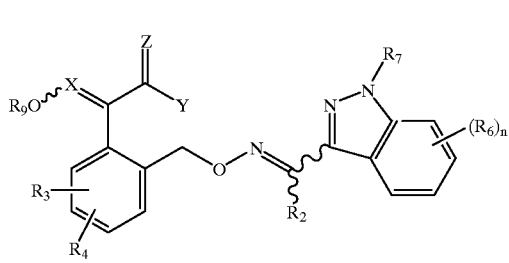

(I)

25 Claims, No Drawings

PESTICIDAL INDAZOLE DERIVATIVES

The present invention relates to compounds of formula

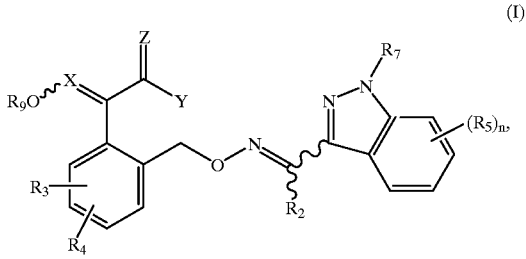

(I)

wherein
X is CH or N, Y is OR$_1$ and Z is O, or
X is N, Y is NHR$_8$ and Z is O, S or S(=O);
R$_1$ is C$_1$–C$_4$alkyl;
R$_2$ is H, C$_1$–C$_4$alkyl, halo-C$_1$–C$_4$alkyl, C$_3$–C$_6$cycloalkyl, C$_1$–C$_4$alkoxymethyl, C$_1$–C$_4$alkoxy, halo-C$_1$–C$_4$alkoxy, C$_1$–C$_4$alkylthio, halo-C$_1$–C$_4$alkylthio or —CN;
R$_3$ and R$_4$ are each independently of the other H, C$_1$–C$_4$alkyl, C$_1$–C$_4$alkoxy, OH, —CN, NO$_2$; a (C$_1$–C$_4$alkyl)$_3$Si group wherein the alkyl groups may be identical or different; halogen, (C$_1$–C$_4$alkyl)S(=O)$_m$, (halo-C$_1$–C$_4$alkyl)S(=O)$_m$, halo-C$_1$–C$_4$alkyl or halo-C$_1$–C$_4$alkoxy;
R$_5$ is unsubstituted or substituted C$_1$–C$_6$alkyl, C$_1$–C$_6$alkoxy, halo-C$_1$–C$_6$alkoxy, C$_1$–C$_6$-alkylthio, halo-C$_1$–C$_6$alkylthio, C$_1$–C$_6$alkylsulfinyl, halo-C$_1$–C$_6$alkylsulfinyl, C$_1$–C$_6$alkylsulfonyl, halo-C$_1$–C$_6$alkylsulfonyl, C$_1$–C$_6$alkylcarbonyl, halo-C$_1$–C$_6$alkylcarbonyl, C$_1$–C$_6$alkoxycarbonyl, halo-C$_1$–C$_6$alkoxycarbonyl, C$_1$–C$_6$alkylaminocarbonyl; di(C$_1$–C$_6$alkyl)aminocarbonyl wherein the alkyl groups may be identical or different; C$_1$–C$_6$alkylaminothiocarbonyl; di(C$_1$–C$_6$alkyl) aminothiocarbonyl wherein the alkyl groups may be identical or different; C$_1$–C$_6$alkylamino, di(C$_1$–C$_6$alkyl)amino, halogen, NO$_2$; an unsubstituted or mono- to tetra-substituted C$_1$–C$_4$alkylenedioxy group, the substituents being selected from the group consisting of C$_1$–C$_4$alkyl and halogen; QR$_6$, —CN or SF$_5$ wherein, when n is greater than 1, the radicals R$_5$ may be identical or different;
R$_6$ is a C$_2$–C$_6$alkenyl or C$_2$–C$_6$alkynyl group that is unsubstituted or substituted by from 1 to 3 halogen atoms; a (C$_1$–C$_4$alkyl)$_3$Si group wherein the alkyl groups may be identical or different; —CN; an unsubstituted or mono- to penta-substituted C$_3$–C$_6$cycloalkyl, aryl or heterocyclyl group, the substituents being selected from the group consisting of halogen, C$_1$–C$_6$alkyl, halo-C$_1$–C$_6$alkyl, C$_1$–C$_6$alkoxy, halo-C$_1$–C$_6$alkoxy, phenoxy and —CN;
R$_7$ is H, unsubstituted or substituted C$_1$–C$_6$alkyl, C$_3$–C$_6$cycloalkyl, a C$_2$–C$_6$alkenyl- or C$_2$–C$_6$alkynyl-group that is unsubstituted or substituted by from 1 to 3 halogen atoms; phenyl or mono- to penta-substituted phenyl, the substituents being selected from the group consisting of C$_1$–C$_4$alkyl, halo-C$_1$–C$_4$alkyl, halogen, C$_1$–C$_4$alkoxy and halo-C$_1$–C$_4$alkoxy;
R$_8$ is H or C$_1$–C$_4$alkyl;
R$_9$ is CH$_3$, CH$_2$F or CHF$_2$;
Q is a direct bond, O, O(C$_1$–C$_6$alkylene), (C$_1$–C$_6$alkylene)O, S(=O)$_p$, S(=O)$_p$(C$_1$–C$_6$alkylene), (C$_1$–C$_6$alkylene)S(=O)$_p$, C$_1$–C$_8$alkylene, C$_2$–C$_6$alkenylene or C$_2$–C$_6$alkynylene;
m is 0, 1 or 2;
n is 0, 1, 2, 3 or 4; and
p is 0,1 or 2,
and, where appropriate, to the possible E/Z isomers, mixtures of E/Z isomers and/or tautomers thereof, in each case in free form or in salt form, to a process for the preparation of those compounds, E/Z isomers and tautomers and to the use of those compounds, E/Z isomers and tautomers, to pesticidal compositions comprising an active ingredient selected from those compounds, E/Z isomers and tautomers, to a process for the preparation of those compositions and to the use of those compositions, to intermediates, in free form or in salt form, for the preparation of those compounds, where appropriate to tautomers, in free form or in salt form, of those Intermediates, to a process for the preparation of those intermediates and the tautomers thereof and to the use of those intermediates and the tautomers thereof.

In the literature, certain methoxyacrylic acid derivatives are proposed as active ingredients of pesticidal compositions. The biological properties of those known compounds are not, however, entirely satisfactory in the field of pest control and there is therefore a need to make available other compounds having pesticidal properties, especially for controlling insects and representatives of the order Acarina and especially also for controlling phytopathogenic microorganisms, that problem being solved according to the invention by the provision of the present compounds of formula I.

Some of the compounds of formula I contain asymmetric carbon atoms, with the result that those compounds can occur in optically active form. Owing to the presence of the C=X and oximino double bonds, the compounds can occur in the form of E isomers and Z isomers. Atropisomerism of the compounds may also occur. Formula I is intended to include all those possible isomeric forms, and mixtures thereof, for example racemates or mixtures of E/Z isomers.

Unless otherwise defined, the general terms used hereinbefore and hereinafter have the following meanings.

Unless otherwise defined, carbon-containing groups and compounds each contain from 1 up to and including 8, preferably from 1 up to and including 6, especially from 1 up to and including 4 and above all 1 or 2, carbon atoms.

Alkyl, both as a group per se and as a structural element of other groups and compounds, such as haloalkyl, alkoxy and alkylthio, is, in each case taking due account of the number of carbon atoms contained in the corresponding group or compound, either straight-chained, i.e. methyl, ethyl, propyl, butyl, pentyl or hexyl, or branched, e.g. isopropyl, isobutyl, sec-butyl, tert-butyl, isopentyl, neopentyl or isohexyl.

Alkenyl, both as a group per se and as a stuctural element of other groups and compounds, such as haloalkenyl, is, in each case taking due account of the number of carbon atoms contained in the corresponding group or compound, either straight-chained, such as vinyl, 1-methylvinyl, allyl, 1-butenyl or 2-hexenyl, or branched, such as isopropenyl.

Alkynyl, both as a group per se and as a stuctural element of other groups and compounds, such as haloalkynyl, is, in each case taking due account of the number of carbon atoms contained in the corresponding group or compound, either straight-chained, such as propargyl, 2-butynyl or 5-hexynyl, or branched, such as 2-ethynylpropyl or 2-propargylisopropyl.

C$_3$–C$_6$Cycloalkyl is cyclopropyl, cyclobutyl, cyclopentyl or cyclohexyl.

Alkylenedioxy is —O(alkylene)O—.

Alkylene, both as a group per se and as a stuctural element of other groups and compounds, such as O(alkylene), (alkylene)O, $S(=O)_p$(alkylene), (alkylene)$S(=O)_p$ or alkylenedioxy, is, in each case taking due account of the number of carbon atoms contained in the corresponding group or compound, either straight-chained, e.g. —CH$_2$CH$_2$—, —CH$_2$CH$_2$CH$_2$— or —CH$_2$CH$_2$CH$_2$CH$_2$—, or branched, e.g. —CH(CH$_3$)—, —CH(C$_2$H$_5$)—, —C(CH$_3$)$_2$—, —CH(CH$_3$)CH$_2$— or —CH(CH$_3$)CH(CH$_3$)—.

Alkenylene is, in each case taking due account of the number of carbon atoms contained in the corresponding compound, either straight-chained, such as vin-1,2-ylene, all-1,3ylene, but-1-en-1,4-ylene or hex-2-en-1,6-ylene, or branched, e.g. 1-methylvin-1,2-ylene.

Alkynylene is, in each case taking due account of the number of carbon atoms contained in the corresponding compound, either straight-chained, such as propargylene, 2-butynylene or 5-hexynylene, or branched, e.g. 2-ethynylpropylene or 2-propargylisopropylene.

Aryl is phenyl or naphthyl, especially phenyl.

Heterocyclyl denotes a 5- to 7-membered aromatic or non-aromatic ring having from one to three hetero atoms selected from the group consisting of N, O and S. Preference is given to aromatic 5- and 6-membered rings containing a nitrogen atom as hetero atom and where appropriate a further hetero atom, preferably nitrogen or sulfur, especially nitrogen.

Halogen, both as a group per se and as a structural element of other groups and compounds, such as haloalkyl, haloalkenyl and haloalkynyl, is fluorine, chlorine, bromine or iodine, especially fluorine, chlorine or bromine, more especially fluorine or chlorine and above all fluorine.

Halo-substituted carbon-containing groups and compounds, such as haloalkyl, haloalkenyl or haloalkynyl, may be partially halogenated or perhalogenated, the halogen substituents in the case of multiple halogenation being identical or different. Examples of haloalkyl, both as a group per se and as a structural element of other groups and compounds, such as haloalkynyl, are methyl mono- to tri-substituted by fluorine, chlorine and/or by bromine, such as CHF$_2$ or CF$_3$; ethyl mono- to penta-substituted by fluorine, chlorine and/or by bromine, such as CH$_2$CF$_3$, CF$_2$CF$_3$, CF$_2$CCl$_3$, CF$_2$CHCl$_2$, CF$_2$CHF$_2$, CF$_2$CFCl$_2$, CF$_2$CHBr$_2$, CF$_2$CHClF, CF$_2$CHBrF or CClFCHClF; propyl or isopropyl each mono- to hepta-substituted by fluorine, chlorine and/or by bromine, such as CH$_2$CHBrCH$_2$Br, CF$_2$CHFCF$_3$, CH$_2$CF$_2$CF$_3$ or CH(CF$_3$)$_2$; and butyl, or one of the isomers of butyl, mono- to nona-substituted by fluorine, chlorine and/or by bromine, such as CF(CF$_3$)CHFCF$_3$ or CH$_2$(CF$_2$)$_2$CF$_3$. Haloalkenyl is, for example, CH$_2$CH=CHCl, CH$_2$CH=CCl$_2$, CH$_2$CF=CF$_2$ or CH$_2$CH=CHCH$_2$Br. Haloalkynyl is, for example, CH$_2$C≡CF, CH$_2$C≡CCH$_2$Cl or CF$_2$CF$_2$C≡CCH$_2$F.

As is familiar to a person skilled in the art, some of the compounds of formula I may be in the form of tautomers, especially when R$_7$ is H. Hereinbefore and hereinafter, the compounds of formula I are therefore to be understood to include corresponding tautomers, even if the latter are not specifically mentioned in each case.

Compounds of formula I having at least one basic centre are capable, for example, of forming acid addition salts. Those salts are formed, for example, with strong inorganic acids, such as mineral acids, for example perchloric acid, sulfuric acid, nitric acid, nitrous acid, a phosphoric acid or a hydrohalic acid, with strong organic carboxylic acids, such as unsubstituted or substituted, for example halo-substituted, C$_1$–C$_4$alkanecarboxylic acids, for example acetic acid, saturated or unsaturated dicarboxylic acids, for example oxalic, malonic, succinic, maleic, fumaric or phthalic acid, hydroxycarboxylic acids, for example ascorbic, lactic, malic, tartaric or citric acid, or benzoic acid, or with organic sulfonic acids, such as unsubstituted or substituted, for example halo-substituted, C$_1$–C$_4$alkane- or aryl-sulfonic acids, for example methane- or p-toluene-sulfonic acid. Furthermore, compounds of formula I having at least one acid group are capable of forming salts with bases. Suitable salts with bases are, for example, metal salts, such as alkali metal or alkaline earth metal salts, for example sodium, potassium or magnesium salts, or salts with ammonia or an organic amine, such as morpholine, piperidine, pyrrolidine, a mono-, di- or tri-lower alkylamine, for example ethyl-, diethyl-, triethyl- or dimethyl-propylamine, or a mono-, di- or tri-hydroxy-lower alkylamine, for example mono-, di- or tri-ethanolamine. In addition, corresponding internal salts may also be formed. Preference is given within the scope of the invention to agrochemically advantageous salts. In view of the close relationship between the compounds of formula I in free form and in the form of their salts, any reference hereinbefore or hereinafter to the compounds of formula I is to be understood as including also the corresponding salts, where appropriate and expedient. The same applies in the case of tautomers of compounds of formula I and the salts thereof. The free form is generally preferred in each case.

A preferred form within the scope of the invention is a compound of formula I wherein X is CH or N, Y is OR$_1$ and Z is O, or X is N, Y is NHR$_8$ and Z is O, S or S(=O);

R$_1$ is C$_1$–C$_4$alkyl;

R$_2$ is H, C$_1$–C$_4$alkyl, halo-C$_1$–C$_4$alkyl, C$_3$–C$_6$cycloalkyl, C$_1$–C$_4$alkoxymethyl, C$_1$–C$_4$alkoxy, halo-C$_1$–C$_4$alkoxy, C$_1$–C$_4$alkylthio, halo-C$_1$–C$_4$alkylthio or CN;

R$_3$ and R$_4$ are each independently of the other H, C$_1$–C$_4$alkyl, C$_1$–C$_4$alkoxy, OH, CN, NO$_2$; a (C$_1$–C$_4$alkyl)$_3$Si group wherein the alkyl groups may be identical or different; halogen, (C$_1$–C$_4$alkyl)S(=O)$_m$, (halo-C$_1$–C$_4$alkyl)S(=O)$_m$, halo-C$_1$–C$_4$alkyl or halo-C$_1$–C$_4$alkoxy;

R$_5$ C$_1$–C$_6$alkyl, halo-C$_1$–C$_6$alkyl, C$_1$–C$_6$alkoxy, halo-C$_1$–C$_6$alkoxy, C$_1$–C$_6$alkylthio, halo-C$_1$–C$_6$alkylthio, C$_1$–C$_6$alkylsulfinyl, halo-C$_1$–C$_6$alkylsulfinyl, C$_1$–C$_6$alkylsulfonyl, halo-C$_1$–C$_6$alkylsulfonyl, C$_1$–C$_6$alkoxy-C$_1$–C$_6$alkyl, halo-C$_1$–C$_6$alkoxy-C$_1$–C$_6$alkyl, C$_1$–C$_6$-alkylthio-C$_1$–C$_6$alkyl, halo-C$_1$–C$_6$alkylthio-C$_1$–C$_6$alkyl, C$_1$–C$_6$alkylsulfinyl-C$_1$–C$_6$alkyl, halo-C$_1$–C$_6$alkylsulfinyl-C$_1$–C$_6$alkyl, C$_1$–C$_6$alkylsulfonyl-C$_1$–C$_6$alkyl, halo-C$_1$–C$_6$alkylsulfonyl-C$_1$–C$_6$alkyl, C$_1$–C$_6$alkylcarbonyl, halo-C$_1$–C$_6$alkylcarbonyl, C$_1$–C$_6$alkoxycarbonyl, halo-C$_1$–C$_6$alkoxycarbonyl, C$_1$–C$_6$alkylaminocarbonyl; di(C$_1$–C$_6$alkyl)aminocarbonyl wherein the alkyl groups may be identical or different; C$_1$–C$_6$alkylaminothiocarbonyl; di(C$_1$–C$_6$alkyl)aminothiocarbonyl wherein the alkyl groups may be identical or different; C$_1$–C$_6$alkylamino, di(C$_1$–C$_6$alkyl)amino, halogen, NO$_2$; an unsubstituted or mono- to tetra-substituted C$_1$–C$_4$alkylenedioxy group, the substituents being selected from the group consisting of C$_1$–C$_4$alkyl and halogen; QR$_6$, CN or SF$_5$ wherein, when n is greater than 1, the radicals R$_5$ may be identical or different;

R$_6$ is a C$_2$–C$_6$alkenyl or C$_2$–C$_6$alkynyl group that is unsubstituted or substituted by from 1 to 3 halogen atoms; a $(C_1-C_4alkyl)_3Si$ group wherein the alkyl groups may be identical or different; CN; an unsubstituted or mono- to penta-substituted $C_3-C_6$cycloalkyl, aryl or heterocyclyl group, the substituents being selected from the group consisting of halogen, $C_1-C_6$alkyl, halo-$C_1-C_6$alkyl, $C_1-C_6$alkoxy, halo-$C_1-C_6$alkoxy and CN;

$R_7$ is H, $C_1-C_6$alkyl, halo-$C_1-C_6$alkyl, $C_1-C_4$alkoxy-$C_1-C_4$alkyl, $C_3-C_6$cycloalkyl, $C_1-C_4$alkylthio-$C_1-C_4$alkyl, $C_1-C_4$alkylsulfinyl-$C_1-C_4$alkyl, $C_1-C_4$alkylsulfonyl-$C_1-C_4$alkyl; a $C_2-C_6$alkenyl or $C_2-C_6$alkynyl group that is unsubstituted or substituted by from 1 to 3 halogen atoms; phenyl or mono- to penta-substituted phenyl, the substituents being selected from the group consisting of $C_1-C_4$alkyl, halo-$C_1-C_4$alkyl, halogen, $C_1-C_4$alkoxy and halo-$C_1-C_4$alkoxy;

$R_8$ is H or $C_1-C_4$alkyl;

$R_9$ is $CH_3$, $CH_2F$ or $CHF_2$;

Q is a direct bond, O, $O(C_1-C_6alkylene)$, $(C_1-C_6alkylene)O$, $S(=O)_p$, $S(=O)_p(C_1-C_6alkylene)$, $(C_1-C_6alkylene)S(=O)_p$, $C_1-C_8alkylene$, $C_2-C_6$alkenylene or $C_2-C_6$alkynylene; and m is 0, 1 or 2; n is 0, 1, 2, 3 or 4; and p is 0, 1 or 2.

Especially preferred forms within the scope of the invention are compounds of formula I wherein:

(1) X is CH;

(2) Y is $OR_1$, preferably $C_1-C_2$alkoxy, especially methoxy;

(3) Z is O;

(4) $R_1$ is $C_1-C_2$alkyl;

(5) $R_2$ is $C_1-C_4$alkyl, halo-$C_1-C_4$alkyl, cyclopropyl, halo-$C_1-C_4$alkylthio or CN, preferably $C_1-C_3$alkyl, halo-$C_1-C_2$alkyl, cyclopropyl, halo-$C_1-C_4$alkylthio or CN, especially $C_1-C_3$alkyl, halomethyl, cyclopropyl, halomethylthio or CN, more especially methyl;

(6) $R_3$ is H, $C_1-C_2$alkyl, $C_1-C_2$alkoxy, CN, $NO_2$, $CF_3$ or halogen, preferably H, $C_1-C_2$alkyl, $C_1-C_2$alkoxy, $CF_3$ or halogen, especially H, methyl, methoxy, chlorine or fluorine, more especially H;

(7) $R_4$ is H, $C_1-C_2$alkyl, $C_1-C_2$alkoxy, CN, $NO_2$, $CF_3$ or halogen, preferably H, $C_1-C_2$alkyl, $C_1-C_2$alkoxy, $CF_3$ or halogen, especially H, methyl, methoxy, chlorine or fluorine, more especially H;

(8) $R_5$ is $C_1-C_4$alkyl, halo-$C_1-C_4$alkyl, $C_1-C_4$alkoxy, halo-$C_1-C_4$alkoxy, halogen, $NO_2$; an unsubstituted or mono- to tetra-substituted $C_1-C_4$alkylenedioxy group, the substituents being selected from the group consisting of $C_1-C_4$alkyl and halogen; or $QR_6$, preferably $C_1-C_2$alkyl, halo-$C_1-C_2$alkyl, halogen or $QR_6$; especially methyl, fluorine, chlorine or $QR_6$;

(9) $R_6$ is a $C_2-C_6$alkenyl or $C_2-C_6$alkynyl group that is unsubstituted or substituted by from 1 to 3 halogen atoms; an unsubstituted or mono- to penta-substituted $C_3-C_6$cycloalkyl, aryl or heterocyclyl group, the substituents being selected from the group consisting of halogen, $C_1-C_6$alkyl, halo-Cl-$C_6$alkyl, $C_1-C_6$alkoxy and CN; preferably a $C_2-C_3$alkenyl or propynyl group that is unsubstituted or substituted by 1 or 2 halogen atoms; an unsubstituted or mono- to tri-substituted cyclopropyl or phenyl group, the substituents being selected from the group consisting of halogen, methyl, halomethyl, methoxy and CN; especially a cyclopropyl or phenyl group that is unsubstituted or mono- to tri-substituted by halogen, methyl, halomethyl or by methoxy;

(10) $R_7$ is $C_1-C_6$alkyl, preferably $C_1-C_2$alkyl, especially methyl;

(11) $R_8$ is $C_1-C_4$alkyl, preferably $C_1-C_2$alkyl, especially methyl;

(12) $R_9$ is methyl or $CH_2F$, preferably methyl;

(13) Q is a direct single bond, O or $O(C_1-C_4alkylene)$, preferably O or $O(C_1-C_2alkylene)$, especially O or O(methylene);

(14) m is 0 or 1, preferably 0;

(15) n is 0, 1, 2 or 3, preferably 0, 1 or 2;

(16) p is 0 or 1, preferably 0;

(17) X is CH, Y is $OR_1$, Z is O, $R_1$ is $C_1-C_2$alkyl, $R_2$ is $C_1-C_3$alkyl, halo-$C_1-C_2$alkyl, cyclopropyl, halo-$C_1-C_2$alkylthio or CN, $R_3$ and $R_4$ are each independently of the other H, $C_1-C_2$alkyl, $C_1-C_2$alkoxy, $CF_3$ or halogen, $R_5$ is $C_1-C_2$alkyl, halo-$C_1-C_2$alkyl, halogen or $QR_6$;

$R_6$ is a $C_2-C_6$alkenyl or $C_2-C_6$alkynyl group that is unsubstituted or substituted by from 1 to 3 halogen atoms; an unsubstituted or mono- to tri-substituted $C_3-C_6$cycloalkyl or phenyl group, the substituents being selected from the group consisting of halogen, $C_1-C_6$alkyl, halo-$C_1-C_6$alkyl, $C_1-C_6$alkoxy and CN;

$R_7$ is $C_1-C_2$alkyl, $R_9$ is methyl or $CH_2F$,

Q is O or $O(C_1-C_2alkylene)$, and n is 0, 1 or 2;

(18) X is CH, Y is methoxy, Z is O, $R_2$ is $C_1-C_3$alkyl, halomethyl, cyclopropyl, halomethylthio or CN, $R_3$ and $R_4$ are each independently of the other H, methyl, methoxy, chlorine or fluorine, $R_5$ is methyl, fluorine, chlorine or $QR_6$, $R_6$ is a cyclopropyl or phenyl group that is unsubstituted or mono- to tri-substituted by halogen, methyl, halomethyl or by methoxy, $R_7$ is $C_1-C_2$alkyl, $R_9$ is methyl, Q is O or O(methylene), and n is 0, 1 or 2.

Special preference is given within the scope of the invention to the compounds of formula I listed in Tables 3 to 14 and, where appropriate, the E/Z isomers thereof.

Preference is given specifically within the scope of the invention to: 2-[[[(1-{1-methylindazol-3-yl}ethylidene)amino]oxy]methyl]-α-(methoxymethylene)phenylacetic acid methyl ester (Compound 3.1), 2-[[[(1-{6-[(2,2-dichlorocyclopropyl)methoxy]-5-fluoro-1-methylindazol-3-yl}ethylidene)amino]oxy]methyl]-α-(methoxymethylene)phenylacetic acid methyl ester (Compound 3.77), 2-[[[(1-{5-fluoro-6-[(4-fluorophenyl)methoxy]-1-methylindazol-3-yl}ethylidene)amino]oxy]methyl]-α-(methoxymethylene)phenylacetic acid methyl ester (Compound 3.78) and 2-[[[(1-{6-fluoro-1-methylindazol-3-yl}ethylidene)amino]oxy]methyl]-α-(methoxymethylene)phenylacetic acid methyl ester (Compound 3.15) and to the E/Z isomers thereof.

The invention relates also to a process for the preparation of the compounds of formula I and, where appropriate, the E/Z isomers, mixtures of E/Z isomers and/or the tautomers thereof, in each case in free form or in salt form, which process comprises, for example:

a) for the preparation of a compound of formula I wherein Y is $OR_1$ and Z is O, either reacting a compound of formula

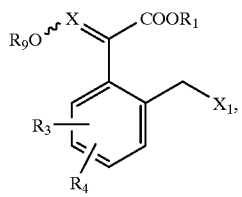

(II)

wherein X, $R_1$, $R_3$, $R_4$ and $R_9$ are as defined for formula I and $X_1$ is a leaving group, preferably in the presence of a base, with a compound of formula

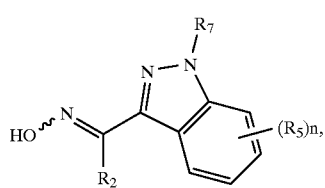

(III)

wherein n, $R_2$, $R_5$ and $R_7$ are as defined for formula I, or reacting a compound of formula

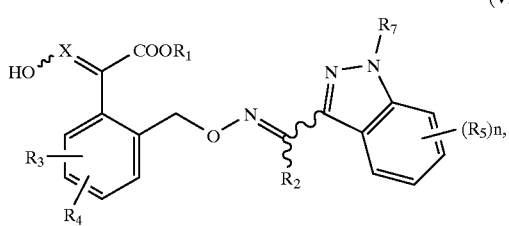

(VII)

wherein n, X, $R_2$, $R_3$, $R_4$, $R_5$ and $R_7$ are as defined for formula I, preferably in the presence of a base, with a compound of the formula $X_3R_9$, which is known or can be prepared analogously to corresponding known compounds and wherein $R_9$ is as defined for formula I and $X_3$ is a leaving group, or b) for the preparation of a compound of formula I wherein Y is $NHR_8$ and Z is O, reacting a compound of formula I wherein Y is $OR_1$, obtainable, for example, in accordance with process variant a), with a compound of the formula $NH_2R_8$, which is known or can be prepared analogously to corresponding known compounds and wherein $R_8$ is as defined for formula I, or c) for the preparation of a compound of formula I wherein Z is S, reacting a compound of formula I wherein Y is $NH_2R_8$ and Z is O, obtainable, for example, in accordance with process variant b), with $P_4S_{10}$ or Lawesson's reagent 2,4-Bis(4-methoxyphenyl)-1,3-dithia-2,4-diphosphetane-2,4-disulfide), or d) for the preparation of a compound of formula I wherein Z is SO, reacting a compound of formula I wherein Z is S, obtainable, for example, in accordance with process variant c), with an oxidising agent, and in each case, if desired, converting a compound of formula I obtainable in accordance with the process or by another method, or an E/Z isomer or a tautomer thereof, in each case in free form or in salt form, into a different compound of formula I or an E/Z isomer or a tautomer thereof, in each case in free form or in salt form, separating a mixture of E/Z isomers obtainable in accordance with the process and isolating the desired isomer and/or converting a free compound of formula I obtainable in accordance with the process or by another method, or an E/Z isomer or a tautomer thereof, into a salt or converting a salt of a compound of formula I obtainable in accordance with the process or by another method, or of an E/Z isomer or of a tautomer thereof, into the free compound of formula I or an E/Z isomer or a tautomer thereof or into a different salt.

The invention relates also to a process for the preparation of compounds of formula III, in each case in free form or in salt form, which process comprises, for example:

e) reacting a compound of formula

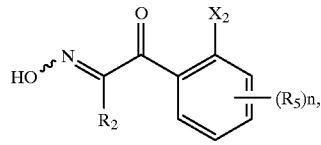

(IV)

wherein n, $R_2$ and $R_5$ are as defined for formula I and $X_2$ is a leaving group, where appropriate in the presence of a base, with a compound of formula $$H_2N-NHR_7 \quad (V),$$

which is known or can be prepared analogously to corresponding known compounds and wherein $R_7$ is as defined for formula I, and in each case, if desired, converting a compound of formula III obtainable in accordance with the process or by another method, or an E/Z isomer or a tautomer thereof, in each case in free form or in salt form, into a different compound of formula III or an E/Z isomer or a tautomer thereof, in each case in free form or in salt form, separating a mixture of E/Z isomers obtainable in accordance with the process and isolating the desired isomer and/or converting a free compound of formula III obtainable in accordance with the process or by another method, or an E/Z isomer or a tautomer thereof, into a salt or converting a salt of a compound of formula III obtainable in accordance with the process or by another method, or of an E/Z isomer or of a tautomer thereof, into the free compound of formula III or an E/Z isomer or a tautomer thereof or into a different salt.

The invention relates also to a process for the preparation of compounds of formula IV, in each case in free form or in salt form, which process comprises, for example:

f) reacting a compound of formula

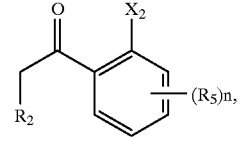

(VI)

which is known or can be prepared analogously to corresponding known compounds and wherein n, $R_2$ and $R_5$ are as defined for formula I and $X_2$ is as defined for formula IV, preferably in the presence of a base, with a $C_1$–$C_6$alkyl nitrite, preferably isopentyl nitrite, and in each case, if desired, converting a compound of formula IV obtainable in accordance with the process or by another method, or an E/Z isomer or a tautomer thereof, in each case in free form or in salt form, into a different compound of formula IV or an E/Z isomer or a tautomer thereof, in each case in free form or in salt form, separating a mixture of E/Z isomers obtainable in accordance with the process and isolating the desired isomer and/or converting a free compound of formula IV obtainable in accordance with the process or by another method, or an E/Z isomer or a tautomer thereof, into a salt or converting a salt of a compound of formula IV obtainable in accordance with the process or by another method, or of an E/Z isomer or of a tautomer thereof, into the free compound of formula IV or an E/Z isomer or a tautomer thereof or into a different salt.

The invention relates also to a process for the preparation of compounds of formula VII, in each case in free form or in salt form, which process comprises, for example:

g) for the preparation of a compound of formula VII wherein X is CH, reacting a compound of formula

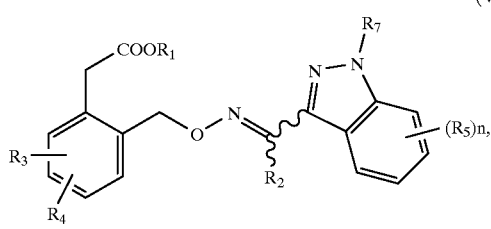

(VIII)

wherein n, $R_1$, $R_2$, $R_3$, $R_4$, $R_5$ and $R_7$ are as defined for formula I, preferably in the presence of a base, with a formic acid $C_1$–$C_6$alkyl ester, preferably formic acid methyl ester, or h) for the preparation of a compound of formula VII wherein X is N, reacting a compound of formula VIII, preferably in the presence of a base, with a $C_1$–$C_6$alkyl nitrite, preferably isopentyl nitrite, and in each case, if desired, converting a compound of formula VII obtainable in accordance with the process or by another method, or an E/Z isomer or a tautomer thereof, in each case in free form or in salt form, into a different compound of formula VII or an E/Z isomer or a tautomer thereof, in each case in free form or in salt form, separating a mixture of E/Z isomers obtainable in accordance with the process and isolating the desired isomer and/or converting a free compound of formula VII obtainable in accordance with the process or by another method, or an E/Z isomer or a tautomer thereof, into a salt or converting a salt of a compound of formula VII obtainable in accordance with the process or by another method, or of an E/Z isomer or of a tautomer thereof, into the free compound of formula VII or an E/Z isomer or a tautomer thereof or into a different salt.

The invention relates also to a process for the preparation of compounds of formula VII, in each case in free form or in salt form, which process comprises, for example:

i) either reacting a compound of formula

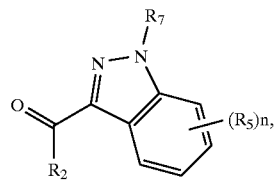

(IX)

wherein n, $R_2$, $R_5$ and $R_7$ are as defined for formula I, with a compound of formula

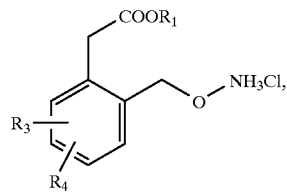

(X)

which is known or can be prepared analogously to corresponding known compounds and wherein $R_1$, $R_3$ and $R_4$ are as defined for formula I, or reacting a compound of formula III with a compound of formula

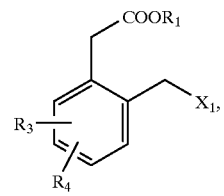

(XI)

which is known or can be prepared analogously to corresponding known compounds and wherein $R_1$, $R_3$ and $R_4$ are as defined for formula I and $X_1$ is a leaving group, preferably in the presence of a base, and in each case, if desired, converting a compound of formula VIII obtainable in accordance with the process or by another method, or an E/Z isomer or a tautomer thereof, in each case in free form or in salt form, into a different compound of formula VIII or an E/Z isomer or a tautomer thereof, in each case in free form or in salt form, separating a mixture of E/Z isomers obtainable in accordance with the process and isolating the desired isomer and/or converting a free compound of formula VIII obtainable in accordance with the process or by another method, or an E/Z isomer or a tautomer thereof, into a salt or converting a salt of a compound of formula VIII obtainable in accordance with the process or by another method, or of an E/Z isomer or of a tautomer thereof, into the free compound of formula VIII or an E/Z isomer or a tautomer thereof or into a different salt.

The invention relates also to a process for the preparation of compounds of formula II, wherein $X_1$ is halogen, in each case in free form or in salt form, which process comprises, for example:

j) reacting a compound of formula

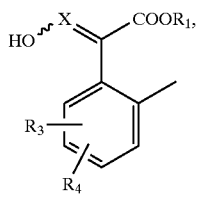

(XII)

which is known or can be prepared analogously to corresponding known compounds and wherein $R_1$, $R_3$ and $R_4$ are as defined for formula I, preferably in the presence of a base, with a compound of the formula $X_3R_9$, which is known or can be prepared analogously to corresponding known compounds and wherein $R_9$ is as defined for formula I and $X_3$ is a leaving group, and reacting the compound so obtainable with a halogenating agent, and in each case, if desired, converting a compound of formula II obtainable in accordance with the process or by another method, or an E/Z isomer or a tautomer thereof, in each case in free form or in salt form, into a different compound of formula II or an E/Z isomer or a tautomer thereof, in each case in free form or in salt form, separating a mixture of E/Z isomers obtainable in accordance with the process and isolating the desired isomer and/or converting a free compound of formula II obtainable in accordance with the process or by another method, or an E/Z isomer or a tautomer thereof, into a salt or converting a salt of a compound of formula II obtainable in accordance with the process or by another method, or of an E/Z isomer or of a tautomer thereof, into the free compound of formula II or an E/Z isomer or a tautomer thereof or into a different salt.

Some of the compounds of formulae 11 and IX are novel and, owing to their structure, are especially suitable for the preparation of the active end products of formula I or other active substances containing that part structure. Those compounds of formulae II and IX that are novel therefore also form part of the present invention.

The remarks made above in relation to E/Z isomers and tautomers of compounds of formula I apply analogously to the starting materials referred to hereinbefore and hereinafter as regards the E/Z isomers and tautomers thereof.

The reactions described hereinbefore and hereinafter are carried out in a manner known per se, for example in the absence or, customarily, in the presence of a suitable solvent or diluent or of a mixture thereof, the reactions being carried out as required with cooling, at room temperature or with heating, for example in a temperature range from approximately 0° C. to the boiling temperature of the reaction medium, preferably from approximately 20° C. to approximately +120° C., especially from 60° C. to 80° C. and, if necessary, in a closed vessel, under pressure, in an inert gas atmosphere and/or under anhydrous conditions. Especially advantageous reaction conditions can be found, for example, in the Examples.

The starting materials listed hereinbefore and hereinafter that are used for the preparation of the compounds of formula I and, where appropriate, the E/Z isomers and the tautomers thereof are known or can be prepared by methods known per se, for example in accordance with the following instructions.

Variant a):

Suitable leaving groups $X_1$ and $X_3$ are, for example, halogens, $C_1$–$C_8$alkyl- or aryl-sulfonates, preferably halogens, especially chlorine or bromine, more especially bromine.

Suitable bases for facilitating the reaction are, for example, alkali metal or alkaline earth metal hydroxides, hydrides, amides, alkanolates, acetates, carbonates, dialkylamides or alkylsilylamides, or alkylamines, alkylenediamines, unsubstituted or N-alkylated, saturated or unsaturated cycloalkylamines, basic heterocycles, ammonium hydroxides and carbocyclic amines. The following may be mentioned by way of example: sodium hydroxide, hydride, amide, methanolate, acetate or carbonate, potassium tert-butanolate, hydroxide, carbonate or hydride, lithium diisopropylamide, potassium bis(trimethylsilyl) amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,5-diazabicyclo[5.4.0]undec-5-ene (DBU).

The reactants can be reacted with one another as such, i.e. without the addition of a solvent or diluent, for example in the melt. In most cases, however, the addition of an inert solvent or diluent or of a mixture thereof is advantageous. Examples of such solvents or diluents that may be mentioned are: aromatic, aliphatic and alicyclic hydrocarbons and halogenated hydrocarbons, such as benzene, toluene, xylene, mesitylene, tetralin (tetrahydronaphthalene), chlorobenzene, dichlorobenzene, bromobenzene, petroleum ether, hexane, cyclohexane, dichloromethane, trichloromethane, tetrachloromethane, dichloroethane, trichloroethene or tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; amides, such as N,N-dimethylformamide, N,N-diethylformamide, N,N-dimethylacetamide, N-methylpyrrolidone or hexamethylphosphoric acid triamide; nitriles, such as acetonitrile or propionitrile; and sulfoxides, such as dimethyl sulfoxide. If the reaction is carried out in the presence of a base, bases used in excess, such as triethylamine, pyridine, N-methylmorpholine or N,N-diethylaniline, may also serve as solvents or diluents.

The reaction is advantageously carried out in a temperature range from approximately 0° C. to approximately +120° C., preferably from approximately 0° C. to approximately +30° C.

In a preferred form, a compound of formula III is reacted at from 0° C. to approximately +120° C., preferably at room temperature, in an inert solvent, preferably N,N-dimethylformamide, in the presence of a base, preferably an inorganic base, especially sodium hydride, with a compound of formula II.

Variant b):

The reactants can be reacted with one another as such, i.e. without the addition of a solvent or diluent, for example in the melt. In most cases, however, the addition of an inert solvent or diluent or of a mixture thereof is advantageous. Examples of such solvents or diluents that may be mentioned are: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol or propanol; amides, such as N,N-dimethylformamide, N,N-diethylformamide, N,N-dimethylacetamide, N-methylpyrrolidone or hexamethylphosphoric acid triamide; nitriles, such as acetonitrile or propionitrile; and sulfoxides, such as dimethyl sulfoxide.

The reaction is advantageously carried out in a temperature range from approximately 0° C. to approximately +120° C., preferably from approximately 0° C. to approximately +40° C.

In a preferred form, a compound of formula I wherein Y is $OR_1$ is reacted at from 0° C. to approximately +120° C., preferably at room temperature, in an inert solvent, preferably ethanol, with a compound of the formula $NH_2R_8$.

Variant c):

The reactants can be reacted with one another as such, i.e. without the addition of a solvent or diluent, for example in the melt. In most cases, however, the addition of an inert solvent or diluent or of a mixture thereof is advantageous. Examples of such solvents or diluents that may be mentioned are: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; and sulfoxides, such as dimethyl sulfoxide.

The reaction is advantageously carried out in a temperature range from approximately 0° C. to approximately +120° C., preferably from approximately 80° C. to approximately +120° C.

In a preferred form, a compound of formula I wherein Y is $NH_2R_8$ and Z is O is reacted at from 80° C. to approximately +120° C., preferably at 120° C., with $P_4S_{10}$.

Variant d):

Suitable oxidising agents are, for example, inorganic peroxides, such as sodium perborate, or hydrogen peroxide, or organic peracids, such as perbenzoic acid or peracetic acid, or mixtures of organic acids and hydrogen peroxide, such as acetic acid/hydrogen peroxide.

The reactants can be reacted with one another as such, i.e. without the addition of a solvent or diluent, for example in the melt. In most cases, however, the addition of an inert solvent or diluent or of a mixture thereof is advantageous. Examples of such solvents or diluents that may be mentioned are: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol or propanol; amides, such as N,N-dimethylformamide, N,N-diethylformamide, N,N-dimethylacetamide, N-methylpyrrolidone or hexamethylphosphoric acid triamide; nitriles, such as acetonitrile or propionitrile; and sulfoxides, such as dimethyl sulfoxide. If the reaction is carried out in the presence of an organic acid or a peracid, acids used in excess, for example strong organic carboxylic acids, such as unsubstituted or substituted, for example halo-substituted, $C_1$–$C_4$alkanecarboxylic acids, for example formic acid, acetic acid or propionic acid, may also serve as solvents or diluents.

The reaction is advantageously carried out in a temperature range from approximately 0° C. to approximately +120° C., preferably from approximately 0° C. to approximately +40° C.

In a preferred form, a compound of formula I wherein Z is S is reacted at from 0° C. to approximately +40° C., preferably at room temperature, in an organic acid, preferably acetic acid, with hydrogen peroxide.

Variant e):

Suitable leaving $X_2$ groups are, for example, halogens, $C_1$–$C_8$alkyl sulfates or aryl sulfates, preferably halogens, especially chlorine or fluorine, more especially fluorine.

The reactants can be reacted with one another as such, i.e. without the addition of a solvent or diluent, for example in the melt. In most cases, however, the addition of an inert solvent or diluent or of a mixture thereof is advantageous. Examples of such solvents or diluents that may be mentioned are: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol or propanol; amides, such as N,N-dimethylformamide, N,N-diethylformamide, N,N-dimethylacetamide, N-methylpyrrolidone or hexamethylphosphoric acid triamide; nitriles, such as acetonitrile or propionitrile; and sulfoxides, such as dimethyl sulfoxide. If the reaction is carried out in the presence of a base, bases used in excess, such as triethylamine, pyridine, N-methylmorpholine or N,N-diethylaniline, may also serve as solvents or diluents.

The reaction is advantageously carried out in a temperature range from approximately 0° C. to approximately +140° C., preferably from approximately 100° C. to approximately +140° C.

In a preferred form, a compound of formula IV is reacted at from 100° C. to approximately +140° C., preferably at approximately +140° C., with a compound of formula V.

Variant f):

Suitable bases for facilitating the reaction are, for example, alkali metal or alkaline earth metal hydroxides, hydrides, amides, alkanolates, acetates, carbonates, dialkylamides or alkylsilylamides, or alkylamines, alkylenediamines, unsubstituted or N-alkylated, saturated or unsaturated cycloalkylamines, basic heterocycles, ammonium hydroxides and carbocyclic amines. The following may be mentioned by way of example: sodium hydroxide, hydride, amide, methanolate, acetate or carbonate, potassium tert-butanolate, hydroxide, carbonate or hydride, lithium diisopropylamide, potassium bis(trimethylsilyl) amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,5-diazabicyclo[5.4.0]undec-5-ene (DBU).

The reactants can be reacted with one another as such, i.e. without the addition of a solvent or diluent, for example in the melt. In most cases, however, the addition of an inert solvent or diluent or of a mixture thereof is advantageous. Examples of such solvents or diluents that may be mentioned are: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol or propanol; amides, such as N,N-dimethylformamide, N,N-diethylformamide, N,N-dimethylacetamide, N-methylpyrrolidone or hexamethylphosphoric acid triamide; nitriles, such as acetonitrile or propionitrile; and sulfoxides, such as dimethyl sulfoxide. If the reaction is carried out in the presence of a base, bases used in excess, such as triethylamine, pyridine, N-methylmorpholine or N,N-diethylaniline, may also serve as solvents or diluents.

The reaction is advantageously carried out in a temperature range from approximately 0° C. to approximately +120° C., preferably from approximately 0° C. to approximately +40° C.

In a preferred form, a compound of formula VI is reacted at from 0° C. to approximately +40° C., preferably at room temperature, in an inert solvent, preferably an ether, especially 1,4-dioxane, with an alkyl nitrite, preferably isopentyl nitrite.

Variant g):

Suitable bases for facilitating the reaction are, for example, alkali metal or alkaline earth metal hydroxides, hydrides, amides, alkanolates, acetates, carbonates, dialkylamides or alkylsilylamides, or alkylamines, alkylenediamines, unsubstituted or N-alkylated, saturated or unsaturated cycloalkylamines, basic heterocycles, ammonium hydroxides and carbocyclic amines. The following may be mentioned by way of example: sodium hydroxide, hydride, amide, methanolate, acetate or carbonate, potassium tert-butanolate, hydroxide, carbonate or hydride, lithium diisopropylamide, potassium bis(trimethylsilyl) amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,5-diazabicyclo[5.4.0]undec-5-ene (DBU).

The reactants can be reacted with one another as such, i.e. without the addition of a solvent or diluent, for example in the melt. In most cases, however, the addition of an inert solvent or diluent or of a mixture thereof is advantageous. Examples of such solvents or diluents that may be mentioned are: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol or propanol; amides, such as N,N-dimethylformamide, N,N-diethylformamide, N,N-dimethylacetamide, N-methylpyrrolidone or hexamethylphosphoric acid triamide; nitriles, such as acetonitrile or propionitrile; and sulfoxides, such as dimethyl sulfoxide. If the reaction is carried out in the presence of a base, bases used in excess, such as triethylamine, pyridine, N-methylmorpholine or N,N-diethylaniline, may also serve as solvents or diluents.

The reaction is advantageously carried out in a temperature range from approximately 0° C. to approximately +120° C., preferably from approximately 0° C. to approximately +40° C.

In a preferred form, a compound of formula VIII is reacted at from 0° C. to approximately +40° C., preferably at room temperature, in an inert solvent, preferably an ether, especially tert-butyl methyl ether, with formic acid methyl ester.

Variant h):

Suitable bases for facilitating the reaction are, for example, alkali metal or alkaline earth metal hydroxides, hydrides, amides, alkanolates, acetates, carbonates, dialkylamides or alkylsilylamides, or alkylamines, alkylenediamines, unsubstituted or N-alkylated, saturated or unsaturated cycloalkylamines, basic heterocycles, ammonium hydroxides and carbocyclic amines. The following may be mentioned by way of example: sodium hydroxide, hydride, amide, methanolate, acetate or carbonate, potassium tert-butanolate, hydroxide, carbonate or hydride, lithium diisopropylamide, potassium bis(trimethylsilyl) amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,5-diazabicyclo[5.4.0]undec-5-ene (DBU).

The reactants can be reacted with one another as such, i.e. without the addition of a solvent or diluent, for example in the melt. In most cases, however, the addition of an inert solvent or diluent or of a mixture thereof is advantageous. Examples of such solvents or diluents that may be mentioned are: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol or propanol; amides, such as N,N-dimethylformamide, N,N-diethylformamide, N,N-dimethylacetamide, N-methylpyrrolidone or hexamethylphosphoric acid triamide; nitriles, such as acetonitrile or propionitrile; and sulfoxides, such as dimethyl sulfoxide. If the reaction is carried out in the presence of a base, bases used in excess, such as triethylamine, pyridine, N-methylmorpholine or N,N-diethylaniline, may also serve as solvents or diluents.

The reaction is advantageously carried out in a temperature range from approximately 0° C. to approximately +120° C., preferably from approximately 0° C. to approximately +40° C.

In a preferred form, a compound of formula VIII is reacted at from 0° C. to approximately +40° C., preferably at room temperature, in an inert solvent, preferably an ether, especially 1,4-dioxane, with an alkyl nitrite, preferably isopentyl nitrite.

Variant i):

Suitable bases for facilitating the reaction are, for example, alkali metal or alkaline earth metal hydroxides, hydrides, amides, alkanolates, acetates, carbonates, dialkylamides or alkylsilylamides, or alkylamines, alkylenediamines, unsubstituted or N-alkylated, saturated or unsaturated cycloalkylamines, basic heterocycles, ammonium hydroxides and carbocyclic amines. The following may be mentioned by way of example: sodium hydroxide, hydride, amide, methanolate, acetate or carbonate, potassium tert-butanolate, hydroxide, carbonate or hydride, lithium diisopropylamide, potassium bis(trimethylsilyl) amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyl-trimethylammonium hydroxide and 1,5-diazabicyclo[5.4.0]undec-5-ene (DBU).

The reactants can be reacted with one another as such, i.e. without the addition of a solvent or diluent, for example in the melt. In most cases, however, the addition of an inert solvent or diluent or of a mixture thereof is advantageous. Examples of such solvents or diluents that may be mentioned are: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol or propanol; amides, such as N,N-dimethylformamide, N,N-diethylformamide, N,N-dimethylacetamide, N-methylpyrrolidone or hexamethylphosphoric acid triamide; nitriles, such as acetonitrile or propionitrile; and sulfoxides, such as dimethyl sulfoxide. If the reaction is carried out in the presence of a base, bases used in excess, such as triethylamine, pyridine, N-methylmorpholine or N,N-diethylaniline, may also serve as solvents or diluents.

The reaction is advantageously carried out in a temperature range from approximately 0° C. to approximately +120° C., preferably from approximately 0° C. to approximately +40° C.

In a preferred form, a compound of formula III is reacted at from 0° C. to approximately +120° C., preferably at room temperature, in an inert solvent, preferably N,N-dimethylformamide, in the presence of a base, preferably an inorganic base, especially sodium hydride, with a compound of formula XI.

Variant j):

Leaving groups are as defined under variant a).

Suitable halogenating agents are, for example, elemental chlorine or bromine, thionyl chloride, sulfur dichloride, sulfuryl chloride, phosphorus trichloride, phosphorus tribromide, phosphorus pentachloride or N-bromosuccinimide, preferably N-bromosuccinimide.

Suitable bases for facilitating the reaction are, for example, alkali metal or alkaline earth metal hydroxides, hydrides, amides, alkanolates, acetates, carbonates, dialkylamides or alkylsilylamides, or alkylamines, alkylenediamines, unsubstituted or N-alkylated, saturated or unsaturated cycloalkylamines, basic heterocycles, ammonium hydroxides and carbocyclic amines. The following may be mentioned by way of example: sodium hydroxide, hydride, amide, methanolate, acetate or carbonate, potassium tert-butanolate, hydroxide, carbonate or hydride, lithium diisopropylamide, potassium bis(trimethylsilyl) amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyl-trimethylammonium hydroxide and 1,5-diazabicyclo[5.4.0]undec-5-ene (DBU).

The reactants can be reacted with one another as such, i.e. without the addition of a solvent or diluent, for example In the melt. In most cases, however, the addition of an inert solvent or diluent or of a mixture thereof is advantageous. Examples of such solvents or diluents that may be mentioned are: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol or propanol; amides, such as N,N-dimethylformamide, N,N-diethylformamide, N,N-dimethylacetamide, N-methylpyrrolidone or hexamethylphosphoric acid triamide; nitriles, such as acetonitrile or propionitrile; and sulfoxides, such as dimethyl sulfoxide. If the reaction is carried out in the presence of a base, bases used in excess, such as triethylamine, pyridine, N-methylmorpholine or N,N-diethylaniline, may also serve as solvents or diluents.

The reaction is advantageously carried out in a temperature range from approximately 0° C. to approximately +120° C., preferably from approximately 0° C. to approximately +40° C.

In a preferred form, a compound of formula XII is reacted at from )° C. to approximately +120° C., preferably at room temperature, in an inert solvent, preferably dimethyl sulfoxide, in the presence of a base, preferably an inorganic base, especially potassium carbonate, with a compound of the formula $X_3R_9$, and the compound so obtainable is reacted with a halogenating agent, preferably N-bromosuccinimide.

The compounds of formulae I, II, III, IV, VII, VIII and IX may be in the form of one of the possible isomers or in the form of a mixture thereof, for example depending on the number of asymmetric carbon atoms and the absolute and relative configuration thereof they may be in the form of pure isomers, such as antipodes and/or diastereoisomers, or in the form of mixtures of isomers, such as mixtures of enantiomers, for example racemates, mixtures of diastereoisomers or mixtures of racemates; the invention relates both to the pure isomers and to all possible mixtures of isomers and this is to be understood hereinbefore and hereinafter, even if stereochemical details are not specifically mentioned in each case.

Mixtures of diastereoisomers and mixtures of racemates of compounds of formulae I, II, III, IV, VII, VIII and IX that are obtainable in accordance with the process depending upon the starting materials and procedures chosen, or by other means, can be separated on the basis of the physico-chemical differences between the constituents into the pure diastereoisomers or racemates in known manner, for example by fractional crystallisation, distillation and/or chromatography.

Correspondingly obtainable mixtures of enantiomers, such as racemates, can be separated into the optical antipodes by known methods, for example by recrystallisation from an optically active solvent, by chromatography on chiral adsorbents, for example high-pressure liquid chromatography (HPLC) on acetyl cellulose, with the aid of suitable microorganisms, by cleavage with specific immobilised enzymes, via the formation of inclusion compounds, for example using chiral crown ethers, in which case only one enantiomer is complexed.

Apart from by the separation of corresponding mixtures of isomers, it is possible according to the invention to obtain pure diastereoisomers or enantiomers also by generally known methods of diastereoselective or enantioselective synthesis, for example by carrying out the process according to the invention with starting materials having a correspondingly suitable stereochemistry.

Advantageously, the biologically more active isomer, for example enantiomer, or mixture of isomers, for example mixture of enantiomers, will be isolated or synthesised, insofar as the individual components have differing biological activity. The compounds of formulae I, II, III, IV, VII, VIII and IX also be obtained in the form of their hydrates and/or may include other solvents, for example solvents used, where appropriate, for the crystallisation of compounds in solid form.

The invention relates to all those forms of the process according to which a compound obtainable as starting material or intermediate at any stage of the process is used as starting material and all or some of the remaining steps are carried out, or a starting material is used in the form of a derivative or a salt and/or its racemates or antipodes or, especially, is formed under the reaction conditions.

In the process of the present invention there are preferably used those starting materials and intermediates which result in the compounds of formula I described at the beginning as being especially valuable.

The invention relates especially to the preparation processes described in Examples P1, P3, P5, P7 and P8.

The invention relates also to those starting materials and intermediates used according to the invention for the preparation of the compounds of formula I, especially those compounds of formulae II, III, IV, VII, VIII and IX, that are novel, to the use thereof and to processes for the preparation thereof. In particular, the compounds of formulae II, III, IV and IX can be prepared analogously to Examples P1, P3 and P7 and P8, respectively.

It has now been found that the compounds of formula I have a microbicidal spectrum that is especially advantageous for practical requirements in the control of phytopathogenic microorganisms, especially fungi. They have very advantageous curative, preventive and, in particular, systemic properties, and can be used in the protection of numerous cultivated plants. with the compounds of formula I it is possible to inhibit or destroy the pests which occur on plants or on parts of plants (the fruit, blossom, leaves, stems, tubers, roots) in different crops of useful plants, while at the same time parts of plants which grow later are also protected from phytopathogenic microorganisms.

The compounds of formula I can also be used as dressing agents for protecting seed (fruit, tubers, grains) and plant cuttings against fungal infection as well as against phytopathogenic fungi which occur in the soil.

Compounds of formula I are effective, for example, against the phytopathogenic fungi belonging to the following classes: Fungi imperfecti (especially Botrytis, also Pyricularia, Helminthosporium, Fusarium, Septoria, Cercospora, Cercosporella and Altemaria); Basidiomycetes (e.g. Rhizoctonia, Hemileia, Puccinia). They are also effective against the class of the Ascomycetes (e.g. Venturia and Erysiphe, Podosphaera, Monilinia, Uncinula), but especially against the class of the Oomycetes (e.g. Phytophthora, Peronospora, Bremia, Pythium, Plasmopara).

The compounds of formula I according to the invention are also valuable active ingredients in the field of animal pest control, while being well tolerated by warm-blooded animals, fish and plants. In particular, the compounds according to the invention are effective against insects and representatives of the order Acarina, such as those occurring on useful plants and ornamentals in agriculture and horticulture, especially in plantations of cotton, vegetables and fruit, and in forestry. The compounds of the invention are suitable especially for controlling insects and representatives of the order Acarina in crops of fruit and vegetables, especially for controlling plant-destructive insects, such as *Spodoptera littoralis, Heliothis virescens, Diabrotica balteata* and *Crocidolomia binotalis*. Further areas of use of the compounds of the invention are in the protection of stocks and materials and in the hygiene sector, especially in the protection of domestic animals and productive livestock. The compounds according to the invention are effective against all or individual development stages of normally sensitive pests, but also of resistant pests. The action of the compounds of the invention may manifest itself, for example, in the mortality of the pests, which occurs immediately or only after some time, for example during moulting, or in reduced oviposition and/or hatching rate.

The above-mentioned pests include:
of the order Lepidoptera, for example,

Acleris spp., Adoxophyes spp., Aegeria spp., Agrotis spp., *Alabama argillaceae*, Amylois spp., *Anticarsia gemmatalis*, Archips spp., Argyrotaenia spp., Autographa spp., *Busseola fusca, Cadra cautella, Carposina nipponensis*, Chilo spp., Choristoneura spp., *Clysia ambiguella*, Cnaphalocrocis spp., Cnephasia spp., Cochylis spp., Coleophora spp., *Crocidolomia binotalis, Cryptophlebia leucotreta*, Cydia spp., Diatraea spp., *Diparopsis castanea*, Earias spp., Ephestia spp., Eucosma spp., *Eupoecilia ambiguella*, Euproctis spp., Euxoa spp., Grapholita spp., *Hedya nubiferana*, Heliothis spp., *Hellula undalis, Hyphantria cunea, Keiferia*

*lycopersicella, Leucoptera scitella,* Uthocollethis spp., *Lobesia botrana,* Lymantria spp., Lyonetia spp., Malacosoma spp., *Mamestra brassicae, Manduca sexta,* Operophtera spp., *Ostrinia nubilalis,* Pammene spp., Pandemis spp., *Panolis flammea, Pectinophora gossypiella, Phthorimaea operculella, Pieris rapae,* Pieris spp., *Plutella xylostella,* Prays spp., Scirpophaga spp., Sesamia spp., Sparganothis spp., Spodoptera spp., Synanthedon spp., Thaumetopoea spp., Tortrix spp., Trichoplusiani and Yponomeuta spp.;
of the order Coleoptera, for example, Agriotes spp., Anthonomus spp., *Atomaria linearis, Chaetocnema tibialis,* Cosmopolites spp., Curculio spp., Dermestes spp., Diabrotica spp., Epilachna spp., Eremnus spp., *Leptinotarsa decemlineata,* Lissorhoptrus spp., Melolontha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.;
of the order Orthoptera, for example, Blatta spp., Blattella spp., Gryllotalpa spp., *Leucophaea maderae,* Locusta spp., Periplaneta spp. and Schistocerca spp.;
of the order Isoptera, for example, Reticulitermes spp.;
of the order Psocoptera, for example, Uposcelis spp.;
of the order Anoplura, for example, Haematopinus spp., Linognathus spp., Pediculus spp., Pemphigus spp. and Phylloxera spp.;
of the order Mallophaga, for example, Damalinea spp. and Trichodectes spp.;
of the order Thysanoptera, for example, Frankliniella spp., Hercinothrips spp., Taeniothrips spp., *Thrips palmi, Thrips tabaci* and *Scirtothrips aurantii;*
of the order Heteroptera, for example, Cimex spp., *Distantiella theobroma,* Dysdercus spp., Euchistus spp. Eurygaster spp. Leptocorisa spp., Nezara spp., Piesma spp., Rhodnius spp., *Sahlbergella singularis,* Scotinophara spp. and Triatoma spp.;
of the order Homoptera, for example,

*Aleurothrixus floccosus, Aleyrodes brassicae,* Aonidiella spp., Aphididae, Aphis spp., Aspidiotus spp., *Bemisia tabaci,* Ceroplaster spp., *Chrysomphalus aonidium, Chrysomphalus dictyospermi, Coccus hesperidum,* Empoasca spp., *Eriosoma larigerum,* Erythroneura spp., Gascardia spp., Laodelphax spp., *Lecanium corni,* Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., *Pulvinaria aethiopica,* Quadraspidiotus spp., Rhopalosiphum spp., Saissetia spp., Scaphoideus spp., Schizaphis spp., Sitobion spp., *Trialeurodes vaporariorum, Trioza erytreae* and *Unaspis citri;*
of the order Hymenoptera, for example, Acromyrmex, Atta spp., Cephus spp., Diprion spp., Diprionidae, *Gilpinia polytoma,* Hoplocampa spp., Lasius spp., *Monomorium pharaonis,* Neodiprion spp., Solenopsis spp. and Vespa spp.;
of the order Diptera, for example, Aedes spp., *Antherigona soccata, Bibio hortulanus, Calliphora erythrocephala,* Ceratitis spp., Chrysomyia spp., Culex spp., Cuterebra spp., Dacus spp., *Drosophila melanogaster,* Fannia spp., Gastrophilus spp., Glossina spp., Hypoderma spp., Hyppobosca spp., Uriomyza spp., Lucilia spp., Melanagromyza spp., Musca spp., Oestrus spp., Orseolia spp., *Oscinella frit, Pegomyia hyoscyami,* Phorbia spp., *Rhagoletis pomonella,* Sciara spp., Stomoxys spp., Tabanus spp., Tannia spp. and Tipula spp.;
of the order Siphonaptera, for example, Ceratophyllus spp. and *Xenopsylla cheopis* and
of the order Thysanura, for example,

*Lepisma saccharina,* and
of the order Acarina, for example,

*Acarus siro, Aceria sheldoni, Aculus schlechtendali,* Amblyomma spp., Argas spp., Boophilus spp., Brevipalpus spp., *Bryobia praetiosa,* Calipitrimerus spp., Chorioptes spp., *Dermanyssus gallinae, Eotetranychus carpini,* Eriophyes spp., Hyalomma spp., Ixodes spp., *Olygonychus pratensis,* Omithodoros spp., Panonychus spp., *Phyllocoptruta oleivora, Polyphagotarsonemus latus,* Psoroptes spp., Rhipicephalus spp., Rhizoglyphus spp., Sarcoptes spp., Tarsonemus spp. and Tetranychus spp.

The good pesticidal activity of the compounds according to the invention corresponds to a mortality of at least 50–60% of the mentioned pests.

The activity of the compounds of the invention and of the compositions comprising them can be substantially broadened and adapted to prevailing circumstances by the addition of other insecticides and/or acaricides. Examples of suitable additional active ingredients include representatives of the following classes of compounds: organophosphorus compounds, nitrophenols and derivatives, formamidines, ureas, carbamates, pyrethroids, chlorinated hydrocarbons, and Bacillus thuringiensis preparations.

The compounds according to the invention are used in unmodified form or preferably together with the adjuvants conventionally employed in formulation technology, and are therefore formulated in known manner, e.g. into emulsifiable concentrates, directly sprayable or dilutable solutions, dilute emulsions, wettable powders, soluble powders, dusts or granules, or by encapsulation in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures comprising the compound (active ingredient) and, where appropriate, solid or liquid adjuvants, are prepared in known manner, for example by intimately mixing and/or grinding the active ingredient with the adjuvants, such as extenders, e.g. solvents or solid carriers, or surface active compounds (surfactants).

Suitable solvents are, for example: aromatic hydrocarbons, preferably the fractions of alkylbenzenes containing 8 to 12 carbon atoms, such as xylene mixtures, alkylated naphthalenes, aliphatic or cycloaliphatic hydrocarbons, such as cyclohexane, paraffins or tetrahydronaphthalene, alcohols, such as ethanol, propanol or butanol, glycols and their ethers and esters, such as propylene glycol, dipropylene glycol ether, ethylene glycol or ethylene glycol monomethyl or monoethyl ether, ketones, such as cyclohexanone, isophorone or diacetone alcohol, strongly polar solvents, such as N-methyl-2-pyrrolidone, dimethyl sulfoxide or N,N-dimethylformamide, water and vegetable oils or epoxidised vegetable oils, such as rape oil, castor oil, coconut oil or soybean oil or epoxidised rape oil, castor oil, coconut oil or soybean oil, and, where appropriate, silicone oils.

The solid carriers used, e.g. for dusts and dispersible powders, are normally natural mineral fillers such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, such as pumice, broken brick, sepiolite or bentonite; and suitable nonsorbent carriers are calcite or sand. In addition, a great number of granulated materials of inorganic or organic nature can be used, especially dolomite or pulverised plant residues.

Depending on the nature of the compound to be formulated, suitable surface-active compounds are non-ionic, cationic and/or anionic surfactants having good emulsifying, dispersing and wetting properties. The term "surfactants" will also be understood as comprising mixtures of surfactants.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms In the alkyl moiety of the alkylphenols. Further suitable non-ionic surfactants are water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit. Representative examples of non-ionic surfactants are nonylphenol polyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates. Examples are stearyltrimethylammonium chloride and benzyl-di(2-chloroethyl) ethylammonium bromide.

Both water-soluble soaps and water-soluble synthetic surface-active compounds are suitable anionic surfactants. Suitable soaps are the alkali metal salts, alkaline earth metal salts and unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tall oil; mention may also be made of fatty acid methyltaurine salts. More frequently, however, synthetic surfactants are used, especially fatty sulfonates, fatty sulfates, sulfonated benzimidazole derivatives or alkylarylsulfonates. The fatty sulfonates or sulfates are usually in the form of alkali metal salts, alkaline earth metal salts or unsubstituted or substituted ammonium salts and generally contain a $C_8$–$C_{22}$ alkyl radical, which also includes the alkyl moiety of acyl radicals; there may be mentioned by way of example the sodium or calcium salt of lignosulfonic acid, of dodecyl sulfate or of a mixture of fatty alcohol sulfates obtained from natural fatty acids. These compounds also include the salts of sulfated and sulfonated fatty alcohol/ethylene oxide adducts. The sulfonated benzimidazole derivatives preferably contain 2 sulfonic acid groups and one fatty acid radical containing approximately 8 to 22 carbon atoms. Examples of alkylarylsulfonates are the sodium, calcium or triethanolammonium salts of dodecylbenzenesulfonic acid, dibutylnaphthalenesulfonic acid or of a condensate of naphthalenesulfonic acid and formaldehyde. Also suitable are corresponding phosphates, e.g. salts of the phosphoric acid ester of an adduct of p-nonylphenol with 4 to 14 mol of ethylene oxide, or phospholipids.

The surfactants listed above are to be regarded merely as examples; many other surfactants used in formulation technology that are suitable in accordance with the invention are described in the relevant literature.

The pesticidal compositions usually comprise 0.1 to 99%, preferably 0.1 to 95%, of active ingredient, and 1 to 99.9%, preferably 5 to 99.9%, of a solid or liquid adjuvant, it generally being possible for 0 to 25%, preferably 0.1 to 20%, of the composition to be surfactants (in each case percentages are by weight). Whereas commercial products will preferably be formulated as concentrates, the end user will normally employ dilute formulations which have considerably lower active ingredient concentrations. Typical rates of concentration are from 0.1 to 1000 ppm, preferably from 0.1 to 500 ppm, active ingredient. The rates of application per hectare are generally from 1 to 1000 g of active ingredient per hectare, preferably from 25 to 500 g/ha.

Preferred formulations have especially the following composition (throughout, percentages are by weight):

| Emulsifiable concentrates: | |
|---|---|
| active ingredient: | 1 to 90%, preferably 5 to 20% |
| surfactant: | 1 to 30%, preferably 10 to 20% |
| liquid carrier: | 5 to 94%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surfactant: | 1 to 40%, preferably 2 to 30% |
| Wettable powders: | |
| active ingredient: | 0.5 to 90%, preferably 1 to 80% |
| surfactant: | 0.5 to 20%, preferably 1 to 15% |
| solid carrier: | 5 to 95%, preferably 15 to 90% |
| Granules: | |
| active ingredient: | 0.5 to 30%, preferably 3 to 15% |
| solid carrier: | 99.5 to 70%, preferably 97 to 85% |

The compositions may also comprise further adjuvants, such as stabilisers, for example vegetable oils or epoxidised vegetable oils (e.g. epoxidised coconut oil, rape oil or soybean oil), antifoams, for example silicone oil, preservatives, viscosity regulators, binders and/or tackifiers, as well as fertilisers or other active ingredients for obtaining special effects.

The Examples that follow serve to illustrate the invention. They do not limit the invention. Temperatures are given in degrees Celsius.

PREPARATION EXAMPLES

Example P1/1

1-[4-(2,2-Dichlorocyclopropylmethoxy)-2,5-difluorophenyl]-propan-1-one 2-oxime (Compound No. 1.77 in Table 1)

a) Propionic acid (2,5-difluorophenyl) ester

At 0° C.–5° C., a solution of 100 g of 2,5-difluorophenol in 66.5 g of pyridine is added dropwise in the course of 2 hours to a solution of 71.2 g of propionic acid chloride in 800 ml of toluene and stirring is then carried out at room temperature for a further hour. The reaction mixture is then diluted with ethyl acetate, washed twice with water and once with saturated sodium chloride solution and the organic phase is separated off, dried with sodium sulfate and concentrated by evaporation in vacuo. The crude product is processed further without further purification.

b) 1-(2,5-Difluoro-4-hydroxyphenyl)-propan-1-one 117.9 g of propionic acid (2,5-difluorophenyl) ester are heated to 60° C. and then 169.1 g of aluminium trichloride are added in small portions. When the addition is complete, the reaction mixture is heated at 1 20° C. until the evolution of hydrogen chloride gas can no longer be observed. The mixture is then cooled to 50° C. and 400 ml of water are added dropwise, followed by approximately 100 ml of ethyl acetate. Extraction of the reaction mixture is carried out several times with ethyl acetate and the combined extracts are washed twice with water and once with saturated sodium chloride solution, dried with sodium sulfate and concentrated by evaporation in vacuo. Recrystallisation of the residue from ethyl acetate/hexane yields 1-(2,5-difluoro-4-hydroxyphenyl)-propan-1-one having a melting point of 116-11 7° C.

c) 1-[4-(2,2-Dichlorocyclopropylmethoxy)-2,5-difluorophenyl]-propan-1-one 40.3 g of 2-bromomethyl-1,1-dichlorocyclopropane are added dropwise at room temperature to a suspension of 29 g of 1-(2,5-difluoro-4-hydroxyphenyl)-propan-1-one, 28.6 g of potassium carbonate and 0.5 g of potassium iodide in 95 ml of N,N-dimethylformamide. The reaction mixture is then stirred at 90° C. for 1.5 hours, cooled and poured into ice-water.

The product which precipitates is filtered off and dissolved in ethyl acetate and the solution is washed twice with water and once with saturated sodium chloride solution, dried with sodium sulfate and concentrated by evaporation in vacuo. The crude product is made into a slurry in cold hexane, filtered and dried in vacuo, yielding 1-[4-(2,2-dichlorocyclopropylmethoxy)-2,5-difluorophenyl]-propan-1-one having a melting point of 89–91° C.

d) 1-[4-(2,2-Dichlorocyclopropylmethoxy)-2,5-difluorophenyl]-propan-1-one 2-oxime Hydrogen chloride gas is introduced into 350 ml of dioxane for 2 minutes and then 43.5 g of (2,2-dichlorocyclopropylmethoxy)-2,5-difluorophenyl]-propan-1-one, followed, dropwise, by 19.8 g of isopentyl nitrite, are added. The reaction mixture is stirred at room temperature for 24 hours and then hydrogen chloride gas is again introduced for 2 minutes and the reaction mixture is stirred for a further 30 hours at room temperature. The mixture is then rendered basic with triethylamine and concentrated by evaporation in vacuo. The residue is dissolved in ethyl acetate and the solution is washed twice with water and once with saturated sodium chloride solution, dried with sodium sulfate and concentrated by evaporation in vacuo. Purification by flash chromatography (silica gel, ethyl acetate/hexane 1:3) yields the title compound having a melting point of 74–76° C.

Example P1/2

1-[4-(4-Chlorophenoxy)-2-fluorophenyl]-propan-1-one 2-oxime (Compound No. 1.57)

a) At room temperature, 12.9 g (0.1 mol) of 4-chlorophenol are stirred vigorously for 1 hour with 20.7 g (0.15 mol) of potassium carbonate in 150 ml of N,N-dimethylacetamide. 17.0 g (0.1 mol) of 2,4-difluorophenyl-propane-1-one are added and the reaction mixture is stirred for 2–3 hours at a bath temperature of 130–140° C. The reaction mixture is cooled to 25° C. and the solvent is distilled off under a high vacuum. The residue is taken up in ether and washed with water, 10% KOH solution and brine. The organic phase is dried over sodium sulfate and concentrated by evaporation in vacuo. An oil is obtained which, according to the NMR-Spectrum, consists of 34% 1-[4-(4-chlorophenoxy)-2-fluorophenyl]-propan-1-one.

b) 23.0 g of a mixture comprising approximately 34% 1-[4-(4-chlorophenoxy)-2-fluoro-phenyl]propan-1-one are dissolved in 250 ml of ether. At a temperature of 20-30° C, dry hydrogen chloride is introduced for 15 minutes. Then 11.5 g (99 mmol) of isopentyl nitrite are added dropwise in such a manner that the temperature does not exceed 25° C. The reaction mixture is then stirred at room temperature for 18 hours. The mixture is discharged into 500 ml of ice-water and the organic phase is separated off. The ether phase is washed neutral with water and dried with brine and sodium sulfate. Concentration by evaporation in vacuo yields a crude product which is chromatographed on silica gel with ethyl acetate admixed with 3–8% hexane, under a pressure of 1.2 bar, yielding an oil which consists of the title compound and the starting material, 1-[4-(4-chlorophenoxy)-2-fluorophenyl]-propan-1-one.

Example P2

The other compounds listed in Table 1 can also be prepared n a manner analogous to that described in Example P1. cProp denotes cyclopropyl. In the "Phys. data" column of this Table the figures represent the melting point in °C.

TABLE 1

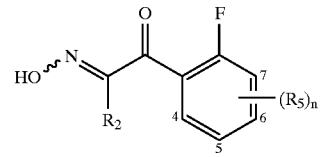

| Compound No. | $R_2$ | $(R_5)n$ | Phys. data |
|---|---|---|---|
| 1.1 | $CH_3$ | H | |
| 1.2 | $CH_3$ | 6-$OCH_3$ | |
| 1.3 | $CH_3$ | 6-$OCH_2$(cProp-$Cl_2$(2,2)) | resin |
| 1.4 | $CH_3$ | 6-$OCH_2C_6H_4CF_3$(3) | 118–121° |
| 1.5 | $CH_3$ | 6-$OCH_2CH=CH_2$ | |
| 1.6 | $CH_3$ | 6-$OCH_2C\equiv CH$ | |
| 1.7 | $CH_3$ | 6-$OCH_2C_5H_4CF_3$(4) | |
| 1.8 | $CH_3$ | 6-$OCH_2C_6H_4CF_3$(2) | |
| 1.9 | $CH_3$ | 5-$OCH_3$ | |
| 1.10 | $CH_3$ | 6-$OCH_2CH=CCl_2$ | |
| 1.11 | $CH_3$ | 6-$OCF_2CHFCF_3$ | 75–76° |
| 1.12 | $CH_3$ | 6-$OCF_2CF_2CF_3$ | |
| 1.13 | $CH_3$ | 4-F | 80–81° |
| 1.14 | $CH_3$ | 5-F | 93–95° |
| 1.15 | $CH_3$ | 6-F | |
| 1.16 | $CH_3$ | 7-F | 101° |
| 1.17 | $CH_3$ | 4-Cl | |
| 1.18 | $CH_3$ | 5-Cl | |
| 1.19 | $CH_3$ | 6-Cl | |
| 1.20 | $CH_3$ | 7-Cl | |
| 1.21 | $CH_3$ | 4-$CH_3$ | |
| 1.22 | $CH_3$ | 5-$CH_3$ | |
| 1.23 | $CH_3$ | 6-$CH_3$ | |
| 1.24 | $CH_3$ | 7-$CH_3$ | |
| 1.25 | $CH_3$ | 4-$CF_3$ | |
| 1.26 | $CH_3$ | 5-$CF_3$ | |
| 1.27 | $CH_3$ | 6-$CF_3$ | 92° |
| 1.28 | $CH_3$ | 7-$CF_3$ | |
| 1.29 | $CH_3$ | 6-$OCF_2CHF_2$ | |
| 1.30 | $CH_3$ | 6-$OCF_2CHFCl$ | |
| 1.31 | $CH_3$ | 6-$OCF_2CHFBr$ | |

TABLE 1-continued

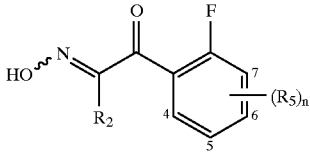

| Compound No. | R₂ | (R₅)n | Phys. data |
|---|---|---|---|
| 1.32 | $CH_3$ | 6-$OCHF_2$ | |
| 1.33 | $CH_3$ | 6-$OCF_2Br$ | |
| 1.34 | $CH_3$ | 6-$OCF_3$ | |
| 1.35 | $CH_3$ | 6-$OCH_2$(cProp-$Br_2$(2,2)) | resin |
| 1.36 | $CH_3$ | 6-$OCH_2$(cProp-$CH_3$(1)-$Cl_2$(2,2)) | 93–94° |
| 1.37 | $CH_3$ | 6-$OCH_2C(CH_3)=CH_2$ | |
| 1.38 | $CH_3$ | 6-$OCH_2CH_3$ | |
| 1.39 | $CH_3$ | 6-$OCH_2CH_2CH_3$ | |
| 1.40 | $CH_3$ | 6-$OCH_2CH_2CH_2CH_3$ | |
| 1.41 | $CH_3$ | 6-$OCH_2C_6H_5$ | |
| 1.42 | $CH_3$ | 6-$OCH_2C_6H_4F$(2) | |
| 1.43 | $CH_3$ | 6-$OCH_2C_6H_4F$(3) | |
| 1.44 | $CH_3$ | 6-$OCH_2C_6H_4F$(4) | 138–140° |
| 1.45 | $CH_3$ | 6-$OCH_2C_6H_4Cl$(2) | |
| 1.46 | $CH_3$ | 6-$OCH_2C_6H_4Cl$(3) | |
| 1.47 | $CH_3$ | 6-$OCH_2C_6H_4Cl$(4) | |
| 1.48 | $CH_3$ | 6-$OCH_2C_6H_4Br$(4) | |
| 1.49 | $CH_3$ | 6-$OCH_2C_6H_4OCH_3$(4) | |
| 1.50 | $CH_3$ | 6-$OCH_2C_6H_3F_2$(2,6) | |
| 1.51 | $CH_3$ | 6-$OCH_2C_6H_3F_2$(2,4) | |
| 1.52 | $CH_3$ | 6-$OCH_2C_6H_3F_2$(3,4) | |
| 1.53 | $CH_3$ | 6-$OCH_2C_6H_3Cl_2$(2,6) | |
| 1.54 | $CH_3$ | 6-$OCH_2C_6H_3Cl_2$(2,4) | |
| 1.55 | $CH_3$ | 6-$OCH_2C_6H_3Cl_2$(3,4) | |
| 1.56 | $CH_3$ | 6-$OC_6H_5$ | |
| 1.57 | $CH_3$ | 6-$OC_6H_4Cl$(4) | oil |
| 1.58 | $CH_3$ | 6-$OC_6H_4F$(4) | |
| 1.59 | $CH_3$ | 6-$OC_6H_4CN$(4) | |
| 1.60 | $CH_3$ | 6-$OC_6H_4OCH_3$(4) | |
| 1.61 | $CH_3$ | 6-$OC_6H_4CF_3$(4) | |
| 1.62 | $C_2H_5$ | H | |
| 1.63 | $C_2H_5$ | 6-$OCH_2$(cProp-$Cl_2$(2,2)) | |
| 1.64 | $C_2H_5$ | 6-$OCH_2C_6H_4F$(4) | |
| 1.65 | n-propyl | H | |
| 1.66 | n-propyl | 6-$OCH_2$(cProp-$Cl_2$(2,2)) | |
| 1.67 | n-propyl | 6-$OCH_2C_6H_4F$(4) | |
| 1.68 | CN | H | |
| 1.69 | CN | 6-$OCH_2$(cProp-$Cl_2$(2,2)) | |
| 1.70 | CN | 6-$OCH_2C_6H_4F$(4) | |
| 1.71 | CN | 6-$OCH_2C_6H_4CF_3$(3) | |
| 1.72 | CN | 6-$OCF_2CHFCF_3$ | |
| 1.73 | CN | 6-$OCH_2CH=CCl_2$ | |
| 1.74 | $SCF_3$ | H | |
| 1.75 | $CF_3$ | H | |
| 1.76 | $CH_3$ | 5-F,6-$OCH_3$ | |
| 1.77 | $CH_3$ | 5-F,6-$OCH_2$(cProp-$Cl_2$(2,2)) | 74–76° |
| 1.78 | $CH_3$ | 5-F,6-$OCH_2C_6H_4F$(4) | 101–103° |
| 1.79 | $CH_3$ | 5-F,6-$OCH_2C_6H_4Cl$(4) | |
| 1.80 | $CH_3$ | 5-F,6-$OCH_2C_6H_4CF_3$(4) | |
| 1.81 | $CH_3$ | 5-F,6-$OCH_2C_6H_4CF_3$(3) | 131–134° |
| 1.82 | $CH_3$ | 5-F,6-$OCH_2C_6H_4CF_3$(2) | |
| 1.83 | $CH_3$ | 5-F,6-$OCF_2CHFCF_3$ | |
| 1.84 | $CH_3$ | 5-F,6-$OCF_2CHF_2$ | |
| 1.85 | $CH_3$ | 5-F,6-$OCHF_2$ | |
| 1.86 | $CH_3$ | 5-F,6-$OCF_3$ | |
| 1.87 | $CH_3$ | 5-Cl,6-$OCH_3$ | |
| 1.88 | $CH_3$ | 5-Cl,6-$OCH_2C_6H_4CF_3$(4) | |
| 1.89 | $CH_3$ | 5-Cl,6-$OCH_2C_6H_4CF_3$(3) | |
| 1.90 | $CH_3$ | 5-Cl,6-$OCH_2C_6H_4CF_3$(2) | |
| 1.91 | $CH_3$ | 5-Cl,6-$OCH_2$(cProp-$Cl_2$(2,2)) | |
| 1.92 | $CH_3$ | 5-Br,6-$OCH_2C_6H_4CF_3$(3) | |
| 1.93 | $CH_3$ | 5-Br,6-$OCH_2$(cProp-$Cl_2$(2,2)) | |
| 1.94 | $CH_3$ | 6-$OCH_2$-Si$(CH_3)_3$ | 94–96° |
| 1.95 | cProp | H | |
| 1.96 | cProp | 6-$OCH_2$(cProp-$Cl_2$(2,2)) | |
| 1.97 | cProp | 6-$OCH_2C_6H_4F$(4) | |
| 1.98 | $CH_3$ | 6-$OCH(CH_3)_2$ | |
| 1.99 | $CH_3$ | 6-$OC(CH_3)_3$ | |

TABLE 1-continued

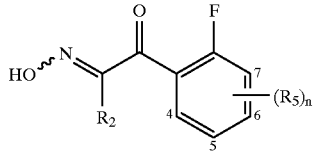

| Compound No. | R₂ | (R₅)n | Phys. data |
|---|---|---|---|
| 1.100 | $CH_3$ | 6-$OCH_2CH(CH_3)_2$ | |
| 1.101 | $CH_3$ | 6-$OCH(CH_3)CH_2CH_3$ | |
| 1.102 | $CH_3$ | 6-$OC_6H_4CF_3$(2) | |
| 1.103 | $CH_3$ | 6-$OC_6H_4CF_3$(3) | |
| 1.104 | $CH_3$ | 6-$OC_6H_4Br$(4) | |
| 1.105 | $CH_3$ | 6-$OC_6H_3F_2$(2,4) | |

Example P3/1

1-[6-(2,2-Dichlorocyclopropylmethoxy)-5-fluoro-1-methyl-1H-indazol-3-yl]-ethanone Oxime (Compound No. 2.77 in Table 2)

A mixture of 3.4 g of 1-[4-(2,2-dichlorocyclopropylmethoxy)-2,5-difluorophenyl]-propan-1-one 2-oxime and 10 ml of methylhydrazine are stirred at 100° C. for 3 hours and then at 140° C. for 20 hours. After cooling, water is added to the reaction mixture and extraction is carried out twice with ethyl acetate. The combined organic phases are washed twice with water and once with saturated sodium chloride solution, dried with sodium sulfate and concentrated by evaporation in vacuo. Purification by flash chromatography (silica gel, ethyl acetate/hexane 1:1) yields the title compound having a melting point of 150–152° C.

Example P3/2

1-[6-(4-Chlorophenoxy)-1-methyl-1H-indazol-3-yl]-ethanone Oxime (Compound No. 2.57)

21.2 g of the mixture described in Example P1/2 are stirred with 30 ml of methylhydrazine at 100° C. for 18 hours. The reaction mixture is cooled to 25° C., poured into 300 ml of ice-water and stirred for 1 hour. The crystals which precipitate are dissolved in ethyl acetate and washed with water and brine, dried over sodium sulfate and concentrated by evaporation in vacuo. The crude product is chromatographed on silica gel with ethyl acetate admixed with from 5 to 15% hexane, under a pressure of 1.2 bar, yielding the title compound having a melting point of 148–150° C.

Example P4

The other compounds listed in Table 2 can also be prepared in a manner analogous to that described in Example P3. cProp denotes cyclopropyl. In the "Phys. data" column of this Table the figures represent the melting point in °C.

TABLE 2

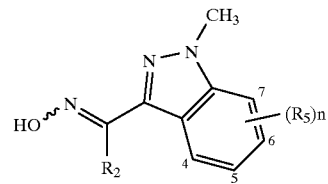

| Compound No. | $R_2$ | $(R_5)n$ | Phys. data |
|---|---|---|---|
| 2.1 | $CH_3$ | H | 132–134° |
| 2.2 | $CH_3$ | 6-$OCH_3$ | 135–142° |
| 2.3 | $CH_3$ | 6-$OCH_2$(cProp-$Cl_2$(2,2)) | 168–170° |
| 2.4 | $CH_3$ | 6-$OCH_2C_6H_4CF_3$(3) | 185–188° |
| 2.5 | $CH_3$ | 6-$OCH_2CH=CH_2$ | |
| 2.6 | $CH_3$ | 6-$OCH_2C\equiv CH$ | |
| 2.7 | $CH_3$ | 6-$OCH_2C_6H_4CF_3$(4) | |
| 2.8 | $CH_3$ | 6-$OCH_2C_6H_4CF_3$(2) | |
| 2.9 | $CH_3$ | 5-$OCH_3$ | |
| 2.10 | $CH_3$ | 6-$OCH_2CH=CCl_2$ | |
| 2.11 | $CH_3$ | 6-$OCF_2CHFCF_3$ | 145–146° |
| 2.12 | $CH_3$ | 6-$OCF_2CF_2CF_3$ | |
| 2.13 | $CH_3$ | 4-F | |
| 2.14 | $CH_3$ | 5-F | |
| 2.15 | $CH_3$ | 6-F | 151° |
| 2.16 | $CH_3$ | 7-F | |
| 2.17 | $CH_3$ | 4-Cl | |
| 2.18 | $CH_3$ | 5-Cl | |
| 2.19 | $CH_3$ | 6-Cl | |
| 2.20 | $CH_3$ | 7-Cl | |
| 2.21 | $CH_3$ | 4-$CH_3$ | |
| 2.22 | $CH_3$ | 5-$CH_3$ | |
| 2.23 | $CH_3$ | 6-$CH_3$ | |
| 2.24 | $CH_3$ | 7-$CH_3$ | |
| 2.25 | $CH_3$ | 4-$CF_3$ | |
| 2.26 | $CH_3$ | 5-$CF_3$ | |
| 2.27 | $CH_3$ | 6-$CF_3$ | 156° |
| 2.28 | $CH_3$ | 7-$CF_3$ | |
| 2.29 | $CH_3$ | 6-$OCF_2CHF_2$ | |
| 2.30 | $CH_3$ | 6-$OCF_2CHFCl$ | |
| 2.31 | $CH_3$ | 6-$OCF_2CHFBr$ | |
| 2.32 | $CH_3$ | 6-$OCHF_2$ | |
| 2.33 | $CH_3$ | 6-$OCF_2Br$ | |
| 2.34 | $CH_3$ | 6-$OCF_3$ | |
| 2.35 | $CH_3$ | 6-$OCH_2$(cProp-$Br_2$(2,2)) | 168–170° |
| 2.36 | $CH_3$ | 6-$OCH_2$(cProp-$CH_2$(1)-$Cl_2$(2,2)) | resin |
| 2.37 | $CH_3$ | 6-$OCH_2C(CH_3)=CH_2$ | |
| 2.38 | $CH_3$ | 6-$OCH_2CH_3$ | |
| 2.39 | $CH_3$ | 6-$OCH_2CH_2CH_3$ | |
| 2.40 | $CH_3$ | 6-$OCH_2CH_2CH_2CH_3$ | |
| 2.41 | $CH_3$ | 6-$OCH_2C_6H_5$ | |
| 2.42 | $CH_3$ | 6-$OCH_2C_6H_4F$(2) | |
| 2.43 | $CH_3$ | 6-$OCH_2C_6H_4F$(3) | |
| 2.44 | $CH_3$ | 6-$OCH_2C_6H_4F$(4) | 161–163° |
| 2.45 | $CH_3$ | 6-$OCH_2C_6H_4Cl$(2) | |
| 2.46 | $CH_3$ | 6-$OCH_2C_6H_4Cl$(3) | |
| 2.47 | $CH_3$ | 6-$OCH_2C_6H_4Cl$(4) | |
| 2.48 | $CH_3$ | 6-$OCH_2C_6H_4Br$(4) | |
| 2.49 | $CH_3$ | 6-$OCH_2C_6H_4OCH_3$(4) | |
| 2.50 | $CH_3$ | 6-$OCH_2C_6H_3F_2$(2,6) | |
| 2.51 | $CH_3$ | 6-$OCH_2C_6H_3F_2$(2,4) | |
| 2.52 | $CH_3$ | 6-$OCH_2C_6H_3F_2$(3,4) | |
| 2.53 | $CH_3$ | 6-$OCH_2C_6H_3Cl_2$(2,6) | |
| 2.54 | $CH_3$ | 6-$OCH_2C_6H_3Cl_2$(2,4) | |
| 2.55 | $CH_3$ | 6-$OCH_2C_6H_3Cl_2$(3,4) | |
| 2.56 | $CH_3$ | 6-$OC_6H_5$ | |
| 2.57 | $CH_3$ | 6-$OC_6H_4Cl$(4) | 148–150° |
| 2.58 | $CH_3$ | 6-$OC_6H_4F$(4) | |
| 2.59 | $CH_3$ | 6-$OC_6H_4CN$(4) | |
| 2.60 | $CH_3$ | 6-$OC_6H_4OCH_3$(4) | |
| 2.61 | $CH_3$ | 6-$OC_6H_4CF_3$(4) | |
| 2.62 | $C_2H_5$ | H | |
| 2.63 | $C_2H_5$ | 6-$OCH_2$(cProp-$Cl_2$(2,2)) | |
| 2.64 | $C_2H_5$ | 6-$OCH_2C_6H_4F$(4) | |
| 2.65 | n-propyl | H | |
| 2.66 | n-propyl | 6-$OCH_2$(cProp-$Cl_2$(2,2)) | |

TABLE 2-continued

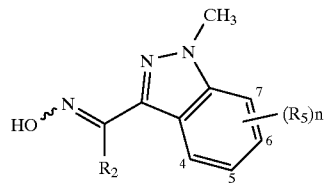

| Compound No. | $R_2$ | $(R_5)n$ | Phys. data |
|---|---|---|---|
| 2.67 | n-propyl | 6-$OCH_2C_6H_4F$(4) | |
| 2.68 | CN | H | |
| 2.69 | CN | 6-$OCH_2$(cProp-$Cl_2$(2,2)) | |
| 2.70 | CN | 6-$OCH_2C_6H_4F$(4) | |
| 2.71 | CN | 6-$OCH_2C_6H_4CF_3$(3) | |
| 2.72 | CN | 6-$OCF_2CHFCF_3$ | |
| 2.73 | CN | 6-$OCH_2CH=CCl_2$ | |
| 2.74 | $SCF_3$ | H | |
| 2.75 | $CF_3$ | H | |
| 2.76 | $CH_3$ | 5-F,6-$OCH_3$ | |
| 2.77 | $CH_3$ | 5-F,6-$OCH_2$(cProp-$Cl_2$(2,2)) | 150–152° |
| 2.78 | $CH_3$ | 5-F,6-$OCH_2C_6H_4F$(4) | 158–160° |
| 2.79 | $CH_3$ | 5-F,6-$OCH_2C_6H_4Cl$(4) | |
| 2.80 | $CH_3$ | 5-F,6-$OCH_2C_6H_4CF_3$(4) | |
| 2.81 | $CH_3$ | 5-F,6-$OCH_2C_6H_4CF_3$(3) | 208–210° |
| 2.82 | $CH_3$ | 5-F,6-$OCH_2C_6H_4CF_3$(2) | |
| 2.83 | $CH_3$ | 5-F,6-$OCF_2CHFCF_3$ | |
| 2.84 | $CH_3$ | 5-F,6-$OCF_2CHF_2$ | |
| 2.85 | $CH_3$ | 5-F,6-$OCHF_2$ | |
| 2.86 | $CH_3$ | 5-F,6-$OCF_3$ | |
| 2.87 | $CH_3$ | 5-Cl,6-$OCH_3$ | |
| 2.88 | $CH_3$ | 5-Cl,6-$OCH_2C_6H_4CF_3$(4) | |
| 2.89 | $CH_3$ | 5-Cl,6-$OCH_2C_6H_4CF_3$(3) | |
| 2.90 | $CH_3$ | 5-Cl,6-$OCH_2C_6H_4CF_3$(2) | |
| 2.91 | $CH_3$ | 5-Cl,6-$OCH_2$(cProp-$Cl_2$(2,2)) | |
| 2.92 | $CH_3$ | 5-Br,6-$OCH_2C_6H_4CF_3$(3) | |
| 2.93 | $CH_3$ | 5-Br,6-$OCH_2$(cProp-$Cl_2$(2,2)) | |
| 2.94 | $CH_3$ | 6-$OCH_2$-$Si(CH_3)_3$ | 172–174° |
| 2.95 | cProp | H | |
| 2.96 | cProp | 6-$OCH_2$(cProp-$Cl_2$(2,2)) | |
| 2.97 | cProp | 6-$OCH_2C_6H_4F$(4) | |
| 2.98 | $CH_3$ | 6-$OCH(CH_3)_2$ | |
| 2.99 | $CH_3$ | 6-$OC(CH_3)_3$ | |
| 2.100 | $CH_3$ | 6-$OCH_2CH(CH_3)_2$ | |
| 2.101 | $CH_3$ | 6-$OCH(CH_3)CH_2CH_3$ | |
| 2.102 | $CH_3$ | 6-$OC_6H_4CF_3$(2) | |
| 2.103 | $CH_3$ | 6-$OC_6H_4CF_3$(3) | |
| 2.104 | $CH_3$ | 6-$OC_6H_4Br$(4) | |
| 2.105 | $CH_3$ | 6-$OC_6H_3F_2$(2,4) | |
| 2.106 | $CH_3$ | 6-$OC_6H_3Cl_2$(3,4) | 156–157° |
| 2.107 | $CH_3$ | 6-$OC_6H_4$—$OCF_3$(4) | |
| 2.108 | $CH_3$ | 6-$OC_6H_3Cl_2$(2,4) | |
| 2.109 | $CH_3$ | 6-$OC_6H_4F$(2) | |
| 2.110 | $CH_3$ | 6-$OC_6H_4$-(4-$OC_6H_5$) | |
| 2.111 | $CH_3$ | 6-$OC_6F_5$ | |

Example P5/1

2-[[[(1-{6-[(2,2-Dichlorocyclopropyl)methoxy]-5-fluoro-1-methylindazol-3-yl}ethylidene)amino]oxy]methyl]-α-(methoxymethylene)phenylacetic Acid Methyl Ester (Compound No. 3.77)

A solution of 0.9 g of 1-[6-(2,2-dichlorocyclopropylmethoxy)-5-fluoro-1-methyl-1H-indazol-3-yl]-ethanone oxime in 10 ml of N,N-dimethylformamide is added dropwise to a suspension of 0.2 g of sodium hydride in 15 ml of N,N-dimethylformamide and the reaction mixture is stirred at room temperature for 15 minutes. Then 1.04 g of 2-(α-bromo-o-tolyl)-3-methoxyacrylic acid methyl ester in 10 ml of N,N-dimethylformamide are added dropwise and the reaction mixture is stirred at room temperature for a further 3 hours.

The mixture is then acidified with acetic acid and concentrated by evaporation in vacuo at approx. 50° C. The residue is dissolved in ethyl acetate and the solution is washed twice with water and once with saturated sodium chloride solution, dried with sodium sulfate and concentrated by evaporation in vacuo. Purification by flash chromatography (silica gel, ethyl acetate/hexane 1:1) yields the title compound having a melting point of 138–140° C.

Example P5/2

2-(2-{1-[6-(4-Chlorophenoxy)-1-methyl-1H-indazol-3-yl]-ethylideneaminooxymethyl}-phenyl)-3-methoxyacrylic Acid Methyl Ester (Compound No. 3.57)

3.7 g of the compound 1-[6-(4-chlorophenoxy)-1-methyl-1H-indazol-3-yl]-ethanone oxime are dissolved in 15 ml of dry dimethylformamide and added dropwise to a suspension of 560 mg of sodium hydride in 15 ml of DMF. With slight evolution of hydrogen, the reaction mixture is stirred for 30 minutes at room temperature and for 1 hour at 50° C. The reaction mixture is cooled to 25° C. and then 3.33 g (11.7 mmol) of 2-(α-bromo-o-tolyl)-3-methoxyacrylic acid methyl ester dissolved in 15 ml of DMF are added dropwise, the temperature rising to 37° C. The reaction mixture is stirred at room temperature for 3 hours and then neutralised with glacial acetic acid. The reaction mixture is then concentrated by evaporation under a high vacuum and the residue is taken up in ethyl acetate, washed with water and brine, dried over sodium sulfate and concentrated by evaporation in vacuo. The crude product is chromatographed on silica gel with ethyl acetate admixed with from 5 to 20% hexane, at 1.2 bar. Ether and hexane are added, yielding the title compound having a melting point of 124–125° C.

Example P5/3

(2-{1-[6-(4-Chlorophenoxy)-1-methyl-1H-indazol-3-yl]-ethylideneaminooxime-ethyl}-phenyl)-methoxyiminoacetic Acid Methyl Ester (Compound No. 4.57)

681 mg of sodium hydride are suspended in 20 ml of dry dimethylformamide. At room temperature, a solution of 4.5 g of the compound 1-[6-(4-chlorophenoxy)-1-methyl-1H-indazol-3-yl]-ethanone oxime in 15 ml of DMF is added dropwise. With slight evolution of hydrogen, the reaction mixture is stirred for 30 minutes at room temperature and for 1 hour at 50° C. The reaction mixture is cooled to 25° C. and a solution of 4.06 g of 2-(2-bromomethyl-phenyl)glyoxylic acid methyl ester O-methyloxime in 15 ml of DMF is added dropwise. The reaction mixture is stirred for 3 hours, neutralised with glacial acetic acid and then concentrated by evaporation under a high vacuum. The residue is taken up in ethyl acetate, washed with water and brine, dried over sodium sulfate and concentrated by evaporation. The crude product is chromatographed on silica gel with ethyl acetate admixed with from 5 to 20% hexane, at 1.2 bar. Ether and hexane are added, yielding the title compound having a melting point of 95–96° C.

Example P5/4

2-(2-{1-[6-(4-Chlorophenoxy)-1-methyl-1H-indazol-3yl]-ethylideneaminooxymethyl}phenyl)-2-methoxyimino-N-methylacetamide (Compound No. 5.57)

3.0 g of Compound 4.57 are dissolved in 10 ml of ethanol and 20 ml of DMF. 2.2 ml of methylamine (8 ml/l in ethanol) are added thereto. The solution is left to stand at room temperature for 2 days and then concentrated completely by evaporation. Hexane is added, yielding the title compound having a melting point of 137–138° C.

Example P6

The other compounds listed in Tables 3 to 11 can also be prepared in a manner analogous to that described in Example P5. cProp denotes cyclopropyl. In the "Phys. data" column of those Tables the figures represent the melting point in °C.

TABLE 3

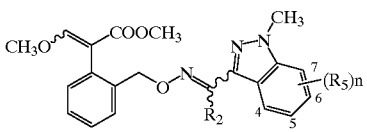

| Compound No. | $R_2$ | $(R_5)n$ | Phys. data |
|---|---|---|---|
| 3.1 | $CH_3$ | H | 103–105° |
| 3.2 | $CH_3$ | 6-$OCH_3$ | 107–110° |
| 3.3 | $CH_3$ | 6-$OCH_2$(cProp-$Cl_2$(2,2)) | resin |
| 3.4 | $CH_3$ | 6-$OCH_2C_6H_4CF_3$(3) | 136–139° |
| 3.5 | $CH_3$ | 6-$OCH_2CH=CH_2$ | |
| 3.6 | $CH_3$ | 6-$OCH_2C\equiv CH$ | |
| 3.7 | $CH_3$ | 6-$OCH_2C_6H_4CF_3$(4) | |
| 3.8 | $CH_3$ | 6-$OCH_2C_6H_4CF_3$(2) | |
| 3.9 | $CH_3$ | 5-$OCH_3$ | |
| 3.10 | $CH_3$ | 6-$OCH_2CH=CCl_2$ | |
| 3.11 | $CH_3$ | 6-$OCF_2CHFCF_3$ | resin |
| 3.12 | $CH_3$ | 6-$OCF_2CF_2CF_3$ | |
| 3.13 | $CH_3$ | 4-F | |
| 3.14 | $CH_3$ | 5-F | |
| 3.15 | $CH_3$ | 6-F | 114° |
| 3.16 | $CH_3$ | 7-F | |
| 3.17 | $CH_3$ | 4-Cl | |
| 3.18 | $CH_3$ | 5-Cl | |
| 3.19 | $CH_3$ | 6-Cl | |
| 3.20 | $CH_3$ | 7-Cl | |
| 3.21 | $CH_3$ | 4-$CH_3$ | |
| 3.22 | $CH_3$ | 5-$CH_3$ | |
| 3.23 | $CH_3$ | 6-$CH_3$ | |
| 3.24 | $CH_3$ | 7-$CH_3$ | |
| 3.25 | $CH_3$ | 4-$CF_3$ | |
| 3.26 | $CH_3$ | 5-$CF_3$ | |
| 3.27 | $CH_3$ | 6-$CF_3$ | |
| 3.28 | $CH_3$ | 7-$CF_3$ | |
| 3.29 | $CH_3$ | 6-$OCF_2CHF_2$ | |
| 3.30 | $CH_3$ | 6-$OCF_2CHFCl$ | |
| 3.31 | $CH_3$ | 6-$OCF_2CHFBr$ | |
| 3.32 | $CH_3$ | 6-$OCHF_2$ | |
| 3.33 | $CH_3$ | 6-$OCF_2Br$ | |
| 3.34 | $CH_3$ | 6-$OCF_3$ | |
| 3.35 | $CH_3$ | 6-$OCH_2$(cProp-$Br_2$(2,2)) | resin |
| 3.36 | $CH_3$ | 6-$OCH_2$(cProp-$CH_2$(1)-$Cl_2$(2,2)) | resin |
| 3.37 | $CH_3$ | 6-$OCH_2C(CH_3)=CH_2$ | |
| 3.38 | $CH_3$ | 6-$OCH_2CH_3$ | |
| 3.39 | $CH_3$ | 6-$OCH_2CH_2CH_3$ | |
| 3.40 | $CH_3$ | 6-$OCH_2CH_2CH_2CH_3$ | |
| 3.41 | $CH_3$ | 6-$OCH_2C_6H_5$ | |
| 3.42 | $CH_3$ | 6-$OCH_2C_6H_4F$(2) | |
| 3.43 | $CH_3$ | 6-$OCH_2C_6H_4F$(3) | |
| 3.44 | $CH_3$ | 6-$OCH_2C_6H_4F$(4) | 86–94° |
| 3.45 | $CH_3$ | 6-$OCH_2C_6H_4Cl$(2) | |
| 3.46 | $CH_3$ | 6-$OCH_2C_8H_4Cl$(3) | |
| 3.47 | $CH_3$ | 6-$OCH_2C_6H_4Cl$(4) | |
| 3.48 | $CH_3$ | 6-$OCH_2C_6H_4Br$(4) | |
| 3.49 | $CH_3$ | 6-$OCH_2C_6H_4OCH_3$(4) | |
| 3.50 | $CH_3$ | 6-$OCH_2C_6H_3F_2$(2,6) | |
| 3.51 | $CH_3$ | 6-$OCH_2C_6H_3F_2$(2,4) | |
| 3.52 | $CH_3$ | 6-$OCH_2C_6H_3F_2$(3,4) | |
| 3.53 | $CH_3$ | 6-6$CH_2C_6H_3Cl_2$(2,6) | |
| 3.54 | $CH_3$ | 6-$OCH_2C_6H_3Cl_2$(2,4) | |
| 3.55 | $CH_3$ | 6-$OCH_2C_6H_3Cl_2$(3,4) | |

TABLE 3-continued

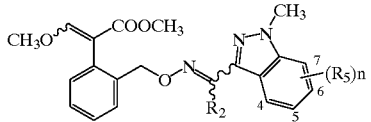

| Compound No. | R₂ | (R₅)n | Phys. data |
|---|---|---|---|
| 3.56 | CH₃ | 6-OC₆H₅ | |
| 3.57 | CH₃ | 6-OC₆H₄Cl(4) | 124–125° |
| 3.58 | CH₃ | 6-OC₆H₄F(4) | |
| 3.59 | CH₃ | 6-OC₆H₄CN(4) | |
| 3.60 | CH₃ | 6-OC₆H₄OCH₃(4) | |
| 3.61 | CH₃ | 6-OC₆H₄CF₃(4) | |
| 3.62 | C₂H₅ | H | |
| 3.63 | C₂H₅ | 6-OCH₂(cProp-Cl₂(2,2)) | |
| 3.64 | C₂H₅ | 6-OCH₂C₆H₄F(4) | |
| 3.65 | n-propyl | H | |
| 3.66 | n-propyl | 6-OCH₂(cProp-Cl₂(2,2)) | |
| 3.67 | n-propyl | 6-OCH₂C₆H₄F(4) | |
| 3.68 | CN | H | |
| 3.69 | CN | 6-OCH₂(cProp-Cl₂(2,2)) | |
| 3.70 | CN | 6-OCH₂C₆H₄F(4) | |
| 3.71 | CN | 6-OCH₂C₆H₄CF₃(3) | |
| 3.72 | CN | 6-OCF₂CHFCF₃ | |
| 3.73 | CN | 6-OCH₂CH=CCl₂ | |
| 3.74 | SCF₃ | H | |
| 3.75 | CF₃ | H | |
| 3.76 | CH₃ | 5-F,6-OCH₃ | |
| 3.77 | CH₃ | 5-F,6-OCH₂(cProp-Cl₂(2,2)) | 138–140° |
| 3.78 | CH₃ | 5-F,6-OCH₂C₆H₄F(4) | 110–115° |
| 3.79 | CH₃ | 5-F,6-OCH₂C₆H₄Cl(4) | |
| 3.80 | CH₃ | 5-F,6-OCH₂C₆H₄CF₃(4) | |
| 3.81 | CH₃ | 5-F,6-OCH₂C₆H₄CF₃(3) | 148–150° |
| 3.82 | CH₃ | 5-F,6-OCH₂C₆H₄CF₃(2) | |
| 3.83 | CH₃ | 5-F,6-OCF₂CHFCF₃ | |
| 3.84 | CH₃ | 5-F,6-OCF₂CHF₂ | |
| 3.85 | CH₃ | 5-F,6-OCHF₂ | |
| 3.86 | CH₃ | 5-F,6-OCF₃ | |
| 3.87 | CH₃ | 5-Cl,6-OCH₃ | |
| 3.88 | CH₃ | 5-Cl,6-OCH₂C₆H₄CF₃(4) | |
| 3.89 | CH₃ | 5-Cl,6-OCH₂C₆H₄CF₃(3) | |
| 3.90 | CH₃ | 5-Cl,6-OCH₂C₆H₄CF₃(2) | |
| 3.91 | CH₃ | 5-Cl,6-OCH₂(cProp-Cl₂(2,2)) | |
| 3.92 | CH₃ | 5-Br,6-OCH₂C₆H₄CF₃(3) | |
| 3.93 | CH₃ | 5-Br,6-OCH₂(cProp-Cl₂(2,2)) | |
| 3.94 | CH₃ | 6-OCH₂-Si(CH₃)₃ | resin |
| 3.95 | cProp | H | |
| 3.96 | cProp | 6-OCH₂(cProp-Cl₂(2,2)) | |
| 3.97 | cProp | 6-OCH₂C₆H₄F(4) | |
| 3.98 | CH₃ | 6-OCH(CH₃)₂ | |
| 3.99 | CH₃ | 6-OC(CH₃)₃ | |
| 3.100 | CH₃ | 6-OCH₂CH(CH₃)₂ | |
| 3.101 | CH₃ | 6-OCH(CH₃)CH₂CH₃ | |
| 3.102 | CH₃ | 6-OC₆H₄CF₃(2) | |
| 3.103 | CH₃ | 6-OC₆H₄CF₃(3) | 76–78° |
| 3.104 | CH₃ | 6-OC₆H₄Br(4) | |
| 3.105 | CH₃ | 6-OC₆H₃F₂(2,4) | |
| 3.106 | CH₃ | 6-OC₆H₃Cl₂(3,4) | 87–90° |
| 3.107 | CH₃ | 6-OC₆H₄—OCF₃(4) | |
| 3.108 | CH₃ | 6-OC₆H₃Cl₂(2,4) | 137–138° |
| 3.109 | CH₃ | 6-OC₆H₄F(2) | |
| 3.110 | CH₃ | 6-OC₆H₄-(4-OC₆H₅) | |
| 3.111 | CH₃ | 6-OC₆F₅ | |
| 3.112 | CH₃ | 6-OCH₂C₆H₄-(4-tert-butyl) | |
| 3.113 | CH₃ | 6-OC₆H₄-(4-tert-butyl) | |

TABLE 4

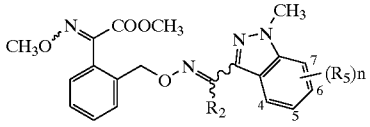

| Compound No. | R₂ | (R₅)n | Phys. data |
|---|---|---|---|
| 4.1 | CH₃ | H | |
| 4.2 | CH₃ | 6-OCH₃ | |
| 4.3 | CH₃ | 6-OCH₂(cProp-Cl₂(2,2)) | |
| 4.4 | CH₃ | 6-OCH₂C₆H₄CF₃(3) | |
| 4.5 | CH₃ | 6-OCH₂CH=CH₂ | |
| 4.6 | CH₃ | 6-OCH₂C≡CH | |
| 4.7 | CH₃ | 6-OCH₂C₆H₄CF₃(4) | |
| 4.8 | CH₃ | 6-OCH₂C₆H₄CF₃(2) | |
| 4.9 | CH₃ | 5-OCH₃ | |
| 4.10 | CH₃ | 6-OCH₂CH=CCl₂ | |
| 4.11 | CH₃ | 6-OCF₂CHFCF₃ | |
| 4.12 | CH₃ | 6-OCF₂CF₂CF₃ | |
| 4.13 | CH₃ | 4-F | |
| 4.14 | CH₃ | 5-F | |
| 4.15 | CH₃ | 6-F | 180° |
| 4.16 | CH₃ | 7-F | |
| 4.17 | CH₃ | 4-Cl | |
| 4.18 | CH₃ | 5-Cl | |
| 4.19 | CH₃ | 6-Cl | |
| 4.20 | CH₃ | 7-Cl | |
| 4.21 | CH₃ | 4-CH₃ | |
| 4.22 | CH₃ | 5-CH₃ | |
| 4.23 | CH₃ | 6-CH₃ | |
| 4.24 | CH₃ | 7-CH₃ | |
| 4.25 | CH₃ | 4-CF₃ | |
| 4.26 | CH₃ | 5-CF₃ | |
| 4.27 | CH₃ | 6-CF₃ | 138° |
| 4.28 | CH₃ | 7-CF₃ | |
| 4.29 | CH₃ | 6-OCF₂CHF₂ | |
| 4.30 | CH₃ | 6-OCF₂CHFCl | |
| 4.31 | CH₃ | 6-OCF₂CHFBr | |
| 4.32 | CH₃ | 6-OCHF₂ | |
| 4.33 | CH₃ | 6-OCF₂Br | |
| 4.34 | CH₃ | 6-OCF₃ | |
| 4.35 | CH₃ | 6-OCH₂(cProp-Br₂(2,2)) | |
| 4.36 | CH₃ | 6-OCH₂(cProp-CH₂(1)-Cl₂(2,2)) | |
| 4.37 | CH₃ | 6-OCH₂C(CH₃)=CH₂ | |
| 4.38 | CH₃ | 6-OCH₂CH₃ | |
| 4.39 | CH₃ | 6-OCH₂CH₂CH₃ | |
| 4.40 | CH₃ | 6-OCH₂CH₂CH₂CH₃ | |
| 4.41 | CH₃ | 6-OC₆H₅ | |
| 4.42 | CH₃ | 6-OCH₂C₆H₄F(2) | |
| 4.43 | CH₃ | 6-OCH₂C₆H₄F(3) | |
| 4.44 | CH₃ | 6-OCH₂C₆H₄F(4) | |
| 4.45 | CH₃ | 6-OCH₂C₆H₄Cl(2) | |
| 4.46 | CH₃ | 6-OCH₂C₆H₄Cl(3) | |
| 4.47 | CH₃ | 6-OCH₂C₆H₄Cl(4) | |
| 4.48 | CH₃ | 6-OCH₂C₆H₄Br(4) | |
| 4.49 | CH₃ | 6-OCH₂C₆H₄OCH₃(4) | |
| 4.50 | CH₃ | 6-OCH₂C₆H₃F₂(2,6) | |
| 4.51 | CH₃ | 6-OCH₂C₆H₃F₂(2,4) | |
| 4.52 | CH₃ | 6-OCH₂C₆H₃F₂(3,4) | |
| 4.53 | CH₃ | 6-OCH₂C₆H₃Cl₂(2,6) | |
| 4.54 | CH₃ | 6-OCH₂C₆H₃Cl₂(2,4) | |
| 4.55 | CH₃ | 6-OCH₂C₆H₃Cl₂(3,4) | |
| 4.56 | CH₃ | 6-OC₆H₅ | |
| 4.57 | CH₃ | 6-OC₆H₄Cl(4) | 95–96° |
| 4.58 | CH₃ | 6-OC₆H₄F(4) | |
| 4.59 | CH₃ | 6-OC₆H₄CN(4) | |
| 4.60 | CH₃ | 6-OC₆H₄OCH₃(4) | |
| 4.61 | CH₃ | 6-OC₆H₄CF₃(4) | |
| 4.62 | C₂H₅ | H | |
| 4.63 | C₂H₅ | 6-OCH₂(cProp-Cl₂(2,2)) | |
| 4.64 | C₂H₅ | 6-OCH₂C₆H₄F(4) | |
| 4.65 | n-propyl | H | |
| 4.66 | n-propyl | 6-OCH₂(cProp-Cl₂(2,2)) | |
| 4.67 | n-propyl | 6-OCH₂C₆H₄F(4) | |
| 4.68 | CN | H | |
| 4.69 | CN | 6-OCH₂(cProp-Cl₂(2,2)) | |

TABLE 4-continued

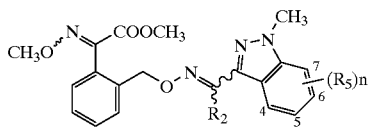

| Compound No. | R₂ | (R₅)n | Phys. data |
|---|---|---|---|
| 4.70 | CN | 6-OCH$_2$C$_6$H$_4$F(4) | |
| 4.71 | CN | 6-OCH$_2$C$_6$H$_4$CF$_3$(3) | |
| 4.72 | CN | 6-OCF$_2$CHFCF$_3$ | |
| 4.73 | CN | 6-OCH$_2$CH=CCl$_2$ | |
| 4.74 | SCF$_3$ | H | |
| 4.75 | CF$_3$ | H | |
| 4.76 | CH$_3$ | 5-F,6-OCH$_3$ | |
| 4.77 | CH$_3$ | 5-F,6-OCH$_2$(cProp-Cl$_2$(2,2)) | |
| 4.78 | CH$_3$ | 5-F,6-OCH$_2$C$_6$H$_4$F(4) | |
| 4.79 | CH$_3$ | 5-F,6-OCH$_2$C$_6$H$_4$Cl(4) | |
| 4.80 | CH$_3$ | 5-F,6-OCH$_2$C$_6$H$_4$CF$_3$(4) | |
| 4.81 | CH$_3$ | 5-F,6-OCH$_2$C$_6$H$_4$CF$_3$(3) | |
| 4.82 | CH$_3$ | 5-F,6-OCH$_2$C$_6$H$_4$CF$_3$(2) | |
| 4.83 | CH$_3$ | 5-F,6-OCF$_2$CHFCF$_3$ | |
| 4.84 | CH$_3$ | 5-F,6-OCF$_2$CHF$_2$ | |
| 4.85 | CH$_3$ | 5-F,6-OCHF$_2$ | |
| 4.86 | CH$_3$ | 5-F,6-OCF$_3$ | |
| 4.87 | CH$_3$ | 5-Cl,6-OCH$_3$ | |
| 4.88 | CH$_3$ | 5-Cl,6-OCH$_2$C$_6$H$_4$CF$_3$(4) | |
| 4.89 | CH$_3$ | 5-Cl,6-OCH$_2$C$_6$H$_4$CF$_3$(3) | |
| 4.90 | CH$_3$ | 5-Cl,6-OCH$_2$C$_6$H$_4$CF$_3$(2) | |
| 4.91 | CH$_3$ | 5-Cl,6-OCH$_2$(cProp-Cl$_2$(2,2)) | |
| 4.92 | CH$_3$ | 5-Br,6-OCH$_2$C$_6$H$_4$CF$_3$(3) | |
| 4.93 | CH$_3$ | 5-Br,6-OCH$_2$(cProp-Cl$_2$(2,2)) | |
| 4.94 | CH$_3$ | 6-OCH$_2$-Si(CH$_3$)$_3$ | |
| 4.95 | cProp | H | |
| 4.96 | cProp | 6-OCH$_2$(cProp-Cl$_2$(2,2)) | |
| 4.97 | cProp | 6-OCH$_2$C$_6$H$_4$F(4) | |
| 4.98 | CH$_3$ | 6-OCH(CH$_3$)$_2$ | |
| 4.99 | CH$_3$ | 6-OC(CH$_3$)$_3$ | |
| 4.100 | CH$_3$ | 6-OCH$_2$CH(CH$_3$)$_2$ | |
| 4.101 | CH$_3$ | 6-OCH(CH$_3$)CH$_2$CH$_3$ | |
| 4.102 | CH$_3$ | 6-OC$_6$H$_4$CF$_3$(2) | |
| 4.103 | CH$_3$ | 6-OC$_6$H$_4$CF$_3$(3) | 126–127° |
| 4.104 | CH$_3$ | 6-OC$_6$H$_4$Br(4) | |
| 4.105 | CH$_3$ | 6-OC$_6$H$_3$F$_2$(2,4) | |
| 4.106 | CH$_3$ | 6-OC$_6$H$_3$Cl$_2$(3,4) | 96–98° |
| 4.107 | CH$_3$ | 6-OC$_6$H$_4$—OCF$_3$(4) | |
| 4.108 | CH$_3$ | 6-OC$_6$H$_3$Cl$_2$(2,4) | 85–87° |
| 4.109 | CH$_3$ | 6-OC$_6$H$_4$F(2) | |
| 4.110 | CH$_3$ | 6-OC$_6$H$_4$-(4-OC$_6$H$_5$) | |
| 4.111 | CH$_3$ | 6-OC$_6$F$_5$ | |
| 4.112 | CH$_3$ | 6-OCH$_2$C$_6$H$_4$-(4-tert-butyl) | |
| 4.113 | CH$_3$ | 6-OC$_6$H$_4$-(4-tert-butyl) | |

TABLE 5

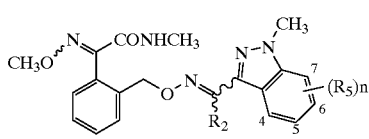

| Compound No. | R₂ | (R₅)n | Phys. data |
|---|---|---|---|
| 5.1 | CH$_3$ | H | |
| 5.2 | CH$_3$ | 6-OCH$_3$ | |
| 5.3 | CH$_3$ | 6-OCH$_2$(cProp-Cl$_2$(2,2)) | |
| 5.4 | CH$_3$ | 6-OCH$_2$C$_6$H$_4$CF$_3$(3) | |
| 5.5 | CH$_3$ | 6-OCH$_2$CH=CH$_2$ | |
| 5.6 | CH$_3$ | 6-OCH$_2$C≡CH | |
| 5.7 | CH$_3$ | 6-OCH$_2$C$_6$H$_4$CF$_3$(4) | |
| 5.8 | CH$_3$ | 6-OCH$_2$C$_6$H$_4$CF$_3$(2) | |
| 5.9 | CH$_3$ | 5-OCH$_3$ | |
| 5.10 | CH$_3$ | 6-OCH$_2$CH=CCl$_2$ | |

TABLE 5-continued

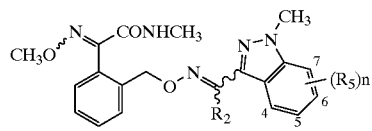

| Compound No. | R₂ | (R₅)n | Phys. data |
|---|---|---|---|
| 5.11 | CH$_3$ | 6-OCF$_2$CHFCF$_3$ | |
| 5.12 | CH$_3$ | 6-OCF$_2$CF$_2$CF$_3$ | |
| 5.13 | CH$_3$ | 4-F | |
| 5.14 | CH$_3$ | 5-F | |
| 5.15 | CH$_3$ | 6-F | |
| 5.16 | CH$_3$ | 7-F | |
| 5.17 | CH$_3$ | 4-Cl | |
| 5.18 | CH$_3$ | 5-Cl | |
| 5.19 | CH$_3$ | 6-Cl | |
| 5.20 | CH$_3$ | 7-Cl | |
| 5.21 | CH$_3$ | 4-CH$_3$ | |
| 5.22 | CH$_3$ | 5-CH$_3$ | |
| 5.23 | CH$_3$ | 6-CH$_3$ | |
| 5.24 | CH$_3$ | 7-CH$_3$ | |
| 5.25 | CH$_3$ | 4-CF$_3$ | |
| 5.26 | CH$_3$ | 5-CF$_3$ | |
| 5.27 | CH$_3$ | 6-CF$_3$ | |
| 5.28 | CH$_3$ | 7-CF$_3$ | |
| 5.29 | CH$_3$ | 6-OCF$_2$CHF$_2$ | |
| 5.30 | CH$_3$ | 6-OCF$_2$CHFCl | |
| 5.31 | CH$_3$ | 6-OCF$_2$CHFBr | |
| 5.32 | CH$_3$ | 6-OCHF$_2$ | |
| 5.33 | CH$_3$ | 6-OCF$_2$Br | |
| 5.34 | CH$_3$ | 6-OCF$_3$ | |
| 5.35 | CH$_3$ | 6-OCH$_2$(cProp-Br$_2$(2,2)) | |
| 5.36 | CH$_3$ | 6-OCH$_2$(cProp-CH$_3$(1)-Cl$_2$(2,2)) | |
| 5.37 | CH$_3$ | 6-OCH$_2$C(CH$_3$)=CH$_2$ | |
| 5.38 | CH$_3$ | 6-OCH$_2$CH$_3$ | |
| 5.39 | CH$_3$ | 6-OCH$_2$CH$_2$CH$_3$ | |
| 5.40 | CH$_3$ | 6-OCH$_2$CH$_2$CH$_2$CH$_3$ | |
| 5.41 | CH$_3$ | 6-OCH$_2$C$_6$H$_5$ | |
| 5.42 | CH$_3$ | 6-OCH$_2$C$_6$H$_4$F(2) | |
| 5.43 | CH$_3$ | 6-OCH$_2$C$_6$H$_4$F(3) | |
| 5.44 | CH$_3$ | 6-OCH$_2$C$_6$H$_4$F(4) | |
| 5.45 | CH$_3$ | 6-OCH$_2$C$_6$H$_4$Cl(2) | |
| 5.46 | CH$_3$ | 6-OCH$_2$C$_6$H$_4$Cl(3) | |
| 5.47 | CH$_3$ | 6-OCH$_2$C$_6$H$_4$Cl(4) | |
| 5.48 | CH$_3$ | 6-OCH$_2$C$_6$H$_4$Br(4) | |
| 5.49 | CH$_3$ | 6-OCH$_2$C$_6$H$_4$OCH$_3$(4) | |
| 5.50 | CH$_3$ | 6-OCH$_2$C$_6$H$_3$F$_2$(2,6) | |
| 5.51 | CH$_3$ | 6-OCH$_2$C$_6$H$_3$F$_2$(2,4) | |
| 5.52 | CH$_3$ | 6-OCH$_2$C$_6$H$_3$F$_2$(3,4) | |
| 5.53 | CH$_3$ | 6-OCH$_2$C$_6$H$_3$Cl$_2$(2,6) | |
| 5.54 | CH$_3$ | 6-OCH$_2$C$_6$H$_3$Cl$_2$(2,4) | |
| 5.55 | CH$_3$ | 6-OCH$_2$C$_6$H$_3$Cl$_2$(3,4) | |
| 5.56 | CH$_3$ | 6-OC$_6$H$_5$ | |
| 5.57 | CH$_3$ | 6-OC$_6$H$_4$Cl(4) | 137–138° |
| 5.58 | CH$_3$ | 6-OC$_6$H$_4$F(4) | |
| 5.59 | CH$_3$ | 6-OC$_6$H$_4$CN(4) | |
| 5.60 | CH$_3$ | 6-OC$_6$H$_4$OCH$_3$(4) | |
| 5.61 | CH$_3$ | 6-OC$_6$H$_4$CF$_3$(4) | |
| 5.62 | C$_2$H$_5$ | H | |
| 5.63 | C$_2$H$_5$ | 6-OCH$_2$(cProp-Cl$_2$(2,2)) | |
| 5.64 | C$_2$H$_5$ | 6-OCH$_2$C$_6$H$_4$F(4) | |
| 5.65 | n-propyl | H | |
| 5.66 | n-propyl | 6-OCH$_2$(cProp-Cl$_2$(2,2)) | |
| 5.67 | n-propyl | 6-OCH$_2$C$_6$H$_4$F(4) | |
| 5.68 | CN | H | |
| 5.69 | CN | 6-OCH$_2$(cProp-Cl$_2$(2,2)) | |
| 5.70 | CN | 6-OCH$_2$C$_6$H$_4$F(4) | |
| 5.71 | CN | 6-OCH$_2$C$_6$H$_4$CF$_3$(3) | |
| 5.72 | CN | 6-OCF$_2$CHFCF$_3$ | |
| 5.73 | CN | 6-OCH$_2$CH=CCl$_2$ | |
| 5.74 | SCF$_3$ | H | |
| 5.75 | CF$_3$ | H | |
| 5.76 | CH$_3$ | 5-F,6-OCH$_3$ | |
| 5.77 | CH$_3$ | 5-F,6-OCH$_2$(cProp-Cl$_2$(2,2)) | |
| 5.78 | CH$_3$ | 5-F,6-OCH$_2$C$_6$H$_4$F(4) | |
| 5.79 | CH$_3$ | 5-F,6-OCH$_2$C$_6$H$_4$Cl(4) | |

TABLE 5-continued

Structure: CH₃O-N=C(CONHCH₃)-C₆H₄-CH₂-O-N=C(R₂)-[1-methyl-indazol-3-yl]-(R₅)n

| Compound No. | R₂ | (R₅)n | Phys. data |
|---|---|---|---|
| 5.80 | CH₃ | 5-F,6-OCH₂C₆H₄CF₃(4) | |
| 5.81 | CH₃ | 5-F,6-OCH₂C₆H₄CF₃(3) | |
| 5.82 | CH₃ | 5-F,6-OCH₂C₆H₄CF₃(2) | |
| 5.83 | CH₃ | 5-F,6-OCF₂CHFCF₃ | |
| 5.84 | CH₃ | 5-F,6-OCF₂CHF₂ | |
| 5.85 | CH₃ | 5-F,6-OCHF₂ | |
| 5.86 | CH₃ | 5-F,6-OCF₃ | |
| 5.87 | CH₃ | 5-Cl,6-OCH₃ | |
| 5.88 | CH₃ | 5-Cl,6-OCH₂C₆H₄CF₃(4) | |
| 5.89 | CH₃ | 5-Cl, 6-OCH₂C₆H₄CF₃(3) | |
| 5.90 | CH₃ | 5-Cl,6-OCH₂C₆H₄CF₃(2) | |
| 5.91 | CH₃ | 5-Cl,6-OCH₂(cProp-Cl₂(2,2)) | |
| 5.92 | CH₃ | 5-Br,6-OCH₂C₆H₄CF₃(3) | |
| 5.93 | CH₃ | 5-Br,6-OCH₂(cProp-Cl₂(2,2)) | |
| 5.94 | CH₃ | 6-OCH₂-Si(CH₃)₃ | |
| 5.95 | cProp | H | |
| 5.96 | cProp | 6-OCH₂(cProp-Cl₂(2,2)) | |
| 5.97 | cProp | 6-OCH₂C₆H₄F(4) | |
| 5.98 | CH₃ | 6-OCH(CH₃)₂ | |
| 5.99 | CH₃ | 6-OC(CH₃)₃ | |
| 5.100 | CH₃ | 6-OCH₂CH(CH₃)₂ | |
| 5.101 | CH₃ | 6-OCH(CH₃)CH₂CH₃ | |
| 5.102 | CH₃ | 6-OC₆H₄CF₃(2) | |
| 5.103 | CH₃ | 6-OC₆H₄CF₃(3) | 119–120° |
| 5.104 | CH₃ | 6-OC₆H₄Br(4) | |
| 5.105 | CH₃ | 6-OC₆H₃F₂(2,4) | |
| 5.106 | CH₃ | 6-OC₆H₃Cl₂(3,4) | 112–114° |
| 5.107 | CH₃ | 6-OC₆H₄—OCF₃(4) | |
| 5.108 | CH₃ | 6-OC₆H₃Cl₂(2,4) | 110–112° |
| 5.109 | CH₃ | 6-OC₆H₄F(2) | |
| 5.110 | CH₃ | 6-OC₆H₄-(4-OC₆H₅) | |
| 5.111 | CH₃ | 6-OC₆F₅ | |
| 5.112 | CH₃ | 6-OCH₂C₆H₄-(4-tert-butyl) | |
| 5.113 | CH₃ | 6-OC₆H₄-(4-tert-butyl) | |

TABLE 6

Structure: CH₃O-N=C(CSNHCH₃)-C₆H₄-CH₂-O-N=C(R₂)-[1-methyl-indazol-3-yl]-(R₅)n

| Compound No. | R₂ | (R₅)n | Phys. data |
|---|---|---|---|
| 6.1 | CH₃ | H | |
| 6.2 | CH₃ | 6-OCH₃ | |
| 6.3 | CH₃ | 6-OCH₂(cProp-Cl₂(2,2)) | |
| 6.4 | CH₃ | 6-OCH₂C₆H₄CF₃(3) | |
| 6.5 | CH₃ | 6-OCH₂CH=CH₂ | |
| 6.6 | CH₃ | 6-OCH₂C≡CH | |
| 6.7 | CH₃ | 6-OCH₂C₆H₄CF₃(4) | |
| 6.8 | CH₃ | 6-OCH₂C₆H₄CF₃(2) | |
| 6.9 | CH₃ | 5-OCH₃ | |
| 6.10 | CH₃ | 6-OCH₂CH=CCl₂ | |
| 6.11 | CH₃ | 6-OCF₂CHFCF₃ | |
| 6.12 | CH₃ | 6-OCF₂CF₂CF₃ | |
| 6.13 | CH₃ | 4-F | |
| 6.14 | CH₃ | 5-F | |
| 6.15 | CH₃ | 6-F | |
| 6.16 | CH₃ | 7-F | |
| 6.17 | CH₃ | 4-Cl | |
| 6.18 | CH₃ | 5-Cl | |
| 6.19 | CH₃ | 6-Cl | |
| 6.20 | CH₃ | 7-Cl | |
| 6.21 | CH₃ | 4-CH₃ | |
| 6.22 | CH₃ | 5-CH₃ | |
| 6.23 | CH₃ | 6-CH₃ | |
| 6.24 | CH₃ | 7-CH₃ | |
| 6.25 | CH₃ | 4-CF₃ | |
| 6.26 | CH₃ | 5-CF₃ | |
| 6.27 | CH₃ | 6-CF₃ | |
| 6.28 | CH₃ | 7-CF₃ | |
| 6.29 | CH₃ | 6-OCF₂CHF₂ | |
| 6.30 | CH₃ | 6-OCF₂CHFCl | |
| 6.31 | CH₃ | 6-OCF₂CHFBr | |
| 6.32 | CH₃ | 6-OCHF₂ | |
| 6.33 | CH₃ | 6-OCF₂Br | |
| 6.34 | CH₃ | 6-OCF₃ | |
| 6.35 | CH₃ | 6-OCH₂(cProp-Br₂(2,2)) | |
| 6.36 | CH₃ | 6-OCH₂(cProp-CH₃(1)-Cl₂(2,2)) | |
| 6.37 | CH₃ | 6-OCH₂C(CH₃)=CH₂ | |
| 6.38 | CH₃ | 6-OCH₂CH₃ | |
| 6.39 | CH₃ | 6-OCH₂CH₂CH₃ | |
| 6.40 | CH₃ | 6-OCH₂CH₂CH₂CH₃ | |
| 6.41 | CH₃ | 6-OCH₂C₆H₅ | |
| 6.42 | CH₃ | 6-OCH₂C₆H₄F(2) | |
| 6.43 | CH₃ | 6-OCH₂C₆H₄F(3) | |
| 6.44 | CH₃ | 6-OCH₂C₆H₄F(4) | |
| 6.45 | CH₃ | 6-OCH₂C₆H₄Cl(2) | |
| 6.46 | CH₃ | 6-OCH₂C₆H₄Cl(3) | |
| 6.47 | CH₃ | 6-OCH₂C₆H₄Cl(4) | |
| 6.48 | CH₃ | 6-OCH₂C₆H₄Br(4) | |
| 6.49 | CH₃ | 6-OCH₂C₆H₄OCH₃(4) | |
| 6.50 | CH₃ | 6-OCH₂C₆H₃F₂(2,6) | |
| 6.51 | CH₃ | 6-OCH₂C₆H₃F₂(2,4) | |
| 6.52 | CH₃ | 6-OCH₂C₆H₃F₂(3,4) | |
| 6.53 | CH₃ | 6-OCH₂C₆H₃Cl₂(2,6) | |
| 6.54 | CH₃ | 6-OCH₂C₆H₃Cl₂(2,4) | |
| 6.55 | CH₃ | 6-OCH₂C₆H₃Cl₂(3,4) | |
| 6.56 | CH₃ | 6-OC₆H₅ | |
| 6.57 | CH₃ | 6-OC₆H₄Cl(4) | |
| 6.58 | CH₃ | 6-OC₆H₄F(4) | |
| 6.59 | CH₃ | 6-OC₆H₄CN(4) | |
| 6.60 | CH₃ | 6-OC₆H₄OCH₃(4) | |
| 6.61 | CH₃ | 6-OC₆H₄CF₃(4) | |
| 6.62 | C₂H₅ | H | |
| 6.63 | C₂H₅ | 6-OCH₂(cProp-Cl₂(2,2)) | |
| 6.64 | C₂H₅ | 6-OCH₂C₆H₄F(4) | |
| 6.65 | n-propyl | H | |
| 6.66 | n-propyl | 6-OCH₂(cProp-Cl₂(2,2)) | |
| 6.67 | n-propyl | 6-OCH₂C₆H₄F(4) | |
| 6.68 | CN | H | |
| 6.69 | CN | 6-OCH₂(cProp-Cl₂(2,2)) | |
| 6.70 | CN | 6-OCH₂C₆H₄F(4) | |
| 6.71 | CN | 6-OCH₂C₆H₄CF₃(3) | |
| 6.72 | CN | 6-OCF₂CHFCF₃ | |
| 6.73 | CN | 6-OCH₂CH=CCl₂ | |
| 6.74 | SCF₃ | H | |
| 6.75 | F₃ | H | |
| 6.76 | CH₃ | 5-F,6-OCH₃ | |
| 6.77 | CH₃ | 5-F,6-OCH₂(cProp-Cl₂(2,2)) | |
| 6.78 | CH₃ | 5-F,6-OCH₂C₆H₄F(4) | |
| 6.79 | CH₃ | 5-F,6-OCH₂C₆H₄Cl(4) | |
| 6.80 | CH₃ | 5-F,6-OCH₂C₆H₄CF₃(4) | |
| 6.81 | CH₃ | 5-F,6-OCH₂C₆H₄CF₃(3) | |
| 6.82 | CH₃ | 5-F,6-OCH₂C₆H₄CF₃(2) | |
| 6.83 | CH₃ | 5-F,6-OCF₂CHFCF₃ | |
| 6.84 | CH₃ | 5-F,6-OCF₂CHF₂ | |
| 6.85 | CH₃ | 5-F,6-OCHF₂ | |
| 6.86 | CH₃ | 5-F,6-OCF₃ | |
| 6.87 | CH₃ | 5-Cl,6-OCH₃ | |
| 6.88 | CH₃ | 5-Cl,6-OCH₂C₆H₄CF₃(4) | |
| 6.89 | CH₃ | 5-Cl,6-OCH₂C₆H₄CF₃(3) | |
| 6.90 | CH₃ | 5-Cl,6-OCH₂C₆H₄CF₃(2) | |

TABLE 6-continued

[Structure: CH₃O-N=C(CSNHCH₃)-C₆H₄-CH₂-O-N=C(R₂)-indazole(N-CH₃)(R₅)n]

| Compound No. | R₂ | (R₅)n | Phys. data |
|---|---|---|---|
| 6.91 | CH₃ | 5-Cl,6-OCH₂(cProp-Cl₂(2,2)) | |
| 6.92 | CH₃ | 5-Br,6-OCH₂C₆H₄CF₃(3) | |
| 6.93 | CH₃ | 5-Br,6-OCH₂(cProp-Cl₂(2,2)) | |
| 6.94 | CH₃ | 6-OCH₂-Si(CH₃)₃ | |
| 6.95 | cProp | H | |
| 6.96 | cProp | 6-OCH₂(cProp-Cl₂(2,2)) | |
| 6.97 | cProp | 6-OCH₂C₆H₄F(4) | |
| 6.98 | CH₃ | 6-OCH(CH₃)₂ | |
| 6.99 | CH₃ | 6-OC(CH₃)₃ | |
| 6.100 | CH₃ | 6-OCH₂CH(CH₃)₂ | |
| 6.101 | CH₃ | 6-OCH(CH₃)CH₂CH₃ | |
| 6.102 | CH₃ | 6-OC₆H₄CF₃(2) | |
| 6.103 | CH₃ | 6-OC₆H₄CF₃(3) | |
| 6.104 | CH₃ | 6-OC₆H₄Br(4) | |
| 6.105 | CH₃ | 6-OC₆H₃F₂(2,4) | |

TABLE 7

[Structure: CH₃O-N=C(C(S=O)NHCH₃)-C₆H₄-CH₂-O-N=C(R₂)-indazole(N-CH₃)(R₅)n]

| Compound No. | R₂ | (R₅)n | Phys. data |
|---|---|---|---|
| 7.1 | CH₃ | H | |
| 7.2 | CH₃ | 6-OCH₃ | |
| 7.3 | CH₃ | 6-OCH₂(cProp-Cl₂(2,2)) | |
| 7.4 | CH₃ | 6-OCH₂C₆H₄CF₃(3) | |
| 7.5 | CH₃ | 6-OCH₂CH=CH₂ | |
| 7.6 | CH₃ | 6-OCH₂C≡CH | |
| 7.7 | CH₃ | 6-OCH₂C₆H₄CF₃(4) | |
| 7.8 | CH₃ | 6-OCH₂C₆H₄CF₃(2) | |
| 7.9 | CH₃ | 5-OCH₃ | |
| 7.10 | CH₃ | 6-OCH₂CH=CCl₂ | |
| 7.11 | CH₃ | 6-OCF₂CHFCF₃ | |
| 7.12 | CH₃ | 6-OCF₂CF₂CF₃ | |
| 7.13 | CH₃ | 4-F | |
| 7.14 | CH₃ | 5-F | |
| 7.15 | CH₃ | 6-F | |
| 7.16 | CH₃ | 7-F | |
| 7.17 | CH₃ | 4-Cl | |
| 7.18 | CH₃ | 5-Cl | |
| 7.19 | CH₃ | 6-Cl | |
| 7.20 | CH₃ | 7-Cl | |
| 7.21 | CH₃ | 4-CH₃ | |
| 7.22 | CH₃ | 5-CH₃ | |
| 7.23 | CH₃ | 6-CH₃ | |
| 7.24 | CH₃ | 7-CH₃ | |
| 7.25 | CH₃ | 4-CF₃ | |
| 7.26 | CH₃ | 5-CF₃ | |
| 7.27 | CH₃ | 6-CF₃ | |
| 7.28 | CH₃ | 7-CF₃ | |
| 7.29 | CH₃ | 6-OCF₂CHF₂ | |
| 7.30 | CH₃ | 6-OCF₂CHFCl | |
| 7.31 | CH₃ | 6-OCF₂CHFBr | |
| 7.32 | CH₃ | 6-OCHF₂ | |
| 7.33 | CH₃ | 6-OCF₂Br | |
| 7.34 | CH₃ | 6-OCF₃ | |
| 7.35 | CH₃ | 6-OCH₂(cProp-Br₂(2,2)) | |
| 7.36 | CH₃ | 6-OCH₂(cProp-CH₂(1)-Cl₂(2,2)) | |
| 7.37 | CH₃ | 6-OCH₂C(CH₃)=CH₂ | |
| 7.38 | CH₃ | 6-OCH₂CH₃ | |
| 7.39 | CH₃ | 6-OCH₂CH₂CH₃ | |
| 7.40 | CH₃ | 6-OCH₂CH₂CH₂CH₃ | |
| 7.41 | CH₃ | 6-OCH₂C₆H₅ | |
| 7.42 | CH₃ | 6-OCH₂C₆H₄F(2) | |
| 7.43 | CH₃ | 6-OCH₂C₆H₄F(3) | |
| 7.44 | CH₃ | 6-OCH₂C₆H₄F(4) | |
| 7.45 | CH₃ | 6-OCH₂C₆H₄Cl(2) | |
| 7.46 | CH₃ | 6-OCH₂C₆H₄Cl(3) | |
| 7.47 | CH₃ | 6-OCH₂C₆H₄Cl(4) | |
| 7.48 | CH₃ | 6-OCH₂C₆H₄Br(4) | |
| 7.49 | CH₃ | 6-OCH₂C₆H₄OCH₃(4) | |
| 7.50 | CH₃ | 6-OCH₂C₆H₃F₂(2,6) | |
| 7.51 | CH₃ | 6-OCH₂C₆H₃F₂(2,4) | |
| 7.52 | CH₃ | 6-OCH₂C₆H₃F₂(3,4) | |
| 7.53 | CH₃ | 6-OCH₂C₆H₃Cl₂(2,6) | |
| 7.54 | CH₃ | 6-OCH₂C₆H₃Cl₂(2,4) | |
| 7.55 | CH₃ | 6-OCH₂C₆H₃Cl₂(3,4) | |
| 7.56 | CH₃ | 6-OC₆H₅ | |
| 7.57 | CH₃ | 6-OC₆H₄Cl(4) | |
| 7.58 | CH₃ | 6-OC₆H₄F(4) | |
| 7.59 | CH₃ | 6-OC₆H₄CN(4) | |
| 7.60 | CH₃ | 6-OC₆H₄OCH₃(4) | |
| 7.61 | CH₃ | 6-OC₆H₄CF₃(4) | |
| 7.62 | C₂H₅ | H | |
| 7.63 | C₂H₅ | 6-OCH₂(cProp-Cl₂(2,2)) | |
| 7.64 | C₂H₅ | 6-OCH₂C₆H₄F(4) | |
| 7.65 | n-propyl | H | |
| 7.66 | n-propyl | 6-OCH₂(cProp-Cl₂(2,2)) | |
| 7.67 | n-propyl | 6-OCH₂C₆H₄F(4) | |
| 7.68 | CN | H | |
| 7.69 | CN | 6-OCH₂(cProp-Cl₂(2,2)) | |
| 7.70 | CN | 6-OCH₂C₆H₄F(4) | |
| 7.71 | CN | 6-OCH₂C₆H₄CF₃(3) | |
| 7.72 | CN | 6-OCF₂CHFCF₃ | |
| 7.73 | CN | 6-OCH₂CH=CCl₂ | |
| 7.74 | SCF₃ | H | |
| 7.75 | CF₃ | H | |
| 7.76 | CH₃ | 5-F,6-OCH₃ | |
| 7.77 | CH₃ | 5-F,6-OCH₂(cProp-Cl₂(2,2)) | |
| 7.78 | CH₃ | 5-F,6-OCH₂C₆H₄F(4) | |
| 7.79 | CH₃ | 5-F,6-OCH₂C₆H₄Cl(4) | |
| 7.80 | CH₃ | 5-F,6-OCH₂C₆H₄CF₃(4) | |
| 7.81 | CH₃ | 5-F,6-OCH₂C₆H₄CF₃(3) | |
| 7.82 | CH₃ | 5-F,6-OCH₂C₆H₄CF₃(2) | |
| 7.83 | CH₃ | 5-F,6-OCF₂CHFCF₃ | |
| 7.84 | CH₃ | 5-F,6-OCF₂CHF₂ | |
| 7.85 | CH₃ | 5-F,6-OCHF₂ | |
| 7.86 | CH₃ | 5-F,6-OCF₃ | |
| 7.87 | CH₃ | 5-Cl,6-OCH₃ | |
| 7.88 | CH₃ | 5-Cl,6-OCH₂C₆H₄CF₃(4) | |
| 7.89 | CH₃ | 5-Cl,6-OCH₂C₆H₄CF₃(3) | |
| 7.90 | CH₃ | 5-Cl,6-OCH₂C₆H₄CF₃(2) | |
| 7.91 | CH₃ | 5-Cl,6-OCH₂(cProp-Cl₂(2,2)) | |
| 7.92 | CH₃ | 5-Br,6-OCH₂C₆H₄CF₃(3) | |
| 7.93 | CH₃ | 5-Br,6-OCH₂(cProp-Cl₂(2,2)) | |
| 7.94 | CH₃ | 6-OCH₂-Si(CH₃)₃ | |
| 7.95 | cProp | H | |
| 7.96 | cProp | 6-OCH₂(cProp-Cl₂(2,2)) | |
| 7.97 | cProp | 6-OCH₂C₆H₄F(4) | |
| 7.98 | CH₃ | 6-OCH(CH₃)₂ | |
| 7.99 | CH₃ | 6-OC(CH₃)₃ | |
| 7.100 | CH₃ | 6-OCH₂CH(CH₃)₂ | |
| 7.101 | CH₃ | 6-OCH(CH₃)CH₂CH₃ | |
| 7.102 | CH₃ | 6-OC₆H₄CF₃(2) | |
| 7.103 | CH₃ | 6-OC₆H₄CF₃(3) | |
| 7.104 | CH₃ | 6-OC₆H₄Br(4) | |
| 7.105 | CH₃ | 6-OC₆H₃F₂(2,4) | |

TABLE 8

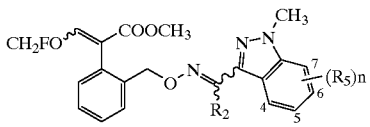

| Compound No. | R₂ | (R₅)n | Phys. data |
|---|---|---|---|
| 8.1 | CH₃ | H | |
| 8.2 | CH₃ | 6-OCH₃ | |
| 8.3 | CH₃ | 6-OCH₂(cProp-Cl₂(2,2)) | |
| 8.4 | CH₃ | 6-OCH₂C₆H₄CF₃(3) | |
| 8.5 | CH₃ | 6-OCH₂CH=CH₂ | |
| 8.6 | CH₃ | 6-OCH₂C≡CH | |
| 8.7 | CH₃ | 6-OCH₂C₆H₄CF₃(4) | |
| 8.8 | CH₃ | 6-OCH₂C₆H₄CF₃(2) | |
| 8.9 | CH₃ | 5-OCH₃ | |
| 8.10 | CH₃ | 6-OCH₂CH=CCl₂ | |
| 8.11 | CH₃ | 6-OCF₂CHFCF₃ | |
| 8.12 | CH₃ | 6-OCF₂CF₂CF₃ | |
| 8.13 | CH₃ | 4-F | |
| 8.14 | CH₃ | 5-F | |
| 8.15 | CH₃ | 6-F | |
| 8.16 | CH₃ | 7-F | |
| 8.17 | CH₃ | 4-Cl | |
| 8.18 | CH₃ | 5-Cl | |
| 8.19 | CH₃ | 6-Cl | |
| 8.20 | CH₃ | 7-Cl | |
| 8.21 | CH₃ | 4-CH₃ | |
| 8.22 | CH₃ | 5-CH₃ | |
| 8.23 | CH₃ | 6-CH₃ | |
| 8.24 | CH₃ | 7-CH₃ | |
| 8.25 | CH₃ | 4-CF₃ | |
| 8.26 | CH₃ | 5-CF₃ | |
| 8.27 | CH₃ | 6-CF₃ | |
| 3.28 | CH₃ | 7-CF₃ | |
| 8.29 | CH₃ | 6-OCF₂CHF₂ | |
| 8.30 | CH₃ | 6-OCF₂CHFCl | |
| 8.31 | CH₃ | 6-OCF₂CHFBr | |
| 8.32 | CH₃ | 6-OCHF₂ | |
| 8.33 | CH₃ | 6-OCF₂Br | |
| 8.34 | CH₃ | 6-OCF₃ | |
| 8.35 | CH₃ | 6-OCH₂(cProp-Br₂(2,2)) | |
| 8.36 | CH₃ | 6-OCH₂(cProp-CH₃(1)-Cl₂(2,2)) | |
| 8.37 | CH₃ | 6-OCH₂C(CH₃)=CH₂ | |
| 8.38 | CH₃ | 6-OCH₂CH₃ | |
| 8.39 | CH₃ | 6-OCH₂CH₂CH₃ | |
| 8.40 | CH₃ | 6-OCH₂CH₂CH₂CH₃ | |
| 8.41 | CH₃ | 6-OCH₂C₆H₅ | |
| 8.42 | CH₃ | 6-OCH₂C₆H₄F(2) | |
| 8.43 | CH₃ | 6-OCH₂C₆H₄F(3) | |
| 8.44 | CH₃ | 6-OCH₂C₆H₄F(4) | |
| 8.45 | CH₃ | 6-OCH₂C₆H₄Cl(2) | |
| 8.46 | CH₃ | 6-OCH₂C₆H₄Cl(3) | |
| 8.47 | CH₃ | 6-OCH₂C₆H₄Cl(4) | |
| 8.48 | CH₃ | 6-OCH₂C₆H₄Br(4) | |
| 8.49 | CH₃ | 6-OCH₂C₆H₄OCH₃(4) | |
| 8.50 | CH₃ | 6-OCH₂C₆H₃F₂(2,6) | |
| 8.51 | CH₃ | 6-OCH₂C₆H₃F₂(2,4) | |
| 8.52 | CH₃ | 6-OCH₂C₆H₃F₂(3,4) | |
| 8.53 | CH₃ | 6-OCH₂C₆H₃Cl₂(2,6) | |
| 8.54 | CH₃ | 6-OCH₂C₆H₃Cl₂(2,4) | |
| 8.55 | CH₃ | 6-OCH₂C₆H₃Cl₂(3,4) | |
| 8.56 | CH₃ | 6-OC₆H₅ | |
| 8.57 | CH₃ | 6-OC₆H₄Cl(4) | |
| 8.58 | CH₃ | 6-OC₆H₄F(4) | |
| 8.59 | CH₃ | 6-OC₆H₄CN(4) | |
| 8.60 | CH₃ | 6-OC₆H₄OCH₃(4) | |
| 8.61 | CH₃ | 6-OC₆H₄CF₃(4) | |
| 8.62 | C₂H₅ | H | |
| 8.63 | C₂H₅ | 6-OCH₂(cProp-Cl₂(2,2)) | |
| 8.64 | C₂H₅ | 6-OCH₂C₆H₄F(4) | |
| 8.65 | n-propyl | H | |
| 8.66 | n-propyl | 6-OCH₂(cProp-Cl₂(2,2)) | |
| 8.67 | n-propyl | 6-OCH₂C₆H₄F(4) | |
| 8.68 | CN | H | |
| 8.69 | CN | 6-OCH₂(cProp-Cl₂(2,2)) | |

TABLE 8-continued

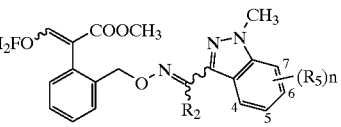

| Compound No. | R₂ | (R₅)n | Phys. data |
|---|---|---|---|
| 8.70 | CN | 6-OCH₂C₆H₄F(4) | |
| 8.71 | CN | 6-OCH₂C₆H₄CF₃(3) | |
| 8.72 | CN | 6-OCF₂CHFCF₃ | |
| 8.73 | CN | 6-OCH₂CH=CCl₂ | |
| 8.74 | SCF₃ | H | |
| 8.75 | CF₃ | H | |
| 8.76 | CH₃ | 5-F,6-OCH₃ | |
| 8.77 | CH₃ | 5-F,6-OCH₂(cProp-Cl₂(2,2)) | |
| 8.78 | CH₃ | 5-F,6-OCH₂C₆H₄F(4) | |
| 8.79 | CH₃ | 5-F,6-OCH₂C₆H₄Cl(4) | |
| 8.80 | CH₃ | 5-F,6-OCH₂C₆H₄CF₃(4) | |
| 8.81 | CH₃ | 5-F,6-OCH₂C₆H₄CF₃(3) | |
| 8.82 | CH₃ | 5-F,6-OCH₂C₆H₄CF₃(2) | |
| 8.83 | CH₃ | 5-F,6-OCF₂CHFCF₃ | |
| 8.84 | CH₃ | 5-F,6-OCF₂CHF₂ | |
| 8.85 | CH₃ | 5-F,6-OCHF₂ | |
| 8.86 | CH₃ | 5-F,6-OCF₃ | |
| 8.87 | CH₃ | 5-Cl,6-OCH₃ | |
| 8.88 | CH₃ | 5-Cl,6-OCH₂C₆H₄CF₃(4) | |
| 8.89 | CH₃ | 5-Cl,6-OCH₂C₆H₄CF₃(3) | |
| 8.90 | CH₃ | 5-Cl,6-OCH₂C₆H₄CF₃(2) | |
| 8.91 | CH₃ | 5-Cl,6-OCH₂(cProp-Cl₂(2,2)) | |
| 8.92 | CH₃ | 5-Br, 6-OCH₂C₆H₄CF₃(3) | |
| 8.93 | CH₃ | 5-Br, 6-OCH₂(cProp-Cl₂(2,2)) | |
| 8.94 | CH₃ | 6-OCH₂-Si(CH₃)₃ | |
| 8.95 | cProp | H | |
| 8.96 | cProp | 6-OCH₂(cProp-Cl₂(2,2)) | |
| 8.97 | cProp | 6-OCH₂C₆H₄F(4) | |
| 8.98 | CH₃ | 6-OCH(CH₃)₂ | |
| 8.99 | CH₃ | 6-OC(CH₃)₃ | |
| 8.100 | CH₃ | 6-OCH₂CH(CH₃)₂ | |
| 8.101 | CH₃ | 6-OCH(CH₃)CH₂CH₃ | |
| 8.102 | CH₃ | 6-OC₆H₄CF₃(2) | |
| 8.103 | CH₃ | 6-OC₆H₄CF₃(3) | |
| 8.104 | CH₃ | 6-OC₆H₄Br(4) | |
| 8.105 | CH₃ | 6-OC₆H₃F₂(2,4) | |

TABLE 9

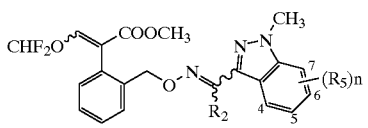

| Compound No. | R₂ | (R₅)n | Phys. data |
|---|---|---|---|
| 9.1 | CH₃ | H | |
| 9.2 | CH₃ | 6-OCH₃ | |
| 9.3 | CH₃ | 6-OCH₂(cProp-Cl₂(2,2)) | |
| 9.4 | CH₃ | 6-OCH₂C₆H₄CF₃(3) | |
| 9.5 | CH₃ | 6-OCH₂CH=CH₂ | |
| 9.6 | CH₃ | 6-OCH₂C≡CH | |
| 9.7 | CH₃ | 6-OCH₂C₆H₄CF₃(4) | |
| 9.8 | CH₃ | 6-OCH₂C₆H₄CF₃(2) | |
| 9.9 | CH₃ | 5-OCH₃ | |
| 9.10 | CH₃ | 6-OCH₂CH=CCl₂ | |
| 9.11 | CH₃ | 6-OCF₂CHFCF₃ | |
| 9.12 | CH₃ | 6-OCF₂CF₂CF₃ | |
| 9.13 | CH₃ | 4-F | |
| 9.14 | CH₃ | 5-F | |
| 9.15 | CH₃ | 6-F | |
| 9.16 | CH₃ | 7-F | |
| 9.17 | CH₃ | 4-Cl | |
| 9.18 | CH₃ | 5-Cl | |
| 9.19 | CH₃ | 6-Cl | |

TABLE 9-continued

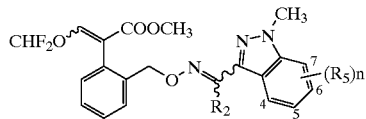

| Compound No. | $R_2$ | $(R_5)n$ | Phys. data |
|---|---|---|---|
| 9.20 | $CH_3$ | 7-Cl | |
| 9.21 | $CH_3$ | 4-$CH_3$ | |
| 9.22 | $CH_3$ | 5-$CH_3$ | |
| 9.23 | $CH_3$ | 6-$CH_3$ | |
| 9.24 | $CH_3$ | 7-$CH_3$ | |
| 9.25 | $CH_3$ | 4-$CF_3$ | |
| 9.26 | $CH_3$ | 5-$CF_3$ | |
| 9.27 | $CH_3$ | 6-$CF_3$ | |
| 9.28 | $CH_3$ | 7-$CF_3$ | |
| 9.29 | $CH_3$ | 6-$OCF_2CHF_2$ | |
| 9.30 | $CH_3$ | 6-$OCF_2CHFCl$ | |
| 9.31 | $CH_3$ | 6-$OCF_2CHFBr$ | |
| 9.32 | $CH_3$ | 6-$OCHF_2$ | |
| 9.33 | $CH_3$ | 6-$OCF_2Br$ | |
| 9.34 | $CH_3$ | 6-$OCF_3$ | |
| 9.35 | $CH_3$ | 6-$OCH_2(cProp-Br_2(2,2))$ | |
| 9.36 | $CH_3$ | 6-$OCH_2(cProp-CH_2(1)-Cl_2(2,2))$ | |
| 9.37 | $CH_3$ | 6-$OCH_2C(CH_3)=CH_2$ | |
| 9.38 | $CH_3$ | 6-$OCH_2CH_3$ | |
| 9.39 | $CH_3$ | 6-$OCH_2CH_2CH_3$ | |
| 9.40 | $CH_3$ | 6-$OCH_2CH_2CH_2CH_3$ | |
| 9.41 | $CH_3$ | 6-$OCH_2C_6H_5$ | |
| 9.42 | $CH_3$ | 6-$OCH_2C_6H_4F(2)$ | |
| 9.43 | $CH_3$ | 6-$OCH_2C_6H_4F(3)$ | |
| 9.44 | $CH_3$ | 6-$OCH_2C_6H_4F(4)$ | |
| 9.45 | $CH_3$ | 6-$OCH_2C_6H_4Cl(2)$ | |
| 9.46 | $CH_3$ | 6-$OCH_2C_6H_4Cl(3)$ | |
| 9.47 | $CH_3$ | 6-$OCH_2C_6H_4Cl(4)$ | |
| 9.48 | $CH_3$ | 6-$OCH_2C_6H_4Br(4)$ | |
| 9.49 | $CH_3$ | 6-$OCH_2C_6H_4OCH_2(4)$ | |
| 9.50 | $CH_3$ | 6-$OCH_2C_6H_3F_2(2,6)$ | |
| 9.51 | $CH_3$ | 6-$OCH_2C_6H_3F_2(2,4)$ | |
| 9.52 | $CH_3$ | 6-$OCH_2C_6H_3F_2(3,4)$ | |
| 9.53 | $CH_3$ | 6-$OCH_2C_6H_3Cl_2(2,6)$ | |
| 9.54 | $CH_3$ | 6-$OCH_2C_6H_3Cl_2(2,4)$ | |
| 9.55 | $CH_3$ | 6-$OCH_2C_6H_3Cl_2(3,4)$ | |
| 9.56 | $CH_3$ | 6-$OC_6H_5$ | |
| 9.57 | $CH_3$ | 6-$OC_6H_4Cl(4)$ | |
| 9.58 | $CH_3$ | 6-$OC_6H_4F(4)$ | |
| 9.59 | $CH_3$ | 6-$OC_6H_4CN(4)$ | |
| 9.60 | $CH_3$ | 6-$OC_6H_4OCH_3(4)$ | |
| 9.61 | $CH_3$ | 6-$OC_6H_4CF_3(4)$ | |
| 9.62 | $C_2H_5$ | H | |
| 9.63 | $C_2H_5$ | 6-$OCH_2(cProp-Cl_2(2,2))$ | |
| 9.64 | $C_2H_5$ | 6-$OCH_2C_6H_4F(4)$ | |
| 9.65 | n-propyl | H | |
| 9.66 | n-propyl | 6-$OCH_2(cProp-Cl_2(2,2))$ | |
| 9.67 | n-propyl | 6-$OCH_2C_6H_4F(4)$ | |
| 9.68 | CN | H | |
| 9.69 | CN | 6-$OCH_2(cProp-Cl_2(2,2)$ | |
| 9.70 | CN | 6-$OCH_2C_6H_4F(4)$ | |
| 9.71 | CN | 6-$OCH_2C_6H_4CF_3(3)$ | |
| 9.72 | CN | 6-$OCF_2CHFCF_3$ | |
| 9.73 | CN | 6-$OCH_2CH=CCl_2$ | |
| 9.74 | $SCF_3$ | H | |
| 9.75 | $CF_3$ | H | |
| 9.76 | $CH_3$ | 5-F,6-$OCH_3$ | |
| 9.77 | $CH_3$ | 5-F,6-$OCH_2(cProp-Cl_2(2,2))$ | |
| 9.78 | $CH_3$ | 5-F,6-$OCH_2C_6H_4F(4)$ | |
| 9.79 | $CH_3$ | 5-F,6-$OCH_2C_6H_4Cl(4)$ | |
| 9.80 | $CH_3$ | 5-F,6-$OCH_2C_6H_4CF_3(4)$ | |
| 9.81 | $CH_3$ | 5-F,6-$OCH_2C_6H_4CF_3(3)$ | |
| 9.82 | $CH_3$ | 5-F,6-$OCH_2C_6H_4CF_3(2)$ | |
| 9.83 | $CH_3$ | 5-F,6-$OCF_2CHFCF_3$ | |
| 9.84 | $CH_3$ | 5-F,6-$OCF_2CHF_2$ | |
| 9.85 | $CH_3$ | 5-F,6-$OCHF_2$ | |
| 9.86 | $CH_3$ | 5-F,6-$OCF_3$ | |
| 9.87 | $CH_3$ | 5-Cl,6-$OCH_3$ | |
| 9.88 | $CH_3$ | 5-Cl,6-$OCH_2C_6H_4CF_3(4)$ | |

TABLE 9-continued

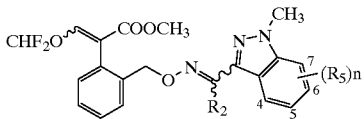

| Compound No. | $R_2$ | $(R_5)n$ | Phys. data |
|---|---|---|---|
| 9.89 | $CH_3$ | 5-Cl,6-$OCH_2C_6H_4CF_3(3)$ | |
| 9.90 | $CH_3$ | 5-Cl,6-$OCH_2C_8H_4CF_3(2)$ | |
| 9.91 | $CH_3$ | 5-Cl,6-$OCH_2(cProp-Cl_2(2,2))$ | |
| 9.92 | $CH_3$ | 5-Br, 6-$OCH_2C_6H_4CF_3(3)$ | |
| 9.93 | $CH_3$ | 5-Br, 6-$OCH_2(cProp-Cl_2(2,2))$ | |
| 9.94 | $CH_3$ | 6-$OCH_2$-$Si(CH_3)_3$ | |
| 9.95 | cProp | H | |
| 9.96 | cProp | 6-$OCH_2(cProp-Cl_2(2,2))$ | |
| 9.97 | cProp | 6-$OCH_2C_6H_4F(4)$ | |
| 9.98 | $CH_3$ | 6-$OCH(CH_3)_2$ | |
| 9.99 | $CH_3$ | 6-$OC(CH_3)_3$ | |
| 9.100 | $CH_3$ | 6-$OCH_2CH(CH_3)_2$ | |
| 9.101 | $CH_3$ | 6-$OCH(CH_3)CH_2CH_3$ | |
| 9.102 | $CH_3$ | 6-$OC_6H_4CF_3(2)$ | |
| 9.103 | $CH_3$ | 6-$OC_6H_4CF_3(3)$ | |
| 9.104 | $CH_3$ | 6-$OC_6H_4Br(4)$ | |
| 9.105 | $CH_3$ | 6-$OC_6H_3F_2(2,4)$ | |

TABLE 10

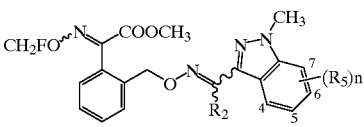

| Compound No. | $R_2$ | $(R_5)n$ | Phys. data |
|---|---|---|---|
| 10.1 | $CH_3$ | H | |
| 10.2 | $CH_3$ | 6-$OCH_3$ | |
| 10.3 | $CH_3$ | 6-$OCH_2(cProp-Cl_2(2,2))$ | |
| 10.4 | $CH_3$ | 6-$OCH_2C_6H_4CF_3(3)$ | |
| 10.5 | $CH_3$ | 6-$OCH_2CH=CH_2$ | |
| 10.6 | $CH_3$ | 6-$OCH_2C\equiv CH$ | |
| 10.7 | $CH_3$ | 6-$OCH_2C_6H_4CF_3(4)$ | |
| 10.8 | $CH_3$ | 6-$OCH_2C_6H_4CF_3(2)$ | |
| 10.9 | $CH_3$ | 5-$OCH_3$ | |
| 10.10 | $CH_3$ | 6-$OCH_2CH=CCl_2$ | |
| 10.11 | $CH_3$ | 6-$OCF_2CHFCF_3$ | |
| 10.12 | $CH_3$ | 6-$OCF_2CF_2CF_3$ | |
| 10.13 | $CH_3$ | 4-F | |
| 10.14 | $CH_3$ | 5-F | |
| 10.15 | $CH_3$ | 6-F | |
| 10.16 | $CH_3$ | 7-F | |
| 10.17 | $CH_3$ | 4-Cl | |
| 10.18 | $CH_3$ | 5-Cl | |
| 10.19 | $CH_3$ | 6-Cl | |
| 10.20 | $CH_3$ | 7-Cl | |
| 10.21 | $CH_3$ | 4-$CH_3$ | |
| 10.22 | $CH_3$ | 5-$CH_3$ | |
| 10.23 | $CH_3$ | 6-$CH_3$ | |
| 10.24 | $CH_3$ | 7-$CH_3$ | |
| 10.25 | $CH_3$ | 4-$CF_3$ | |
| 10.26 | $CH_3$ | 5-$CF_3$ | |
| 10.27 | $CH_3$ | 6-$CF_3$ | |
| 10.28 | $CH_3$ | 7-$CF_3$ | |
| 10.29 | $CH_3$ | 6-$OCF_2CHF_2$ | |
| 10.30 | $CH_3$ | 6-$OCF_2CHFCl$ | |
| 10.31 | $CH_3$ | 6-$OCF_2CHFBr$ | |
| 10.32 | $CH_3$ | 6-$OCHF_2$ | |
| 10.33 | $CH_3$ | 6-$OCF_2Br$ | |
| 10.34 | $CH_3$ | 6-$OCF_3$ | |
| 10.35 | $CH_3$ | 6-$OCH_2(cProp-Br_2(2,2))$ | |
| 10.36 | $CH_3$ | 6-$OCH_2(cProp-CH_2(1)-Cl_2(2,2))$ | |
| 10.37 | $CH_3$ | 6-$OCH_2C(CH_3)=CH_2$ | |
| 10.38 | $CH_3$ | 6-$OCH_2CH_3$ | |

TABLE 10-continued

| Compound No. | R₂ | (R₅)n | Phys. data |
|---|---|---|---|
| 10.39 | CH₃ | 6-OCH₂CH₂CH₃ | |
| 10.40 | CH₃ | 6-OCH₂CH₂CH₂CH₃ | |
| 10.41 | CH₃ | 6-OCH₂C₆H₅ | |
| 10.42 | CH₃ | 6-OCH₂C₆H₄F(2) | |
| 10.43 | CH₃ | 6-OCH₂C₆H₄F(3) | |
| 10.44 | CH₃ | 6-OCH₂C₆H₄F(4) | |
| 10.45 | CH₃ | 6-OCH₂C₆H₄Cl(2) | |
| 10.46 | CH₃ | 6-OCH₂C₆H₄Cl(3) | |
| 10.47 | CH₃ | 6-OCH₂C₆H₄Cl(4) | |
| 10.48 | CH₃ | 6-OCH₂C₆H₄Br(4) | |
| 10.49 | CH₃ | 6-OCH₂C₆H₄OCH₃(4) | |
| 10.50 | CH₃ | 6-OCH₂C₆H₃F₂(2,6) | |
| 10.51 | CH₃ | 6-OCH₂C₆H₃F₂(2,4) | |
| 10.52 | CH₃ | 6-OCH₂C₆H₃F₂(3,4) | |
| 10.53 | CH₃ | 6-OCH₂C₆H₃Cl₂(2,6) | |
| 10.54 | CH₃ | 6-OCH₂C₆H₃Cl₂(2,4) | |
| 10.55 | CH₃ | 6-OCH₂C₆H₃Cl₂(3,4) | |
| 10.56 | CH₃ | 6-OC₆H₅ | |
| 10.57 | CH₃ | 6-OC₆H₄Cl(4) | |
| 10.58 | CH₃ | 6-OC₆H₄F(4) | |
| 10.59 | CH₃ | 6-OC₆H₄CN(4) | |
| 10.60 | CH₃ | 6-OC₆H₄OCH₃(4) | |
| 10.61 | CH₃ | 6-OC₆H₄CF₃(4) | |
| 10.62 | C₂H₅ | H | |
| 10.63 | C₂H₅ | 6-OCH₂(cProp-Cl₂(2,2)) | |
| 10.64 | C₂H₅ | 6-OCH₂C₆H₄F(4) | |
| 10.65 | n-propyl | H | |
| 10.66 | n-propyl | 6-OCH₂(cProp-Cl₂(2,2)) | |
| 10.67 | n-propyl | 6-OCH₂C₆H₄F(4) | |
| 10.68 | CN | H | |
| 10.69 | CN | 6-OCH₂(cProp-Cl₂(2,2)) | |
| 10.70 | CN | 6-OCH₂C₆H₄F(4) | |
| 10.71 | CN | 6-OCH₂C₆H₄CF₃(3) | |
| 10.72 | CN | 6-OCF₂CHFCF₃ | |
| 10.73 | CN | 6-OCH₂CH=CCl₂ | |
| 10.74 | SCF₃ | H | |
| 10.75 | CF₃ | H | |
| 10.76 | CH₃ | 5-F,6-OCH₃ | |
| 10.77 | CH₃ | 5-F,6-OCH₂(cProp-Cl₂(2,2)) | |
| 10.78 | CH₃ | 5-F,6-OCH₂C₆H₄F(4) | |
| 10.79 | CH₃ | 5-F,6-OCH₂C₆H₄Cl(4) | |
| 10.80 | CH₃ | 5-F,6-OCH₂C₆H₄CF₃(4) | |
| 10.81 | CH₃ | 5-F,6-OCH₂C₆H₄CF₃(3) | |
| 10.82 | CH₃ | 5-F,6-OCH₂C₆H₄CF₃(2) | |
| 10.83 | CH₃ | 5-F,6-OCF₂CHFCF₃ | |
| 10.84 | CH₃ | 5-F,6-OCF₂CHF₂ | |
| 10.85 | CH₃ | 5-F,6-OCHF₂ | |
| 10.86 | CH₃ | 5-F,6-OCF₃ | |
| 10.87 | CH₃ | 5-Cl,6-OCH₃ | |
| 10.88 | CH₃ | 5-Cl,6-OCH₂C₆H₄CF₃(4) | |
| 10.89 | CH₃ | 5-Cl,6-OCH₂C₆H₄CF₃(3) | |
| 10.90 | CH₃ | 5-Cl,6-OCH₂C₆H₄CF₃(2) | |
| 10.91 | CH₃ | 5-Cl,6-OCH₂(cProp-Cl₂(2,2)) | |
| 10.92 | CH₃ | 5-Br,6-OCH₂C₆H₄CF₃(3) | |
| 10.93 | CH₃ | 5-Br,6-OCH₂(cProp-Cl₂(2,2)) | |
| 10.94 | CH₃ | 6-OCH₂-Si(CH₃)₃ | |
| 10.95 | cProp | H | |
| 10.96 | cProp | 6-OCH₂(cProp-Cl₂(2,2)) | |
| 10.97 | cProp | 6-OCH₂C₆H₄F(4) | |
| 10.98 | CH₃ | 6-OCH(CH₃)₂ | |
| 10.99 | CH₃ | 6-OC(CH₃)₃ | |
| 10.100 | CH₃ | 6-OCH₂CH(CH₃)₂ | |
| 10.101 | CH₃ | 6-OCH(CH₃)CH₂CH₃ | |
| 10.102 | CH₃ | 6-OC₆H₄CF₃(2) | |
| 10.103 | CH₃ | 6-OC₆H₄CF₃(3) | |
| 10.104 | CH₃ | 6-OC₆H₄Br(4) | |
| 10.105 | CH₃ | 6-OC₆H₃F₂(2,4) | |

TABLE 11

| Compound No. | R₂ | (R₅)n | Phys. data |
|---|---|---|---|
| 11.1 | CH₃ | H | |
| 11.2 | CH₃ | 6-OCH₃ | |
| 11.3 | CH₃ | 6-OCH₂(cProp-Cl₂(2,2)) | |
| 11.4 | CH₃ | 6-OCH₂C₆H₄CF₃(3) | |
| 11.5 | CH₃ | 6-OCH₂CH=CH₂ | |
| 11.6 | CH₃ | 6-OCH₂C≡H | |
| 11.7 | CH₃ | 6-OCH₂C₆H₄CF₃(4) | |
| 11.8 | CH₃ | 6-OCH₂C₆H₄CF₃(2) | |
| 11.9 | CH₃ | 5-OCH₃ | |
| 11.10 | CH₃ | 6-OCH₂CH=CCl₂ | |
| 11.11 | CH₃ | 6-OCF₂CHFCF₃ | |
| 11.12 | CH₃ | 6-OCF₂CF₂CF₃ | |
| 11.13 | CH₃ | 4-F | |
| 11.14 | CH₃ | 5-F | |
| 11.15 | CH₃ | 6-F | |
| 11.16 | CH₃ | 7-F | |
| 11.17 | CH₃ | 4-Cl | |
| 11.18 | CH₃ | 5-Cl | |
| 11.19 | CH₃ | 6-Cl | |
| 11.20 | CH₃ | 7-Cl | |
| 11.21 | CH₃ | 4-CH₃ | |
| 11.22 | CH₃ | 5-CH₃ | |
| 11.23 | CH₃ | 6-CH₃ | |
| 11.24 | CH₃ | 7-CH₃ | |
| 11.25 | CH₃ | 4-CF₃ | |
| 11.26 | CH₃ | 5-CF₃ | |
| 11.27 | CH₃ | 6-CF₃ | |
| 11.28 | CH₃ | 7-CF₃ | |
| 11.29 | CH₃ | 6-OCF₂CHF₂ | |
| 11.30 | CH₃ | 6-OCF₂CHFCl | |
| 11.31 | CH₃ | 6-OCF₂CHFBr | |
| 11.32 | CH₃ | 6-OCHF₂ | |
| 11.33 | CH₃ | 6-OCF₂Br | |
| 11.34 | CH₃ | 6-OCF₃ | |
| 11.35 | CH₃ | 6-OCH₂(cProp-Br₂(2,2)) | |
| 11.36 | CH₃ | 6-OCH₂(cProp-CH₃(1)-Cl₂(2,2)) | |
| 11.37 | CH₃ | 6-OCH₂C(CH₃)=CH₂ | |
| 11.38 | CH₃ | 6-OCH₂CH₃ | |
| 11.39 | CH₃ | 6-OCH₂CH₂CH₃ | |
| 11.40 | CH₃ | 6-OCH₂CH₂CH₂CH₃ | |
| 11.41 | CH₃ | 6-OCH₂C₆H₅ | |
| 11.42 | CH₃ | 6-OCH₂C₆H₄F(2) | |
| 11.43 | CH₃ | 6-OCH₂C₆H₄F(3) | |
| 11.44 | CH₃ | 6-OCH₂C₆H₄F(4) | |
| 11.45 | CH₃ | 6-OCH₂C₆H₄Cl(2) | |
| 11.46 | CH₃ | 6-OCH₂C₆H₄Cl(3) | |
| 11.47 | CH₃ | 6-OCH₂C₆H₄Cl(4) | |
| 11.48 | CH₃ | 6-OCH₂C₆H₄Br(4) | |
| 11.49 | CH₃ | 6-OCH₂C₆H₄OCH₃(4) | |
| 11.50 | CH₃ | 6-OCH₂C₆H₃F₂(2,6) | |
| 11.51 | CH₃ | 6-OCH₂C₆H₃F₂(2,4) | |
| 11.52 | CH₃ | 6-OCH₂C₆H₃F₂(3,4) | |
| 11.53 | CH₃ | 6-OCH₂C₆H₃Cl₂(2,6) | |
| 11.54 | CH₃ | 6-OCH₂C₆H₃Cl₂(2,4) | |
| 11.55 | CH₃ | 6-OCH₂C₆H₃Cl₂(3,4) | |
| 11.56 | CH₃ | 6-OC₆H₅ | |
| 11.57 | CH₃ | 6-OC₆H₄Cl(4) | |
| 11.58 | CH₃ | 6-OC₆H₄F(4) | |
| 11.59 | CH₃ | 6-OC₆H₄CN(4) | |
| 11.60 | CH₃ | 6-OC₆H₄OCH₃(4) | |
| 11.61 | CH₃ | 6-OC₆H₄CF₃(4) | |
| 11.62 | C₂H₅ | H | |
| 11.63 | C₂H₅ | 6-OCH₂(cProp-Cl₂(2,2)) | |
| 11.64 | C₂H₅ | 6-OCH₂C₆H₄F(4) | |
| 11.65 | n-propyl | H | |

TABLE 11-continued

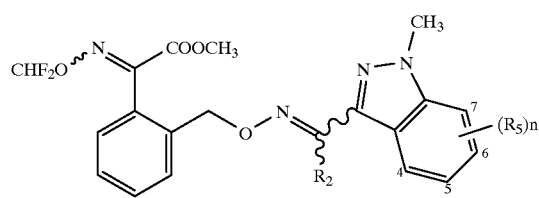

| Compound No. | $R_2$ | $(R_5)n$ | Phys. data |
|---|---|---|---|
| 11.66 | n-propyl | 6-OCH$_2$(cProp-Cl$_2$(2,2)) | |
| 11.67 | n-propyl | 6-OCH$_2$C$_6$H$_4$F(4) | |
| 11.68 | CN | H | |
| 11.69 | CN | 6-OCH$_2$(cProp-Cl$_2$(2,2)) | |
| 11.70 | CN | 6-OCH$_2$C$_6$H$_4$F(4) | |
| 11.71 | CN | 6-OCH$_2$C$_6$H$_4$CF$_3$(3) | |
| 11.72 | CN | 6-OCF$_2$CHFCF$_3$ | |
| 11.73 | CN | 6-OCH$_2$CH=CCl$_2$ | |
| 11.74 | SCF$_3$ | H | |
| 11.75 | CF$_3$ | H | |
| 11.76 | CH$_3$ | 5-F, 6-OCH$_3$ | |
| 11.77 | CH$_3$ | 5-F, 6-OCH$_2$(cProp-Cl$_2$(2,2)) | |
| 11.78 | CH$_3$ | 5-F, 6-OCH$_2$C$_6$H$_4$F(4) | |
| 11.79 | CH$_3$ | 5-F, 6-OCH$_2$C$_6$H$_4$Cl(4) | |
| 11.80 | CH$_3$ | 5-F, 6-OCH$_2$C$_6$H$_4$CF$_3$(4) | |
| 11.81 | CH$_3$ | 5-F, 6-OCH$_2$C$_6$H$_4$CF$_3$(3) | |
| 11.82 | CH$_3$ | 5-F, 6-OCH$_2$C$_6$H$_4$CF$_3$(2) | |
| 11.83 | CH$_3$ | 5-F, 6-OCF$_2$CHFCF$_3$ | |
| 11.84 | CH$_3$ | 5-F, 6-OCF$_2$CHF$_2$ | |
| 11.85 | CH$_3$ | 5-F, 6-OCHF$_2$ | |
| 11.86 | CH$_3$ | 5-F, 6-OCF$_3$ | |
| 11.87 | CH$_3$ | 5-Cl, 6-OCH$_3$ | |
| 11.88 | CH$_3$ | 5-Cl, 6-OCH$_2$C$_6$H$_4$CF$_3$(4) | |
| 11.89 | CH$_3$ | 5-Cl, 6-OCH$_2$C$_6$H$_4$CF$_3$(3) | |
| 11.90 | CH$_3$ | 5-Cl, 6-OCH$_2$C$_6$H$_4$CF$_3$(2) | |
| 11.91 | CH$_3$ | 5-Cl, 6-OCH$_2$(cProp-Cl$_2$(2,2)) | |
| 11.92 | CH$_3$ | 5-Br, 6-OCH$_2$C$_6$H$_4$CF$_3$(3) | |
| 11.93 | CH$_3$ | 5-Br, 6-OCH$_2$(cProp-Cl$_2$(2,2)) | |
| 11.94 | CH$_3$ | 6-OCH$_2$-Si(CH$_3$)$_3$ | |
| 11.95 | cProp | H | |
| 11.96 | cProp | 6-OCH$_2$(cProp-Cl$_2$(2,2)) | |
| 11.97 | cProp | 6-OCH$_2$C$_6$H$_4$F(4) | |
| 11.98 | CH$_3$ | 6-OCH(CH$_3$)$_2$ | |
| 11.99 | CH$_3$ | 6-OC(CH$_3$)$_3$ | |
| 11.100 | CH$_3$ | 6-OCH$_2$CH(CH$_3$)$_2$ | |
| 11.101 | CH$_3$ | 6-OCH(CH$_3$)CH$_2$CH$_3$ | |
| 11.102 | CH$_3$ | 6-OC$_6$H$_4$CF$_3$(2) | |
| 11.103 | CH$_3$ | 6-OC$_6$H$_4$CF$_3$(3) | |
| 11.104 | CH$_3$ | 6-OC$_6$H$_4$Br(4) | |
| 11.105 | CH$_3$ | 6-OC$_6$H$_3$F$_2$(2,4) | |

TABLE 12

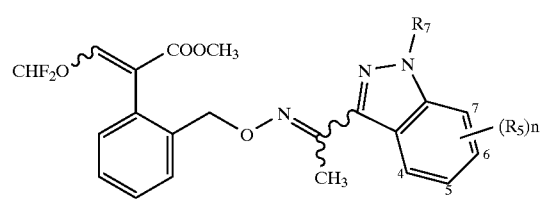

| Compound No. | $R_7$ | $(R_5)n$ | Phys. data |
|---|---|---|---|
| 12.1 | H | H | |
| 12.2 | H | 6-OCH$_3$ | |
| 12.3 | H | 6-OCH$_2$(cProp-Cl$_2$(2,2)) | |
| 12.4 | H | 6-OCH$_2$C$_8$H$_4$CF$_3$(3) | |
| 12.5 | H | 6-F | |
| 12.6 | H | 6-CF$_3$ | |

TABLE 12-continued

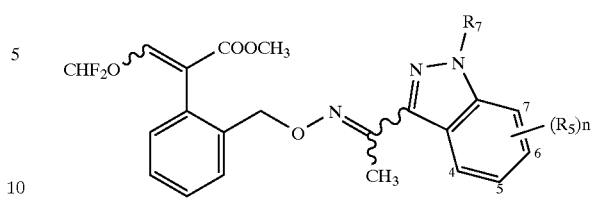

| Compound No. | $R_7$ | $(R_5)n$ | Phys. data |
|---|---|---|---|
| 12.7 | H | 6-OCH$_2$C$_6$H$_4$F(4) | |
| 12.8 | H | 6-OCH$_2$Si(CH$_3$)$_3$ | |
| 12.9 | H | 6-OC$_2$H$_5$ | |
| 12.10 | H | 6-OCH$_2$CH$_2$CH$_3$ | |
| 12.11 | C$_2$H$_5$ | H | |
| 12.12 | C$_2$H$_5$ | 6-OCH$_3$ | |
| 12.13 | C$_2$H$_5$ | 6-OCH$_2$(cProp-Cl$_2$(2,2)) | |
| 12.14 | C$_2$H$_5$ | 6-OCH$_2$C$_6$H$_4$CF$_3$(3) | |
| 12.15 | C$_2$H$_5$ | 6-F | |
| 12.16 | C$_2$H$_5$ | 6-CF$_3$ | |
| 12.17 | C$_2$H$_5$ | 6-OCH$_2$C$_6$H$_4$F(4) | |
| 12.18 | C$_2$H$_5$ | 6-OCH$_2$Si(CH$_3$)$_3$ | |
| 12.19 | C$_2$H$_5$ | 6-OC$_2$H$_5$ | |
| 12.20 | C$_2$H$_5$ | 6-OCH$_2$CH$_2$CH$_3$ | |
| 12.21 | CH$_2$CH$_2$CH$_3$ | H | |
| 12.22 | CH$_2$CH$_2$CH$_3$ | 6-OCH$_3$ | |
| 12.23 | CH$_2$CH$_2$CH$_3$ | 6-OCH$_2$(cProp-Cl$_2$(2,2)) | |
| 12.24 | CH$_2$CH$_2$CH$_3$ | 6-OCH$_2$C$_6$H$_4$CF$_3$(3) | |
| 12.25 | CH$_2$CH$_2$CH$_3$ | 6-F | |
| 12.26 | CH$_2$CH$_2$CH$_3$ | 6-CF$_3$ | |
| 12.27 | CH$_2$CH$_2$CH$_3$ | 6-OCH$_2$C$_6$H$_4$F(4) | |
| 12.28 | CH$_2$CH$_2$CH$_3$ | 6-OCH$_2$Si(CH$_3$)$_3$ | |
| 12.29 | CH$_2$CH$_2$CH$_3$ | 6-OC$_2$H$_5$ | |
| 12.30 | CH$_2$CH$_2$CH$_3$ | 6-OCH$_2$CH$_2$CH$_3$ | |
| 12.31 | CH(CH$_3$)$_2$ | H | |
| 12.32 | CH(CH$_3$)$_2$ | 6-OCH$_3$ | |
| 12.33 | CH(CH$_3$)$_2$ | 6-OCH$_2$(cProp-Cl$_2$(2,2)) | |
| 12.34 | CH(CH$_3$)$_2$ | 6-OCH$_2$C$_6$H$_4$CF$_3$(3) | |
| 12.35 | CH(CH$_3$)$_2$ | 6-F | |
| 12.36 | CH(CH$_3$)$_2$ | 6-CF$_3$ | |
| 12.37 | CH(CH$_3$)$_2$ | 6-OCH$_2$C$_6$H$_4$F(4) | |
| 12.38 | CH(CH$_3$)$_2$ | 6-OCH$_2$Si(CH$_3$)$_3$ | |
| 12.39 | CH(CH$_3$)$_2$ | 6-OC$_2$H$_5$ | |
| 12.40 | CH(CH$_3$)$_2$ | 6-OCH$_2$CH$_2$CH$_3$ | |

TABLE 13

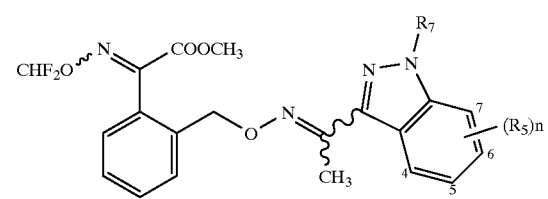

| Compound No. | $R_7$ | $(R_5)n$ | Phys. data |
|---|---|---|---|
| 13.1 | H | H | |
| 13.2 | H | 6-OCH$_3$ | |
| 13.3 | H | 6-OCH$_2$(cProp-Cl$_2$(2,2)) | |
| 13.4 | H | 6-OCH$_2$C$_6$H$_4$CF$_3$(3) | |
| 13.5 | H | 6-F | |
| 13.6 | H | 6-CF$_3$ | |
| 13.7 | H | 6-OCH$_2$C$_6$H$_4$F(4) | |
| 13.8 | H | 6-OCH$_2$Si(CH$_3$)$_3$ | |
| 13.9 | H | 6-OC$_2$H$_5$ | |
| 13.10 | H | 6-OCH$_2$CH$_2$CH$_3$ | |
| 13.11 | C$_2$H$_5$ | H | |
| 13.12 | C$_2$H$_5$ | 6-OCH$_3$ | |

TABLE 13-continued

Structure: CHF₂O-N=C(COOCH₃)-C₆H₄-CH₂-O-N=C(CH₃)-[indazole with R₇ on N1, (R₅)n on ring]

| Compound No. | $R_7$ | $(R_5)n$ | Phys. data |
|---|---|---|---|
| 13.13 | $C_2H_5$ | 6-OCH$_2$(cProp-Cl$_2$(2,2)) | |
| 13.14 | $C_2H_5$ | 6-OCH$_2$C$_6$H$_4$CF$_3$(3) | |
| 13.15 | $C_2H_5$ | 6-F | |
| 13.16 | $C_2H_5$ | 6-CF$_3$ | |
| 13.17 | $C_2H_5$ | 6-OCH$_2$C$_6$H$_4$F(4) | |
| 13.18 | $C_2H_5$ | 6-OCH$_2$Si(CH$_3$)$_3$ | |
| 13.19 | $C_2H_5$ | 6-OC$_2$H$_5$ | |
| 13.20 | $C_2H_5$ | 6-OCH$_2$CH$_2$CH$_3$ | |
| 13.21 | CH$_2$CH$_2$CH$_3$ | H | |
| 13.22 | CH$_2$CH$_2$CH$_3$ | 6-OCH$_3$ | |
| 13.23 | CH$_2$CH$_2$CH$_3$ | 6-OCH$_2$(cProp-Cl$_2$(2,2)) | |
| 13.24 | CH$_2$CH$_2$CH$_3$ | 6-OCH$_2$C$_6$H$_4$CF$_3$(3) | |
| 13.25 | CH$_2$CH$_2$CH$_3$ | 6-F | |
| 13.26 | CH$_2$CH$_2$CH$_3$ | 6-CF$_3$ | |
| 13.27 | CH$_2$CH$_2$CH$_3$ | 6-OCH$_2$C$_6$H$_4$F(4) | |
| 13.28 | CH$_2$CH$_2$CH$_3$ | 6-OCH$_2$Si(CH$_3$)$_3$ | |
| 13.29 | CH$_2$CH$_2$CH$_3$ | 6-OC$_2$H$_5$ | |
| 13.30 | CH$_2$CH$_2$CH$_3$ | 6-OCH$_2$CH$_2$CH$_3$ | |
| 13.31 | CH(CH$_3$)$_2$ | H | |
| 13.32 | CH(CH$_3$)$_2$ | 6-OCH$_3$ | |
| 13.33 | CH(CH$_3$)$_2$ | 6-OCH$_2$(cProp-Cl$_2$(2,2)) | |
| 13.34 | CH(CH$_3$)$_2$ | 6-OCH$_2$C$_6$H$_4$CF$_3$(3) | |
| 13.35 | CH(CH$_3$)$_2$ | 6-F | |
| 13.36 | CH(CH$_3$)$_2$ | 6-CF$_3$ | |
| 13.37 | CH(CH$_3$)$_2$ | 6-OCH$_2$C$_6$H$_4$F(4) | |
| 13.38 | CH(CH$_3$)$_2$ | 6-OCH$_2$Si(CH$_3$)$_3$ | |
| 13.39 | CH(CH$_3$)$_2$ | 6-OC$_2$H$_5$ | |
| 13.40 | CH(CH$_3$)$_2$ | 6-OCH$_2$CH$_2$CH$_3$ | |

TABLE 14

Structure: CHF₂O-N=C(CONHCH₃)-C₆H₄-CH₂-O-N=C(CH₃)-[indazole with R₇ on N1, (R₅)n on ring]

| Compound No. | $R_7$ | $(R_5)n$ | Phys. data |
|---|---|---|---|
| 14.1 | H | H | |
| 14.2 | H | 6-OCH$_3$ | |
| 14.3 | H | 6-OCH$_2$(cProp-Cl$_2$(2,2)) | |
| 14.4 | H | 6-OCH$_2$C$_6$H$_4$CF$_3$(3) | |
| 14.5 | H | 6-F | |
| 14.6 | H | 6-CF$_3$ | |
| 14.7 | H | 6-OCH$_2$C$_6$H$_4$F(4) | |
| 14.8 | H | 6-OCH$_2$Si(CH$_3$)$_3$ | |
| 14.9 | H | 6-OC$_2$H$_5$ | |
| 14.10 | H | 6-OCH$_2$CH$_2$CH$_3$ | |
| 14.11 | $C_2H_5$ | H | |
| 14.12 | $C_2H_5$ | 6-OCH$_3$ | |
| 14.13 | $C_2H_5$ | 6-OCH$_2$(cProp-Cl$_2$(2,2)) | |
| 14.14 | $C_2H_5$ | 6-OCH$_2$C$_6$H$_4$CF$_3$(3) | |
| 14.15 | $C_2H_5$ | 6-F | |
| 14.16 | $C_2H_5$ | 6-CF$_3$ | |
| 14.17 | $C_2H_5$ | 6-OCH$_2$C$_6$H$_4$F(4) | |
| 14.18 | $C_2H_5$ | 6-OCH$_2$Si(CH$_3$)$_3$ | |
| 14.19 | $C_2H_5$ | 6-OC$_2$H$_5$ | |
| 14.20 | $C_2H_5$ | 6-OCH$_2$CH$_2$CH$_3$ | |
| 14.21 | CH$_2$CH$_2$CH$_3$ | H | |
| 14.22 | CH$_2$CH$_2$CH$_3$ | 6-OCH$_3$ | |
| 14.23 | CH$_2$CH$_2$CH$_3$ | 6-OCH$_2$(cProp-Cl$_2$(2,2)) | |
| 14.24 | CH$_2$CH$_2$CH$_3$ | 6-OCH$_2$C$_6$H$_4$CF$_3$(3) | |
| 14.25 | CH$_2$CH$_2$CH$_3$ | 6-F | |
| 14.26 | CH$_2$CH$_2$CH$_3$ | 6-CF$_3$ | |
| 14.27 | CH$_2$CH$_2$CH$_3$ | 6-OCH$_2$C$_6$H$_4$F(4) | |
| 14.28 | CH$_2$CH$_2$CH$_3$ | 6-OCH$_2$Si(CH$_3$)$_3$ | |
| 14.29 | CH$_2$CH$_2$CH$_3$ | 6-OC$_2$H$_5$ | |
| 14.30 | CH$_2$CH$_2$CH$_3$ | 6-OCH$_2$CH$_2$CH$_3$ | |
| 14.31 | CH(CH$_3$)$_2$ | H | |
| 14.32 | CH(CH$_3$)$_2$ | 6-OCH$_3$ | |
| 14.33 | CH(CH$_3$)$_2$ | 6-OCH$_2$(cProp-Cl$_2$(2,2)) | |
| 14.34 | CH(CH$_3$)$_2$ | 6-OCH$_2$C$_6$H$_4$CF$_3$(3) | |
| 14.35 | CH(CH$_3$)$_2$ | 6-F | |
| 14.36 | CH(CH$_3$)$_2$ | 6-CF$_3$ | |
| 14.37 | CH(CH$_3$)$_2$ | 6-OCH$_2$C$_6$H$_4$F(4) | |
| 14.38 | CH(CH$_3$)$_2$ | 6-OCH$_2$Si(CH$_3$)$_3$ | |
| 14.39 | CH(CH$_3$)$_2$ | 6-OC$_2$H$_5$ | |
| 14.40 | CH(CH$_3$)$_2$ | 6-OCH$_2$CH$_2$CH$_3$ | |

Example P7

2-(Bromomethyl)-phenylglyoxylic Acid Methyl Ester O-fluoromethyloxime (Formula II, X=N, $R_1$= methyl, $R_3$=$R_4$=H, $R_9$=CH$_2$F, $X_1$=Br)

a) A mixture of 57 g of 2-tolylglyoxylic acid methyl ester oxime and 80 g of powdered potassium carbonate is mixed into 550 ml of dimethyl sulfoxide for 30 minutes at room temperature and then a solution of 40 g of bromofluoromethane in 30 ml of dimethyl sulfoxide is added dropwise at room temperature. The reaction mixture is stirred for a further 20 hours and then poured into 1200 ml of water, neutralised with 230 ml of hydrochloric acid and extracted four times with 250 ml of ethyl acetate each time. The combined organic phases are washed with 200 ml of saturated sodium chloride solution, dried with sodium sulfate and concentrated by evaporation in vacuo. Purification by flash chromatography (silica gel, ethyl acetate/hexane 1:9) yields 2-tolylglyoxylic acid methyl ester O-fluoromethyloxime in the form of a viscous oil.

b) 56 g of 2-tolylglyoxylic acid methyl ester O-fluoromethyloxime and 0.4 g of dibenzoyl peroxide are dissolved in 350 ml of carbon tetrachloride and heated to boiling. Then, with irradiation with a lamp, 44.5 g of N-bromosuccinimide are added in small portions, stirring is continued for 2 hours and, after cooling, the succinimide that has precipitated is filtered off. The solution is then concentrated by evaporation. Purification by flash chromatography (sililca gel, ethyl acetate/hexane 1:1) of the residue yields the title compound in the form of a viscous oil.

Example P8

2-Bromomethylphenylglyoxylic Acid Methyl Ester O-difluoromethyloxime (Formula II, X=N, $R_1$= methyl, $R_3$=$R_4$=H, $R_9$=CHF$_2$, $X_1$=Br)

a) At 10–20° C., 28.4 g of potassium tert-butanolate are introduced into a solution of 19.35 g of 2-tolylglyoxylic acid methyl ester oxime in 250 ml of 1,2-dimethoxyethane. As soon as a fine suspension has formed, chlorodifluoromethane is introduced at 25–30° C. After 5 hours, the reaction mixture is concentrated by evaporation in vacuo, water is added to the residue and the product is weakly acidified with 2N hydrochloric acid and extracted several times with ethyl acetate. After washing and concentrating the combined organic phases by evaporation, purification is carried out by flash chromatography (silica gel, ethyl acetate/hexane 1:5), yielding 2-tolylglyoxylic acid methyl ester O-difluoromethyloxime in the form of a yellow oil.

b) A solution of 5.1 g of 2-tolylglyoxylic acid methyl ester O-difluoromethyloxime and 0.16 g of dibenzoyl peroxide in 40 ml of carbon tetrachloride is heated to boiling. Then, with irradiation with a lamp, 3.55 g of N-bromosuccinimide are added in small portions and boiling is continued for 30 minutes. After cooling, the succinimide that has precipitated is filtered off, the solution is concentrated by evaporation, and the residue is purified by flash chromatography (silica gel, ethyl acetate/hexane 1:6), yielding the title compound in the form of a light-yellow oil.

Formulation Examples

Throughout, Percentages are by Weight

| Example F1: Emulsifiable concentrates | a) | b) | c) |
|---|---|---|---|
| active ingredient | 25% | 40% | 50% |
| calcium dodecylbenzenesulfonate | 5% | 8% | 6% |
| castor oil polyethylene glycol ether (36 mol EO) | 5% | — | — |
| tributylphenol polyethylene glycol ether (30 mol EO) | — | 12% | 4% |
| cyclohexanone | — | 15% | 20% |
| xylene mixture | 65% | 25% | 20% |

The finely ground active ingredient is mixed with the adjuvants, giving an emulsifiable concentrate which can be diluted with water to give emulsions of any desired concentration.

| Example F2: Solutions | a) | b) | c) | d) |
|---|---|---|---|---|
| active ingredient | 80% | 10% | 5% | 95% |
| ethylene glycol monomethyl ether | 20% | — | — | — |
| polyethylene glycol (mol. wt. 400) | — | 70% | — | — |
| N-methylpyrrolid-2-one | — | 20% | — | — |
| epoxidised coconut oil | — | — | 1% | 5% |
| petroleum fraction (boiling range: 160–190) | — | — | 94% | — |

The finely ground active ingredient is mixed with the adjuvants, giving a solution that is suitable for use in the form of microdrops.

| Example F3: Granules | a) | b) | c) | d) |
|---|---|---|---|---|
| active ingredient | 5% | 10% | 8% | 21% |
| kaolin | 94% | — | 79% | 54% |
| highly dispersed silicic acid | 1% | — | 13% | 7% |
| attapulgite | — | 90% | — | 18% |

The active ingredient is dissolved in dichloromethane and the solution is sprayed onto the carrier mixture and the solvent is evaporated off in vacuo.

| Example F4: Dusts | a) | b) |
|---|---|---|
| active ingredient | 2% | 5% |
| highly dispersed silicic acid | 1% | 5% |
| talcum | 97% | — |
| kaolin | — | 90% |

The active ingredient is mixed with the carriers, giving dusts that are ready for use.

| Example F5: Wettable powders | a) | b) | c) |
|---|---|---|---|
| active ingredient | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 mol EO) | — | 2% | — |
| highly dispersed silicic acid | 5% | 10% | 10% |
| kaolin | 62% | 27% | — |

The active ingredient is mixed with the adjuvants and the mixture is ground in a suitable mill, affording wettable powders which can be diluted with water to give suspensions of the desired concentration.

| Example F6: Emulsifiable concentrate | |
|---|---|
| active ingredient | 10% |
| octylphenol polyethylene glycol ether (4–5 mol EO) | 3% |
| calcium dodecylbenzenesulfonate | 3% |
| castor oil polyethylene glycol ether (36 mol EO) | 4% |
| cyclohexanone | 30% |
| xylene mixture | 50% |

The finely ground active ingredient is mixed with the adjuvants, giving an emulsifiable concentrate which can be diluted with water to give emulsions of any desired concentration.

| Example F7: Dusts | a) | b) |
|---|---|---|
| active ingredient | 5% | 8% |
| talcum | 95% | — |
| kaolin | — | 92% |

Ready-for-use dusts are obtained by mixing the active ingredient with the carrier and grinding the mixture in a suitable mill.

| Example F8: Extruder granules | |
|---|---|
| active ingredient | 10% |
| sodium lignosulfonate | 2% |
| carboxymethylcellulose | 1% |
| kaolin | 87% |

The active ingredient is mixed with the adjuvants and the mixture is ground and moistened with water. The mixture is extruded and granulated and the granules are dried in a stream of air.

| Example F9: Coated granules | |
| --- | --- |
| active ingredient | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granules are obtained in this manner.

| Example F10: Suspension concentrate | |
| --- | --- |
| active ingredient | 40% |
| ethylene glycol | 10% |
| nonylphenol polyethylene glycol ether (15 mol EO) | 6% |
| sodium lignosulfonate | 10% |
| carboxymethylcellulose | 1% |
| aqueous formaldehyde solution (37%) | 0.2% |
| aqueous silicone oil emulsion (75%) | 0.8% |
| water | 32% |

The finely ground active ingredient is mixed with the adjuvants, giving a suspension concentrate from which suspensions of any desired concentration can be obtained by dilution with water.

Biological Examples

A) Microbicidal Action

Example B1

Action Against Phytophthora Infestans on Tomatoes a) Curative action

After a cultivation period of 3 weeks, tomato plants of the "Red Gnome" variety are sprayed with a zoospore suspension of the fungus and incubated in a cabinet at 18 to 20° and 100% humidity. Humidification is stopped after 24 hours. When the plants have dried, they are sprayed with a mixture comprising the test compound formulated as a wettable powder in a concentration of 200 ppm. After the spray coating has dried, the plants are again placed in the humidity cabinet for 4 days. The activity of the test compounds is evaluated on the basis of the number and size of the typical leaf specks that have occurred after that time.

b) Preventive-systemic action

The test compound formulated as a wettable powder is applied in a concentration of 60 ppm (based on the volume of the soil) to the soil surface of three-week-old tomato plants of the "Red Gnome" variety planted in pots. After a 3-day waiting period, the undersides of the leaves of the plants are sprayed with a zoospore suspension of Phytophthora infestans. The plants are then kept in a spray cabinet for 5 days at 18 to 20° C. and 100% humidity. After that time, typical leaf specks form, the number and size of which are used to evaluate the activity of the test compounds.

While infestation is 100% on untreated and infected control plants, the compounds of formula I according to one of Tables 3 to 14 reduce infestation to 20% or less in both tests. Compounds 3.1, 3.2 and 3.15 are almost completely effective.

Example B2

Action Against *Plasmopara viticola* (Bert. et Curt.) (Berl. et DeToni) on Vines a) Residual-preventive action Vine seedlings of the "Chasselas" variety are grown in a greenhouse. 3 plants are sprayed at the 10-leaf stage with a mixture (200 ppm active ingredient). After the spray coating has dried, the undersides of the leaves of the plants are infected uniformly with a spore suspension of the fungus. The plants are then kept in a humidity chamber for 8 days. After that time, the control plants exhibit marked symptoms of disease. The activity of the test compounds is evaluated on the basis of the number and size of the sites of infection on the treated plants.

b) Curative action

Vine seedlings of the "Chasselas" variety are grown in a greenhouse and the undersides of the leaves are infected at the 1 0-leaf stage with a spore suspension of *Plasmopara viticola*. After 24 hours in a humidity cabinet, the plants are sprayed with a mixture of the test compound (200 ppm active ingredient). Then the plants are kept in the humidity cabinet for a further 7 days. After that time, the control plants exhibit symptoms of disease. The activity of the test compounds is evaluated on the basis of the number and size of the sites of infection on the treated plants.

In comparison with the control plants, infestation is 20% or less on the plants treated with compounds of formula I.

Example B3

Action Against *Pythium debaryanum* on sugar beet (*Beta vulgaris*)

a) Action following soil application

The fungus is cultivated on sterile oat grains and added to a soil/sand mixture. The soil so infected is introduced into plant pots and sown with sugar beet seeds. Immediately after sowing, a wettable powder formulation of the test compounds is poured in the form of an aqueous suspension over the soil (20 ppm active ingredient, based on the volume of the soil). The pots are then placed in a greenhouse at 20–24° C. for 2–3 weeks. The soil is kept uniformly moist by light spraying with water. The test is evaluated by determining the emergence of the sugar beet plants and the number of healthy and diseased plants.

b) Action following application by dressing

The fungus is cultivated on sterile oat grains and added to a soil/sand mixture. The soil so infected is introduced into plant pots and sown with sugar beet seeds which have been dressed with the test compounds formulated as dressing powders (1000 ppm active ingredient, based on the weight of the seeds). The pots containing the seeds are then placed in a greenhouse at 20–24° C. for 2–3 weeks. The soil is kept uniformly moist by light spraying with water.

The test is evaluated by determining the emergence of the sugar beet plants and the number of healthy and diseased plants.

Following treatment with compounds of formula I, over 80% of the plants emerge and have a healthy appearance. In the control pots, only the occasional emerged plant, with a diseased appearance, is observed.

Example B4

Residual-protective Action Against *Cercospora arachidicola* on Groundnuts 10 to 15 cm high groundnut plants are sprayed to drip point with an aqueous spray mixture (0.02% active ingredient) and are infected 48 hours later with a conidia suspension of the fungus. The plants are incubated for 72 hours at 21° C. and high humidity and are then placed in a greenhouse until the typical leaf specks occur. The activity of the test compound is evaluated 12 days after infection and is based on the number and size of the leaf specks.

Compounds of formula I bring about a reduction in leaf specks to less than about 10% of the leaf surface. In some cases, the disease is inhibited completely (0–5% infestation).

Example B5

Action Against *Puccinia graminis* on Wheat
a) Residual-protective action 6 days after sowing, wheat plants are sprayed to drip point with an aqueous spray mixture (0.02% active ingredient) and are infected 24 hours later with a uredospore suspension of the fungus. After an incubation period of 48 hours (conditions: 95 to 100% relative humidity at 20° C.), the plants are placed in a greenhouse at 22° C. Evaluation of rust pustule development is made 12 days after infection.
b) Systemic action 5 days after sowing, wheat plants are watered with an aqueous spray mixture (0.006% active ingredient, based on the volume of the soil). Care is taken that the spray mixture does not come into contact with the parts of the plants above the soil. After 48 hours the plants are infected with a uredospore suspension of the fungus. After an incubation period of 48 hours (conditions: 95 to 100% relative humidity at 20° C.), the plants are placed in a greenhouse at 22° C. Evaluation of rust pustule development is made 12 days after infection. Compounds of formula I effect a marked reduction in fungus infestation. In particular, compounds 3.1, 3.2, 3.15, 4.15 and 4.27 effect a reduction in fungus infestation of more than 90%.

Example B6

Action Against *Pyricularia oryzae* on Rice
a) Residual-protective action

After a cultivation period of 2 weeks, rice plants are sprayed to drip point with an aqueous spray mixture (0.02% active ingredient) and are infected 48 hours later with a conidia suspension of the fungus. Evaluation of fungus infestation is made 5 days after infection, during which period 95 to 100% relative humidity and a temperature of 22° C. are maintained.
b) Systemic action 2-week-old rice plants are watered with an aqueous spray mixture (0.006% active ingredient, based on the volume of the soil). Care is taken that the spray mixture does not come into contact with the parts of the plants above the soil. The pots are then filled with water so that the lowermost parts of the stems of the rice plants stand in water. After 96 hours, the plants are infected with a conidia suspension of the fungus and are kept for 5 days at 95 to 100% relative humidity and a temperature of 24° C.

Compounds of formula I largely prevent the disease from breaking out on the infected plants. In particular, compounds 3.1, 3.2, 3.15, 4.15 and 4.27 effect a reduction in fungus infestation of more than 90%.

Example B7

Residual-protective Action Against *Venturia inaegualis* on Apples

Apple cuttings with 10–20 cm long fresh shoots are sprayed to drip point with a spray mixture (0.02% active ingredient) and are infected 24 hours later with a conidia suspension of the fungus. The plants are incubated for 5 days at 90 to 100% relative humidity and are placed for a further 10 days in a greenhouse at 20 to 24° C. Scab infestation is evaluated 15 days after infection.

Compounds of formula I of one of Tables 3 to 14 mainly have a lasting effect against scab diseases. In particular, compounds 3.1, 3.2, 3.15 and 4.15 effect a reduction in fungus infestation of more than 90%.

Example B8

Action Against *Erysiphe graminis* on Barley
a) Residual-protective action

Barley plants about 8 cm in height are sprayed to drip point with an aqueous spray mixture (0.02% active ingredient) and are dusted 3 to 4 hours later with conidia of the fungus. The infected plants are placed in a greenhouse at 22° C. Fungus infestation is evaluated 10 days after infection.
b) Systemic action Barley plants about 8 cm in height are watered with an aqueous spray mixture (0.002% active ingredient, based on the volume of the soil). Care is taken that the spray mixture does not come into contact with the parts of the plants above the soil. The plants are dusted 48 hours later with conidia of the fungus. The infected plants are placed in a greenhouse at 22° C. Evaluation of fungus infestation is made 10 days after infection.

Compounds of formula I are generally able to reduce disease infestation to less than 20%, and in some cases even completely. Compounds 3.1, 3.2, 3.15, 4.15 and 4.27 reduce fungus infestation to less than 5%.

Example B9

Action Against *Podosphaera Leucotricha* on Apple Shoots

Residual-protective action

Apple cuttings with about 15 cm long fresh shoots are sprayed with a spray mixture (0.06% active ingredient). After 24 hours, the treated plants are infected with a conidia suspension of the fungus and are placed in a climatic chamber at 70% relative humidity and 20° C. Fungus infestation is evaluated 12 days after infection.

Following treatment with compounds of formula I disease infestation is less than 20%. Control plants exhibit 100% infestation. Compounds 3.1 and 3.2 reduce fungus infestation to less than 5%.

Example B10

Action Against *Botrytis cinerea* on Apple Fruits
Residual-protective action

Artificially damaged apples are treated by dropping a spray mixture (0.02% active ingredient) onto the damaged sites. The treated fruits are then inoculated with a spore suspension of the fungus and are incubated for one week at high humidity and about 20° C. The fungicidal activity of the test compound is derived from the number of rotted damaged sites.

The compounds of formula I of Tables 3 to 14 are able to prevent the rot from spreading, in some cases completely. In particular, compounds 3.1, 3.2, 3.15 and 4.15 reduce fungus infestation to less than 5%.

Example B11

Action Against *Helminthosporium gramineum*

Wheat grains are contaminated with a spore suspension of the fungus and are left to dry. The contaminated grains are dressed with a suspension of the test compound (600 ppm active ingredient, based on the weight of the seeds). 2 days later, the grains are placed on suitable agar dishes and, after a further four days, the development of the fungus colonies around the grains is assessed. The evaluation of the test compound is based on the number and size of the fungus colonies.

Some of the compounds of formula I exhibit good activity, i.e. inhibition of the fungus colonies. In particular, compounds 3.1, 3.2, 3.15, 4.15 and 4.27 reduce fungus infestation to less than 5%.

Example B12

Action Against *Colletotrichum lagenarium* on Cucumbers

After a cultivation period of 2 weeks, cucumber plants are sprayed with a spray mixture (concentration 0.002%). 2 days later, the plants are infected with a spore suspension (1.5× $10^5$ spores/ml) of the fungus and are incubated for 36 hours at 23° C. and high humidity. Incubation is then continued at normal humidity and about 22–23° C. The fungus infestation that has occurred is evaluated 8 days after infection. Fungus infestation is 100% on untreated and infected control plants.

The compounds of formula I inhibit infestation with the disease in some cases almost completely. In particular, compounds 3.1, 3.2, 3.3, 3.4, 3.15, 3.36, 4.27 and 5.103 reduce fungus infestation to less than 5%.

Example B13

Action Against *Fusarium nivale* on Rye

Rye of the Tetrahell variety which is naturally infected with *Fusarium nivale* is dressed in a roller mixer with the test fungicide, the following concentrations being used: 20 or 6 ppm a.i. (based on the weight of the seed).

The infected and treated rye is sown in October in the open with a seeder in plots 3 meters long and in 6 rows. Three replicates are carried out with each concentration.

Until evaluation of the infestation is made, the test crop is cultivated under normal field conditions (preferably in a region with unbroken snow cover during the winter months).

In order to evaluate the phytotoxicity, the emergence is assessed in the autumn and the crop density/number of plants per unit area is assessed in the spring.

To determine the effectiveness of the test compounds, the percentage of plants attacked by Fusarium is calculated in the spring immediately after the snow has melted. The number of infested plants is less than 5% in the present case. The plants that have emerged have a healthy appearance.

Example B14

Action Against *Sepdtoria nodorum* on Wheat

Wheat plants are sprayed at the 3-leaf stage with a spray mixture (60 ppm a.i.) prepared from a wettable powder formulation of the test compounds. 24 hours later, the treated plants are infected with a conidia suspension of the fungus. The plants are then incubated for 2 days at 90–100% relative humidity and are placed in a greenhouse for a further 10 days at 20–24° C. Fungus infestation is evaluated 13 days after infection. Less than 1% of the wheat plants are infested.

Example B15

Action Against *Rhizoctonia solani* on Rice

Protective local soil application 10-day-old rice plants are watered with a suspension (spray mixture) prepared from formulated test compound, without contaminating the parts of the plants above the soil. The plants are infected three days later by placing a barley straw infected with *Rhizoctonia solani* between the rice plants in each pot. Fungus infestation is evaluated after incubation for 6 days in a climatic chamber at a day temperature of 29° C. and a night temperature of 26° C. and at 95% relative humidity. Less than 5% of the rice plants are infested. The plants have a healthy appearance.

Protective local foliar application 12-day-old rice plants are sprayed with a suspension prepared from formulated test compounds. The plants are infected one day later by placing a barley straw infected with *Rhizoctonia solani* between the rice plants in each pot. Evaluation is made after incubation for 6 days in a climatic chamber at a day temperature of 29° C. and a night temperature of 26° C. and at 95% relative humidity. Fungus infestation is 100% on untreated and infected control plants. The compounds of formula I inhibit disease infestation in some cases completely.

B. Insecticidal Action

Example B16

Action Against *Aphis craccivora*

Pea seedlings are infested with *Aphis craccivora* and then sprayed with a spray mixture comprising 100 ppm of test compound, and incubated at 20° C. The percentage reduction in the population (% activity) is determined 3 and 6 days later by comparing the number of dead aphids on the treated plants with that on untreated plants.

Compounds of Tables 3 to 14 exhibit good activity in this test.

Example B17

Action Against *Diabrotica balteata*

Maize seedlings are sprayed with an aqueous emulsion comprising 100 ppm of test compound. After the spray coating has dried, the maize seedlings are populated with 10 *Diabrotica balteata* larvae in the second stage and then placed in a plastics container. The percentage reduction in the population (% activity) is determined 6 days later by comparing the number of dead larvae on the treated plants with that on untreated plants.

Compounds of Tables 3 to 14 exhibit good activity in this test. In particular, compounds 3.1, 3.2, 3.3, 3.4, 3.11, 3.15, 3.35, 3.36, 3.44, 3.57, 3.77, 3.78, 3.81, 3.94, 3.103, 4.57, 4.103, 5.57 and 5.103 are completely effective.

Example B18

Action Against *Heliothis virescens*

Young soybean plants are sprayed with an aqueous emulsion comprising 100 ppm of test compound. After the spray coating has dried, the soybean plants are populated with 10 *Heliothis virescens* caterpillars in the first stage and then placed in a plastics container. The percentage reduction in the population and the percentage reduction in feeding damage (% activity) are determined 6 days later by comparing the number of dead caterpillars and the feeding damage on the treated plants with those on untreated plants.

Compounds of Tables 3 to 14 exhibit good activity in this test. In particular, compounds 3.1, 3.2, 3.3, 3.4, 3.11, 3.15, 3.35, 3.36, 3.44, 3.57, 3.77, 3.78, 3.81, 3.94, 3.103, 4.57, 4.103, 5.57 and 5.103 are completely effective.

Example B19

Action Against *Spodoptera littoralis*

Young soybean plants are sprayed with an aqueous emulsion comprising 100 ppm of test compound. After the spray coating has dried, the soybean plants are populated with 10 *Spodoptera littoralis* caterpillars in the third stage and then placed in a plastics container. The percentage reduction in the population and the percentage reduction in feeding damage (% activity) are determined 3 days later by comparing the number of dead caterpillars and the feeding damage on the treated plants with those on untreated plants.

Compounds of Tables 3 to 14 exhibit good activity in this test. In particular, compounds 3.1, 3.2, 3.3, 3.4, 3.11, 3.15, 3.35, 3.36, 3.44, 3.57, 3.77, 3.78, 3.81, 3.94, 3.103, 4.57, 4.103, 5.57 and 5.103 are completely effective.

Example B20

Feeding Action Against *Ctenocephalides felis*
(Systemic)

20 adult fleas of the species *Ctenocephalides felis* are introduced into a flat round cage closed off at both ends with gauze. A vessel sealed at the bottom with a parafilm membrane is then placed on the cage. The vessel contains blood comprising 50 ppm of active ingredient and is heated to a constant temperature of 37° C. The fleas take up the blood through the membrane. Evaluation is effected 24 and 48 hours after the start of the test. The percentage reduction in population (% activity) is determined from a comparison of the number of dead fleas given treated blood with those given untreated blood. 24 hours after treatment the blood is replaced with fresh blood that has likewise been treated.

Compounds of Tables 3 to 14 exhibit good activity in this test.

Example B21

Action Against *Musca domestica*

A sugar cube is treated with a solution of the test compound in such a manner that, after drying overnight, the concentration of test compound in the sugar is 250 ppm. The treated cube is placed with a wet cotton wool swab and 10 *Musca domestica* adults of an OP resistant strain on an aluminium dish, covered with a glass beaker and incubated at 25° C. The mortality is determined after 24 hours.

Compounds of Tables 3 to 14 exhibit good activity in this test.

C. Acaricidal Action

Example B22

Action Against *Tetranychus urticae*

Young bean plants are populated with a mixed population of *Tetranychus urticae* and sprayed one day later with an aqueous emulsion comprising 100 ppm of test compound. The plants are then incubated for 6 days at 25° C. and then evaluated. The percentage reduction in the population (% activity) is determined by comparing the number of dead eggs, larvae and adults on the treated plants with that on untreated plants.

Compounds of Tables 3 to 14 exhibit good activity in this test. In particular, compounds 3.1, 3.2, 3.3, 3.4, 3.11, 3.15, 3.35, 3.36, 3.44, 3.57, 3.77, 3.78, 3.81, 3.94, 3.103, 4.57, 4.103, 5.57 and 5.103 are completely effective.

Example B23

Action Against *Boophilus microplus*

Adult *Boophilus microplus* females which are replete with blood are affixed to a PVC plate and covered with a cotton wool swab. For treatment, 10 ml of an aqueous test solution comprising 125 ppm of the test compound are poured over the test insects. The cotton wool swab is then removed and the ticks are incubated for 4 weeks until oviposition has taken place. The action against *Boophilus microplus* manifests itself either as mortality or sterility of the female or as ovicidal action in the eggs.

Compounds of Tables 3 to 14 exhibit good activity in this test.

What is claimed is:

1. A compound of formula

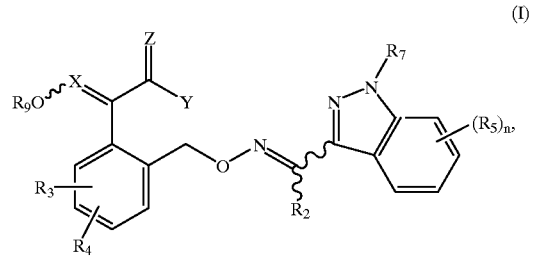

wherein
X is CH or N, Y is $OR_1$ and Z is O, or
X is N, Y is $NHR_8$ and Z is O, S or S(=O);
$R_1$ is $C_1$–$C_4$alkyl;
$R_2$ is H, $C_1$–$C_4$alkyl, halo-$C_1$–$C_4$alkyl, $C_3$–$C_6$cycloalkyl, $C_1$–$C_4$alkoxymethyl, $C_1$–$C_4$alkoxy, halo-$C_1$–$C_4$alkoxy, $C_1$–$C_4$alkylthio, halo-$C_1$–$C_4$alkylthio or —CN;
$R_3$ and $R_4$ are each independently of the other H, $C_1$–$C_4$alkyl, $C_1$–$C_4$alkoxy, OH, —CN, $NO_2$; a $(C_1$–$C_4$alkyl$)_3$Si group wherein the alkyl groups may be identical or different; halogen, $(C_1$–$C_4$alkyl)S(=O)$_m$, (halo-$C_1$–$C_4$alkyl)S(=O)$_m$, halo-$C_1$–$C_4$alkyl or halo-$C_1$–$C_4$alkoxy;
$R_5$ is unsubstituted or substituted $C_1$–$C_6$alkyl, $C_1$–$C_6$alkoxy, halo-$C_1$–$C_6$alkoxy, $C_1$–$C_6$-alkylthio, halo-$C_1$–$C_6$alkylthio, $C_1$–$C_6$alkylsulfinyl, halo-$C_1$–$C_6$alkylsulfinyl, $C_1$–$C_6$alkylsulfonyl, halo-$C_1$–$C_6$alkylsulfonyl, $C_1$–$C_6$alkylcarbonyl, halo-$C_1$–$C_6$alkylcarbonyl, $C_1$–$C_6$alkoxycarbonyl, halo-$C_1$–$C_6$alkoxycarbonyl, $C_1$–$C_6$alkylaminocarbonyl; di($C_1$–$C_6$alkyl)aminocarbonyl wherein the alkyl groups may be identical or different; $C_1$–$C_6$alkylaminothiocarbonyl; di($C_1$–$C_6$alkyl) aminothiocarbonyl wherein the alkyl groups may be identical or different; $C_1$–$C_6$alkylamino, di($C_1$–$C_6$alkyl)amino, halogen, $NO_2$; an unsubstituted or mono- to tetra-substituted $C_1$–$C_4$alkylenedioxy group, the substituents being selected from the group consisting of $C_1$–$C_4$alkyl and halogen; $QR_6$, —CN or $SF_5$ wherein, when n is greater than 1, the radicals $R_5$ may be identical or different;

$R_6$ is a $C_2$–$C_6$alkenyl or $C_2$–$C_6$alkynyl group that is unsubstituted or substituted by from 1 to 3 halogen atoms; a $(C_1$–$C_4$alkyl$)_3$Si group wherein the alkyl groups may be identical or different; —CN; an unsubstituted or mono- to penta-substituted $C_3$–$C_6$cycloalkyl, aryl or heterocyclyl group, the substituents being selected from the group consisting of halogen, $C_1$–$C_6$alkyl, halo-$C_1$–$C_6$alkyl, $C_1$–$C_6$alkoxy, halo-$C_1$–$C_6$alkoxy, phenoxy and —CN;

$R_7$ is H, unsubstituted or substituted $C_1$–$C_6$alkyl, $C_3$–$C_6$cycloalkyl; a $C_2$–$C_6$alkenyl or $C_2$–$C_6$alkynyl group that is unsubstituted or substituted by from 1 to 3 halogen atoms; phenyl or mono- to penta-substituted phenyl, the substituents being selected from the group consisting of $C_1$–$C_4$alkyl, halo-$C_1$–$C_4$alkyl, halogen, $C_1$–$C_4$alkoxy and halo-$C_1$–$C_4$alkoxy;

$R_8$ is H or $C_1$–$C_4$alkyl;

$R_9$ is $CH_3$, $CH_2F$ or $CHF_2$;

Q is a direct bond, O, O($C_1$–$C_6$alkylene), ($C_1$–$C_6$alkylene)O, S(=O)$_p$, S(=O)$_p$($C_1$–$C_6$alkylene), ($C_1$–$C_6$alkylene)S(=O)$_p$, $C_1$–$C_8$alkylene, $C_2$–$C_6$alkenylene or $C_2$–$C_6$alkynylene;

m is 0, 1 or 2;

n is 0, 1, 2, 3 or 4; and p is 0, 1 or 2, or one of the possible E/Z isomers, or mixtures of E/Z isomers and/or tautomers thereof, in each case in free form or in salt form.

2. A compound according to claim 1 of formula I, wherein

X is CH, or one of the possible E/Z isomers, or mixtures of E/Z isomers and/or tautomers thereof, in each case in free form or in salt form.

3. A compound according to claim 1 of formula I, wherein

Y is $OR_1$, or one of the possible E/Z isomers, or mixtures of E/Z isomers and/or tautomers thereof, in each case in free form or in salt form.

4. A compound according to claim 1 of formula I, wherein

Z is O, or one of the possible E/Z isomers, or mixtures of E/Z isomers and/or tautomers thereof, in each case in free form or in salt form.

5. A compound according to claim 1 of formula I, wherein $R_1$ is $C_1$–$C_2$alkyl, or one of the possible E/Z isomers, or mixtures of E/Z isomers and/or tautomers thereof, in each case in free form or in salt form.

6. A compound according to claim 1 of formula I, wherein $R_2$ is $C_1$–$C_2$alkyl, halo-$C_1$–$C_2$alkyl, cyclopropyl, halo-$C_1$–$C_2$alkylthio or CN, or one of the possible E/Z isomers, or mixtures of E/Z isomers and/or tautomers thereof, in each case in free form or in salt form.

7. A compound according to claim 1 of formula I, wherein $R_3$ and $R_4$ are each independently of the other H, $C_1$–$C_2$alkyl, $C_1$–$C_2$alkoxy, CN, $NO_2$, $CF_3$ or halogen, or one of the possible E/Z isomers, or mixtures of E/Z isomers and/or tautomers thereof, in each case in free form or in salt form.

8. A compound according to claim 1 of formula I, wherein $R_5$ is $C_1$–$C_2$alkyl, halo-$C_1$–$C_2$alkyl, halogen or $QR_6$, or one of the possible E/Z isomers, or mixtures of E/Z isomers and/or tautomers thereof, in each case in free form or in salt form.

9. A compound according to claim 1 of formula I, wherein $R_6$ is a $C_2$–$C_3$alkenyl or propynyl group that is unsubstituted or substituted by 1 or 2 halogen atoms; or an unsubstituted or mono- to tri-substituted cyclopropyl or phenyl group, the substituents being selected from the group consisting of halogen, methyl, halomethyl, methoxy and CN, or one of the possible E/Z isomers, or mixtures of E/Z isomers and/or tautomers thereof, in each case in free form or in salt form.

10. A compound according to claim 1 of formula I, wherein $R_7$ is $C_1$–$C_2$alkyl, or one of the possible E/Z isomers, or mixtures of E/Z isomers and/or tautomers thereof, in each case in free form or in salt form.

11. A compound according to claim 1 of formula I, wherein $R_8$ is $C_1$–$C_2$alkyl, or one of the possible E/Z isomers, or mixtures of E/Z isomers and/or tautomers thereof, in each case in free form or in salt form.

12. A compound according to claim 1 of formula I, wherein $R_9$ is methyl, or one of the possible E/Z isomers, or mixtures of E/Z isomers and/or tautomers thereof, in each case in free form or in salt form.

13. A compound according to claim 1 of formula I, wherein

Q is O or O(methylene), or one of the possible E/Z isomers, or mixtures of E/Z isomers and/or tautomers thereof, in each case in free form or in salt form.

14. A compound according to claim 1 of formula I, wherein n is 0, 1 or 2, or one of the possible E/Z isomers, or mixtures of E/Z isomers and/or tautomers thereof, in each case in free form or in salt form.

15. A compound according to claim 1 of formula I, wherein

X is CH, Y is $OR_1$, Z is O, $R_1$ is $C_1$–$C_2$alkyl, $R_2$ is $C_1$–$C_3$alkyl, halo-$C_1$–$C_2$alkyl, cyclopropyl, halo-$C_1$–$C_2$alkylthio or CN, $R_3$ and $R_4$ are each independently of the other H, $C_1$–$C_2$alkyl, $C_1$–$C_2$alkoxy, $CF_3$ or halogen, $R_5$ is $C_1$–$C_2$alkyl, halo-$C_1$–$C_2$alkyl, halogen or $QR_6$, $R_6$ is a $C_2$–$C_6$alkenyl or $C_2$–$C_6$alkynyl group that is unsubstituted or substituted by from 1 to 3 halogen atoms, or an unsubstituted or mono- to tri-substituted $C_3$–$C_6$cycloalkyl or phenyl group, the substituents being selected from the group consisting of halogen, $C_1$–$C_6$alkyl, halo-$C_1$–$C_6$alkyl, $C_1$–$C_6$alkoxy and CN, $R_7$ is $C_1$–$C_2$alkyl, $R_9$ is methyl or $CH_2F$, Q is O or O($C_1$–$C_2$alkylene), and n is 0, 1 or 2, or one of the possible E/Z isomers, or mixtures of E/Z isomers and/or tautomers thereof, in each case in free form or in salt form.

16. A compound according to claim 1 of formula I, wherein

X is CH, Y is methoxy, Z is O, $R_2$ is $C_1$–$C_3$alkyl, halomethyl, cyclopropyl, halomethylthio or CN, $R_3$ and $R_4$ are each independently of the other H, methyl, methoxy, chlorine or fluorine, $R_5$ is methyl, fluorine, chlorine or $QR_6$, $R_6$ is a cyclopropyl or phenyl group that is unsubstituted or mono- to tri-substituted by halogen, methyl, halomethyl or by methoxy, $R_7$ is $C_1$–$C_2$alkyl, $R_9$ is methyl, Q is O or O(methylene), and n is 0, 1 or 2, or one of the possible E/Z isomers, or mixtures of E/Z isomers and/or tautomers thereof, in each case in free form or in salt form.

17. A compound according to claim 1, selected from the group of compounds consisting of 2-[[[(1-{1-methylindazol-3-yl}ethylidene)amino]oxy]methyl]-α-(methoxymethylene)phenylacetic acid methyl ester, 2-[[[(1-{6-[(2,2-dichlorocyclopropyl)methoxy]-5-fluoro-1-methylindazol-3-yl}ethylidene)amino]oxy]methyl]-α-(methoxymethylene)phenylacetic acid methyl ester, 2-[[[(1-{5-fluoro-6-[(4-fluorophenyl)methoxy]-1-methylindazol-3-yl}ethylidene)amino]oxy]methyl]-α-(methoxymethylene)phenylacetic acid methyl ester and 2-[[[(1-{6-fluoro-1-methylindazol-3-yl}ethylidene)amino]oxy]methyl]-α-(methoxymethylene)phenylacetic acid methyl ester.

18. A process for the preparation of a compound according to claim 1 of formula I, or one of the E/Z isomers or tautomers thereof, in free form or in salt form, which process comprises:

a) for the preparation of a compound of formula I wherein Y is $OR_1$ and Z is O, either reacting a compound of formula

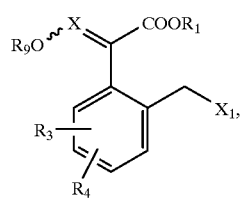

(II)

wherein X, $R_1$, $R_3$, $R_4$ and $R_9$ are as defined for formula I, and $X_1$ is a leaving group, optionally in the presence of a base, with a compound of formula

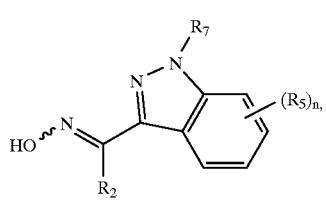

(III)

wherein n, $R_2$, $R_5$ and $R_7$ are as defined for formula I, or reacting a compound of formula

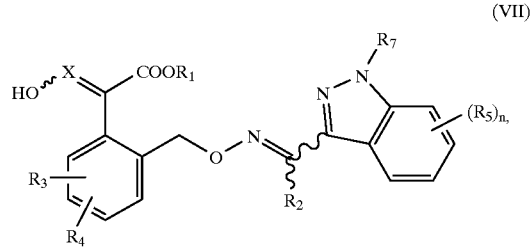

(VII)

wherein n, X, $R_2$, $R_3$, $R_4$, $R_5$ and $R_7$ are as defined for formula I, optionally in the presence of a base, with a compound of the formula $X_3R_9$, wherein $R_9$ is as defined for formula I and $X_3$ is a leaving group, or b) for the preparation of a compound of formula I wherein Y is $NHR_8$ and Z is O, reacting a compound of formula I wherein Y is $OR_1$, obtainable in accordance with process variant a), with a compound of the formula $NH_2R_8$, wherein $R_8$ is as defined for formula I, or c) for the preparation of a compound of formula I wherein Z is S, reacting a compound of formula I wherein Y is $NH_2R_8$ and Z is O, obtainable in accordance with process variant b), with $P_4S_{10}$ or Lawesson's reagent, or d) for the preparation of a compound of formula I wherein Z is SO, reacting a compound of formula I wherein Z is S, obtainable in accordance with process variant c), with an oxidizing agent, and optionally converting a compound of formula I, or an E/Z isomer or a tautomer thereof, in each case in free form or in salt form, into a different compound of formula I or an E/Z isomer or a tautomer thereof, in each case in free form or in salt form, separating a mixture of E/Z isomers obtainable in accordance with the process and isolating the desired isomer and/or converting a free compound of formula I, or an E/Z isomer or a tautomer thereof, into a salt or converting a salt of a compound of formula I, or of an E/Z isomer or of a tautomer thereof, into the free compound of formula I or an E/Z isomer or a tatuomer thereof or into a different salt.

19. A compound of formula

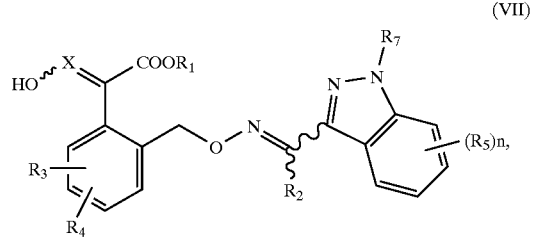

(VII)

wherein n, X, $R_1$, $R_2$, $R_3$, $R_5$, and $R_7$ are as defined for formula I in claim 1.

20. A process for the preparation of a compound according to claim 19 of formula VII, in free form or in salt form, which process comprises:

g) for the preparation of a compound of formula VII wherein X is CH, reacting a compound of formula

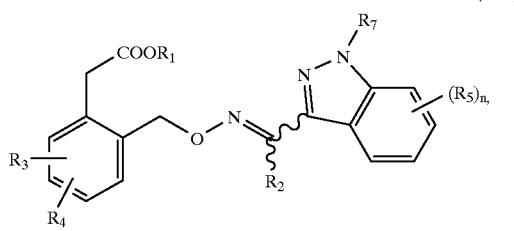

(VIII)

wherein n, X, $R_2$, $R_3$, $R_4$, $R_5$ and $R_7$ are as defined for formula I, optionally in the presence of a base, with a formic acid $C_1$–$C_6$alkyl ester, or h) for the preparation of a compound of formula VII wherein X is N, reacting a compound of formula VIII, optionally in the presence of a base, with a $C_1$–$C_6$alkyl nitrite, and optionally converting a compound of formula VII, or an E/Z isomer or a tautomer thereof, in each case in free form or in salt form, into a different compound of formula VII or an E/Z isomer or a tautomer thereof, in each case in free form or in salt form, separating a mixture of E/Z isomers obtainable in accordance with the process and isolating the desired isomer and/or converting a free compound of formula VII, or an E/Z isomer or a tautomer thereof, into a salt or converting a salt of a compound of formula VII, or of an E/Z isomer or of a tautomer thereof, into the free compound of formula VII or an E/Z isomer or a tautomer thereof or into a different salt.

21. A composition which comprises at least one compound according to claim 1 of formula I or an E/Z isomer or a tautomer thereof, in free form or in agrochemically acceptable salt form, in an effective pesticidal amount, and at least one adjuvant.

22. A process for the preparation of a composition according to claim 21, which comprises intimately mixing and/or grinding the active ingredient with the adjuvant(s).

23. A method of controlling pests, which comprises applying a compound according to formula I of claim 1 to the pests or the habitat thereof.

24. A method according to claim 23 for the protection of plant propagation material, which comprises treating the propagation material or the planting site of the propagation material.

25. Plant propagation material treated in accordance with the method described in claim 24.

\* \* \* \* \*